United States Patent
Hammond et al.

(10) Patent No.: US 9,061,984 B2
(45) Date of Patent: Jun. 23, 2015

(54) COMPOUNDS RELATED TO CHALCONES AND BENZOTHIENOPYRIMIDINES, THEIR SYNTHESIS, AND USES TO TREAT DISEASES

(75) Inventors: Gerald B. Hammond, Louisville, KY (US); Jose C. Aponte, Riverside, RI (US); Robert H. Gilman, Grantsville, MD (US); Michel Henri Auguste Sauvain, Ramonville Saint Agne (FR); Abraham Vaisberg, Lima (PE)

(73) Assignees: University of Louisville Research Foundation, Inc., Louisville, KY (US); Universidad Peruma Cayetano Heredia, Lima (PE); Institut de recherche pour le développement, Marseilles (FR); The Johns Hopkins University, Baltimore, MD (US)

(*) Notice: Subject to any disclaimer, the term of this patent is extended or adjusted under 35 U.S.C. 154(b) by 734 days.

(21) Appl. No.: 13/058,863

(22) PCT Filed: Aug. 14, 2009

(86) PCT No.: PCT/US2009/053856
§ 371 (c)(1), (2), (4) Date: Apr. 26, 2011

(87) PCT Pub. No.: WO2010/019861
PCT Pub. Date: Feb. 18, 2010

(65) Prior Publication Data
US 2011/0190325 A1    Aug. 4, 2011

Related U.S. Application Data

(60) Provisional application No. 61/089,231, filed on Aug. 15, 2008.

(51) Int. Cl.
| | |
|---|---|
| *C07D 317/48* | (2006.01) |
| *C07C 49/84* | (2006.01) |
| *C07C 45/62* | (2006.01) |
| *C07C 45/67* | (2006.01) |
| *C07C 45/71* | (2006.01) |
| *C07C 45/74* | (2006.01) |
| *C07D 495/04* | (2006.01) |

(52) U.S. Cl.
CPC .............. *C07C 49/84* (2013.01); *C07C 45/62* (2013.01); *C07C 45/673* (2013.01); *C07C 45/71* (2013.01); *C07C 45/74* (2013.01); *C07D 495/04* (2013.01)

(58) Field of Classification Search
None
See application file for complete search history.

(56) References Cited

U.S. PATENT DOCUMENTS

2007/0155779 A1    7/2007 Verhoest et al.
2007/0232661 A1    10/2007 Beachy et al.

FOREIGN PATENT DOCUMENTS

| WO | 2005037213 A2 | 4/2005 |
| WO | 2006029850 A1 | 3/2006 |

OTHER PUBLICATIONS

Makrandi. Synthetic Communications, 1990, 20(12), 1885-8.*
Wermuth. The Practice of Medicinal Chemistry, 1996, pp. 203-237.*
Chibber. Current Science, 1982, 51(19), 933-34.*
Norbedo. Journal of Natural Products, 1982, 45 (5), 635-6.*
Puyvelde. Journal of Natural Products, 1989, 52 (3), 629-33.*
Levene. Journal of Biological Chemistry, 1917, 31, 635-47.*
Villamil. Spectroscopy (Amsterdam, Netherlands), 1988, 6(3-4), 157-65.*
Esteve. Journal of High Resolution Chromatography, 1989, 416-19.*
Jin. Archives of Pharmacal Research, 2007, 30 (11), 1359-67.*
Jung. Bulletin of the Korean Chemical Society, 2008, 29 (6), 1199-1204.*
PCT/US2009/053856, International Search Report, mailed Oct. 13, 2009, 2 pp.
PCT/US2009/053856, Written Opinion, mailed Oct. 13, 2009, 6 pp.
Barreca et al., "Early detection of *Leishmania* promastigotes in dog bone marrow cultures by acridine orange stain" Diagn. Microbiol. Infect. Dis. (2000) vol. 37, pp. 247-251.
Bhuiyan et al., "Synthesis and antimicrobial evaluation of some new thienopyrimidine derivatives" Acta Pharm. (2006) vol. 56, pp. 441-450.
Boeck et al., "Synthesis of chalcone analogues with increased antileishmanial activity" Bioorganic & Medicinal Chemistry (2006) vol. 14, pp. 1538-1545.
Boyd et al., "Some Practical Considerations and Applications of the National Cancer Institute In Vitro Anticancer Drug Discovery Screen" Drug Dev. Res. (1995) vol. 34, pp. 91-109.
Buckner et al., "Efficient technique for screening drugs for activity against *Trypanosoma cruzi* using parasites expressing beta-galactosidase" Antimicrob. Agents and Chemotherapy (Nov. 1996) vol. 40, No. 11, pp. 2592-2597.
Castillo et al., "Spirolactone iridoids might be responsible for the antileishmanial activity of a Peruvian traditional remedy made with *Himatanthus* sucuuba (Apocynaceae)" Journal of Ethnopharmacology (2007) vol. 112, pp. 410-414.
Delorenzi et al., "Antileishmanial Activity of an Indole Alkaloid from *Peschiera australis*" Antimicrobial Agents and Chemotherapy (May 2001) vol. 45, No. 5, pp. 1349-1354.
Fautz et al., "Application of the neutral red assay (NR assay) to monolayer cultures of primary hepatocytes: rapid colorimetric viability determination for the unscheduled DNA synthesis test (UDS)" Mutation Research (1991) vol. 253, pp. 173-179.

(Continued)

*Primary Examiner* — Noble Jarrell
(74) *Attorney, Agent, or Firm* — Thrive IP®; Jeremy M. Stipkala

(57) ABSTRACT

Embodiments of the present invention provide compounds (such as Formula (I) compounds, Formula (II) compounds, and various embodiments thereof). Compositions comprising those compounds are also provided. Methods for their preparation are included. Also, uses of the compounds are included, such as administering and treating diseases (e.g., cancer and infections).

11 Claims, No Drawings

(56) References Cited

OTHER PUBLICATIONS

Jackson et al., "Fluorogenic Substrate Detection of Viable Intracellular and Extracellular Pathogenic Protozoa" Science (Jan. 25, 1985) vol. 227, pp. 435-438.

Liu et al., "Structure-Activity Relationships of Antileishmanial and Antimalarial Chalcones" Bioorg. and Med. Chem. (2003) vol. 11, pp. 2729-2738.

Monks et al., "Feasibility of a High-Flux Anticancer Drug Screen Using a Diverse Panel of Cultured Human Tumor Cell Lines" J. Natl. Cancer Inst. (1991) vol. 83, pp. 757-766.

Sauvain et al., "In Vitro and In Vivo Leishmanicidal Activities of Natural and Synthetic Quinoids" Phytotherapy Research (1993) vol. 7, pp. 167-171.

Skehan et al., "New Colorimetric Cytotoxicity Assay for Anticancer-Drug Screening" J. Natl. Cancer Inst. (1990) vol. 82, pp. 1107-1112.

Teixeira et al., "A simple and reproducible method to obtain large numbers of axenic amastigotes of different *Leishmania* species" Parasitology Research (2002) vol. 88, pp. 963-968.

Zhao et al., "Rate-limited steps of human oral absorption and QSAR studies" Pharm. Res. (2002) vol. 19, No. 10, pp. 1446-1457.

Boyd et al., "Data Display and Analysis Strategies for the NCI Disease-Oriented In Vitro Antitumor Drug Screen," in Cytotoxic Anticancer Drugs: Models and Concepts for Drug Discovery and Development: Proceedings of the Twenty-Second Annual Cancer Symposium, Detroit, Michigan, USA, Apr. 26-28, 1990, pp. 11-34 (1992).

EP09807350.5, European Search Report, mailed Jun. 10, 2014, 11 pp.

Vogel S et al., "Natural and non-natural prenylated chalcones; Synthesis cytotoxicity and anti-oxidative activity," Bioorganic & Medicinal Chemistry, vol. 16, No. 8, Apr. 15, 2008, pp. 4286-4293.

Jun et al., "Synthesis and evaluation of 2', 4', 6'-trihydroxychalcones as a new class of tyrosinase inhibitors," Bioorganic & Medicinal Chemistry, vol. 15, No. 6, Feb. 15, 2007, pp. 2396-2402.

Cheenpracha S et al., "Anti-HIV-1 protease activity of compounds from *Boesenbergia pandurata*," Bioorganic & Medicinal Chemistry, vol. 14, No. 6, Mar. 15, 2006, pp. 1710-1714.

Mesa-Siverio et al., "Structure and estrogenic activity of new lignans from *Iryanthera lancifolia*," Bioorganic & Medicinal Chemistry, vol. 16, No. 6, Dec. 8, 2007, pp. 3387-3394.

Gundla et al., "Discovery of Novel Small-Molecule Inhibitors of Human Epidermal Growth Factor Receptor-2: Cobmined Ligand and Target-Based Approach," Journal of Medicinal Chemistry, vol. 51, May 24, 2008, pp. 3367-3377.

\* cited by examiner

COMPOUNDS RELATED TO CHALCONES AND BENZOTHIENOPYRIMIDINES, THEIR SYNTHESIS, AND USES TO TREAT DISEASES

CROSS REFERENCE TO RELATED APPLICATIONS

This application is a National Stage Entry of International Application No. PCT/US2009/053856 filed Aug. 14, 2009, which is incorporated by reference in its entirety, which claims benefit to U.S. Provisional Application No. 61/089,231, filed Aug. 15, 2008, which is incorporated by reference in its entirety.

BACKGROUND

Embodiments of the present invention provide compounds (e.g., Formula (I) compounds and Formula (II) compounds, which include compounds related to chalcones and compounds related to benzothienopyrimidines (BTPs)), their preparations, and their uses (e.g., treating disease).

There is a need to find drugs to provide aid (such as treatment or cure) to diseased animals that will have one or more positive-outcome effects, such as anticancer, anti-inflammatory, immunomodulatory, antibacterial, immunosuppressive, and antiprotozoan activity, including, for example, trypanocidal, leishmanicidal and antimalarial activity. For instance, Chagas' disease or American trypanosomiasis—caused by the vector-borne flagellate protozoan parasite *Trypanosoma cruzi*—is an endemic tropical disease that has infected 20 million people in Central and South America and approximately between 50,000 and 100,000 people in the United States. Accordingly, some embodiments of the present invention provide compounds to treat or cure diseased animals.

SUMMARY

Some embodiments of the present invention include a compound of formula (I)

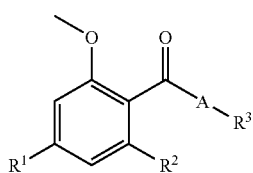
(I)

where $R^1$ and $R^2$ can be the same or different and are selected from the group consisting of: —OH, alkoxy, benzyloxy, —OCH$_2$—CH═CH$_2$, and —OCH$_2$OCH$_3$; A is a bivalent, substituted or unsubstituted, branched or unbranched alkane or alkene; and $R^3$ is a substituted or unsubstituted four-, five-, six-, or seven-member ring that optionally includes one or more heteroatoms in the ring. In some instances, the compound is not

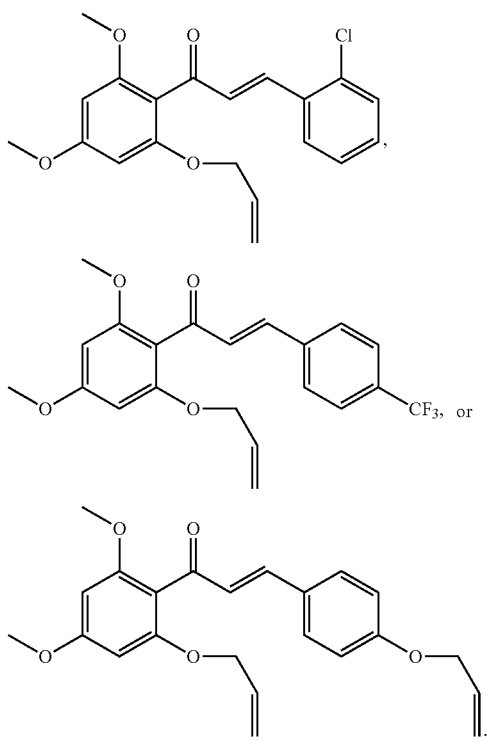

The formula (I) compounds can be part of a composition. In another embodiment, a method for synthesizing a compound of claim 1 comprises: subjecting

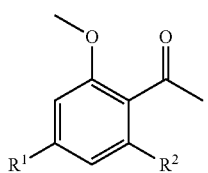

to a condensation reaction, and recovering

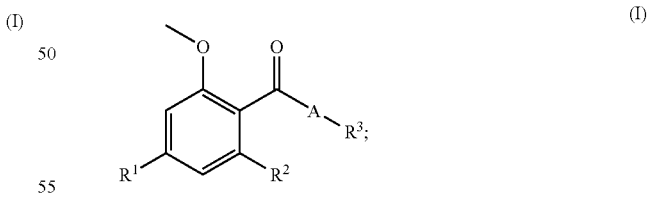
(I)

where $R^1$ and $R^2$ can be the same or different and are selected from the group consisting of: —OH, alkoxy, benzyloxy, —OCH$_2$—CH═CH$_2$, and —OCH$_2$OCH$_3$; A is a bivalent, substituted or unsubstituted, branched or unbranched alkane or alkene; and $R^3$ is a substituted or unsubstituted four-, five-, six-, or seven-member ring that may include one or more heteroatoms in the ring.

In still other embodiments, a method comprises administering a composition comprising a compound to at least one cell, where the compound is

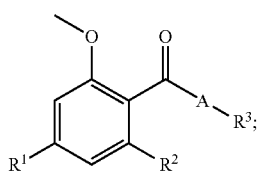
(I)

where $R^1$ and $R^2$ can be the same or different and are selected from the group consisting of: —OH, alkoxy, benzyloxy, —OCH$_2$—CH=CH$_2$, and —OCH$_2$OCH$_3$; A is a bivalent, substituted or unsubstituted, branched or unbranched alkane or alkene; and $R^3$ is a substituted or unsubstituted four-, five-, six-, or seven-member ring that may include one or more heteroatoms in the ring.

Some embodiments of the invention include a compound of formula (II)

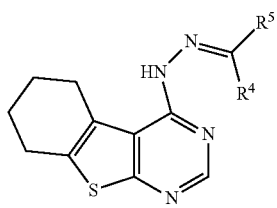
(II)

where $R^4$ and $R^5$ can be the same or different and are selected from the group consisting of: H, methyl, ethyl, propyl, isopropyl, butyl, sec-butyl, t-butyl, and substituted or unsubstituted four-, five-, six-, or seven-member ring that may include one or more heteroatoms in the ring. In some instances, if $R^4$ is a ring then $R^4$ may optionally be linked by a bivalent, substituted or unsubstituted, branched or unbranched alkane or alkene. In still other instances, $R^4$ and $R^5$ are not both H. In some embodiments, $R^4$ and $R^5$ can be selected according to either (i) $R^4$=methyl and $R^5$=phenyl; $R^4$=$R^5$=methyl; $R^4$=$R^5$=ethyl; or $R^4$=$R^5$=phenyl, or (ii) at least one of $R^4$ and $R^5$ is selected from the group consisting of:

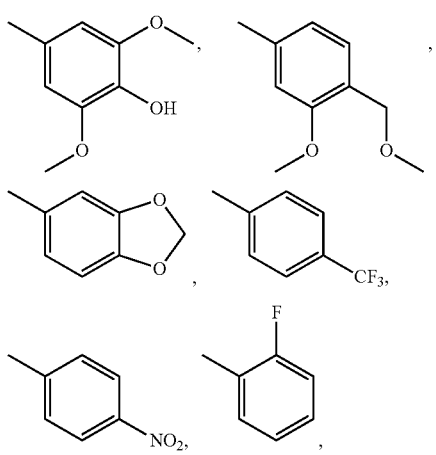

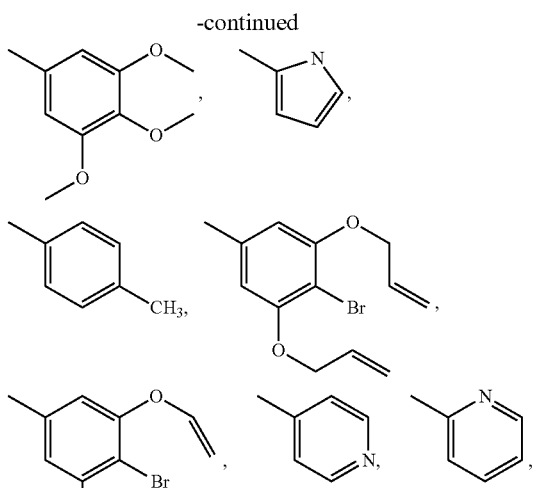

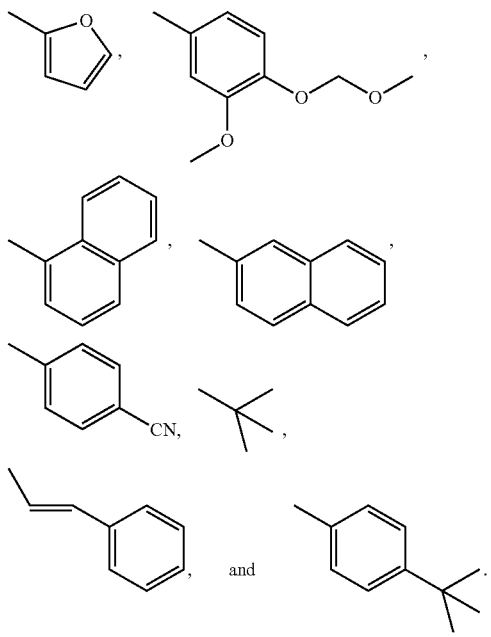

Further embodiments of the invention include compositions comprising the formula (II) compound or embodiments, as described above. Embodiments also include methods for synthesizing compounds of formula (II) (and the various embodiments thereof) comprising: subjecting

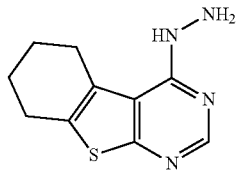 [SMILES: NNc1ncnc2sc3c(c12)CCCC3]

to a condensation reaction, and recovering the formula (II) compounds (or the embodiment thereof).

Further embodiments include, methods comprising administering a compound to at least one animal cell, where the compound is

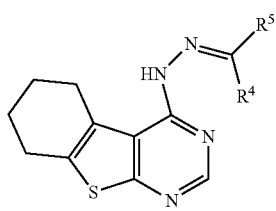

and R[4] and R[5] can be the same or different and are selected from the group consisting of: H, methyl, ethyl, propyl, isopropyl, butyl, sec-butyl, t-butyl, and substituted or unsubstituted four-, five-, six-, or seven-member ring that may include one or more heteroatoms in the ring. In some instances, if R[4] is a ring then R[4] may optionally be linked by a bivalent, substituted or unsubstituted, branched or unbranched alkane or alkene. In some embodiments the compound is not

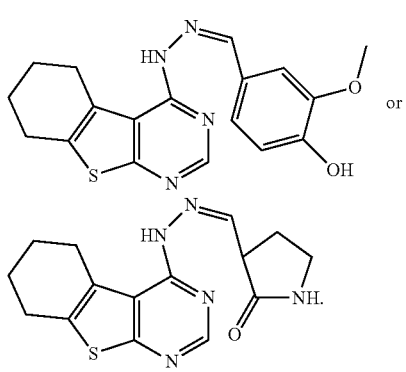

Other embodiments of the present invention will be apparent in light of the description of the invention herein.

DETAILED DESCRIPTION

The compounds of the present invention can include

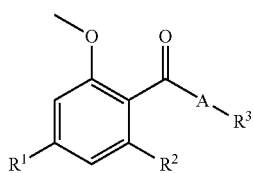

(I)

In some discussions below, the ring with R[1] and R[2] is referred to as Ring A and the R[3] system is referred to as Ring B. In some embodiments, R[1] and R[2] can be the same or different and selected from —OH, alkoxy, benzyloxy, —OCH$_2$—CH═CH$_2$ (allyloxy), or —OCH$_2$OCH$_3$. For example, one of R[1] or R[2] can be —OH or neither can be —OH. The alkoxy can, for example, be methoxy, ethoxy, or propoxy. In some embodiments, R[1] is —OCH$_3$ and R[2] is —OH; R[1] and R[2] are both —OH; R[1] and R[2] are both —OCH$_2$CH═CH$_2$; R[1] and R[2] are both —OCH$_2$OCH$_3$; or R[1] is —OCH$_2$OCH$_3$ and R[2] is —OH.

A can be a bivalent, substituted or unsubstituted, branched or unbranched alkane or alkene. Alkene is defined as a hydrocarbon with one or more double bonds. In some instances, A is a mixture of saturated and unsaturated hydrocarbon groups. In some embodiments, A can be,

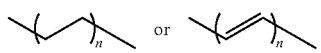

where n can be 1, 2, 3, or 4. In some instances, A is —CH$_2$—CH$_2$—, —CH$_2$CH$_2$CH$_2$CH$_2$—, —CH═CH—, or —CH═CH—CH═CH—.

R[3] can be a substituted or unsubstituted four-, five-, six-, or seven-member ring that may include one or more heteroatoms in the ring. Embodiments include rings that have, for example, one, two, three, four, five, or six substitutions. The ring can be conjugated, aromatic, unsaturated, or saturated. When the rings include heteroatoms, these heterocycles can have 1, 2, 3, or 4 heteroatoms (such as N, S, or O), which can be the same or different for a given ring. In some embodiments, R[3] can be a substituted or unsubstituted phenyl, naphthyl, furan, pyridine, or pyrrole. Substitutions can include, but are not limited to alkoxy (such as methoxy, ethoxy, propoxy), hydroxyl, amine, amide, halogens (e.g., F, Cl, Br), nitro, allyloxy, alkyloxyalkyl (such as methoxymethyl), alkyl (such as methyl, ethyl, propyl), substituted alkyl (e.g., tri-halogenated methyl, trifluoromethyl). R[3] can also be substituted with moieties that are attached at two ring positions to create a fused ring system such as alkylenedioxy (e.g., methylenedioxy (i.e., —OCH$_2$O)), naphthyl (e.g., 1-naphthyl or 2-naphthyl), benzofuranyl, indolyl, or quinolyl. In some embodiments, R[3] can be

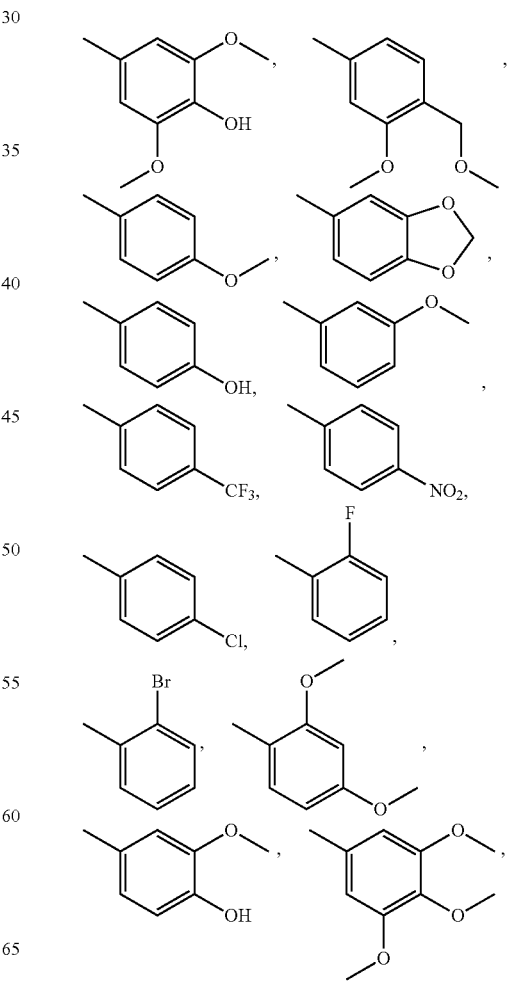

-continued
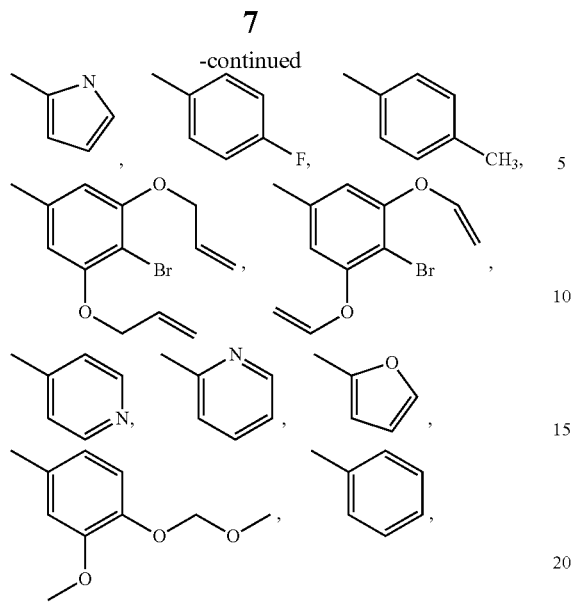
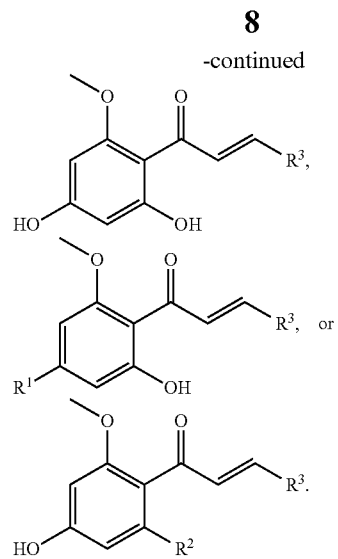
In some embodiments, the Formula (I) compounds are
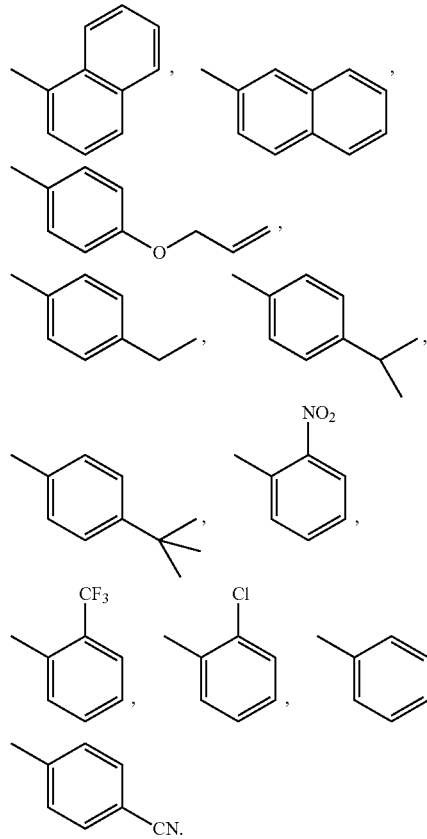
In some embodiments, the Formula (I) compounds are:
I-01
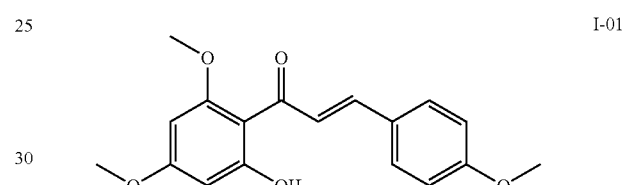
I-02
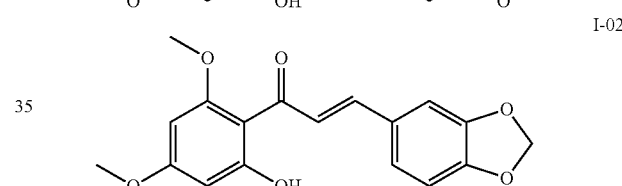
I-03
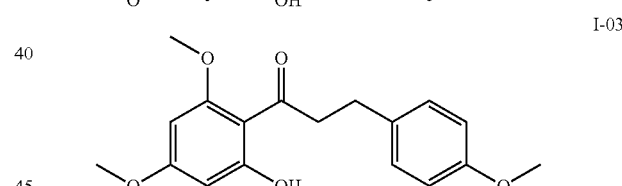
I-04
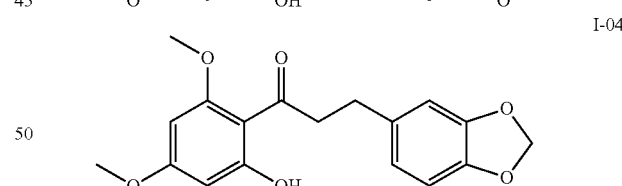
I-05
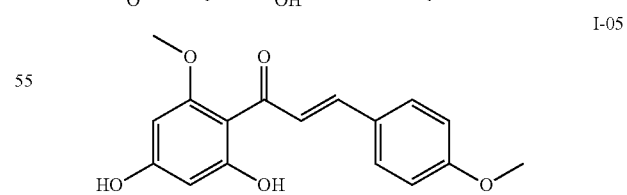
I-06
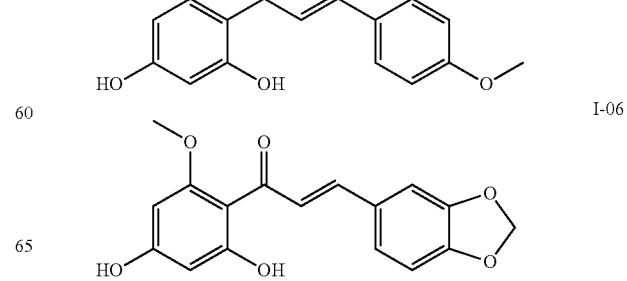

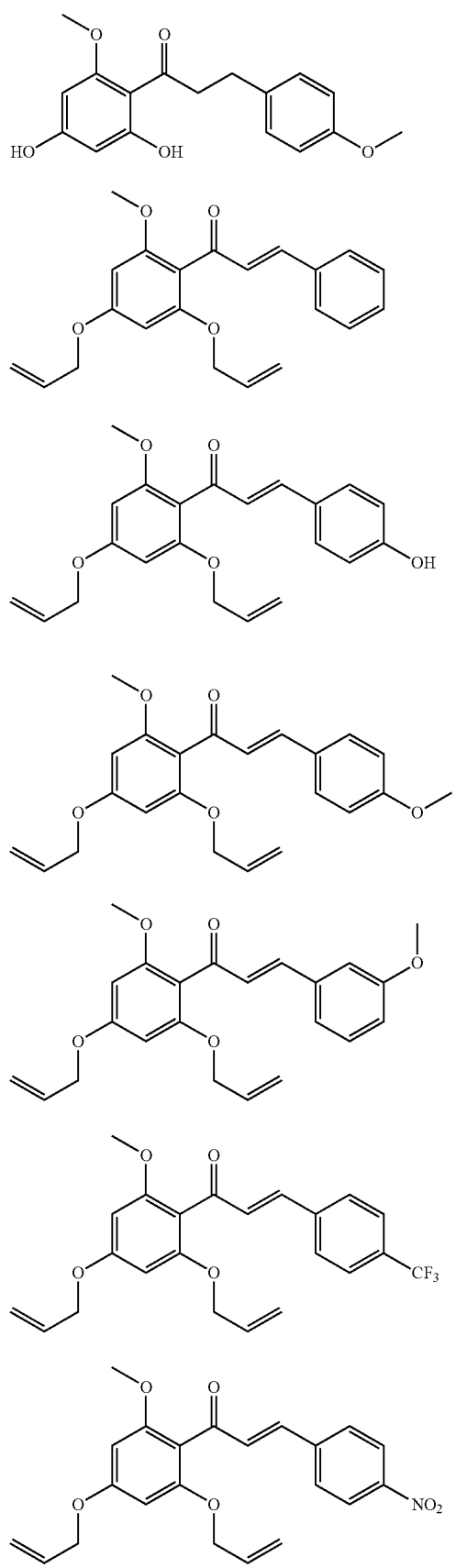
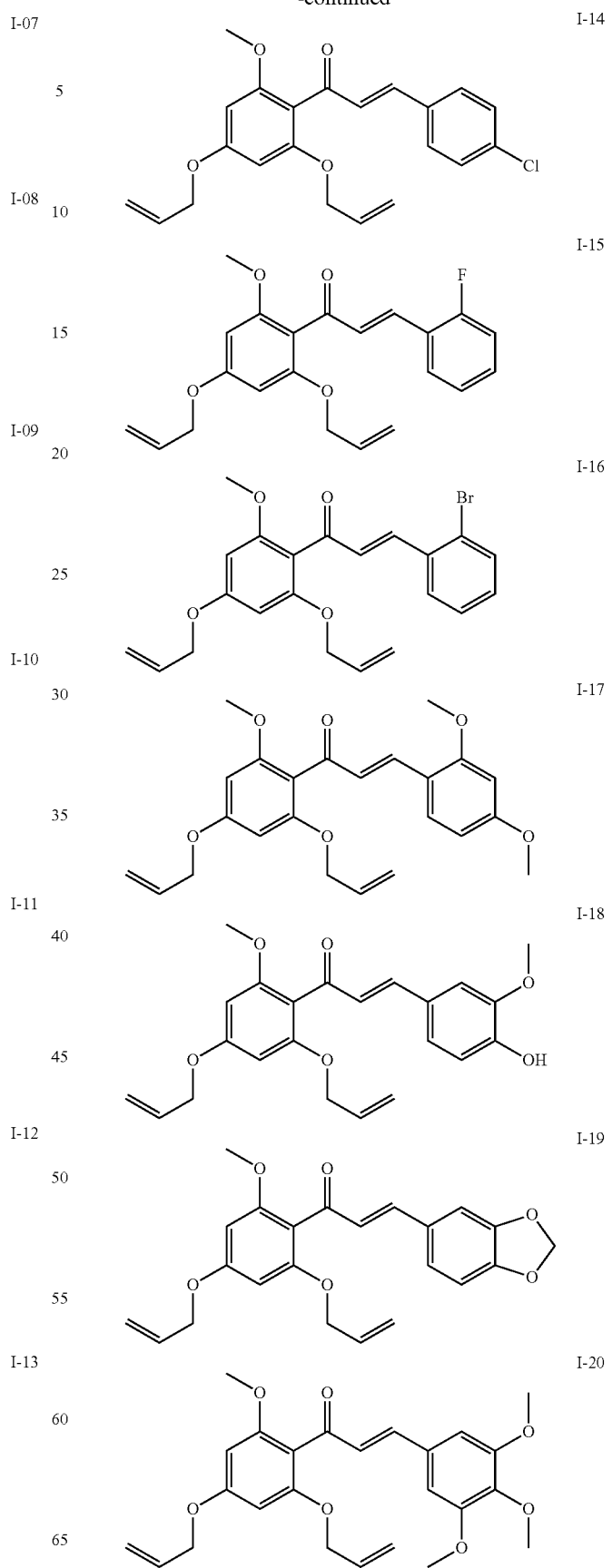

-continued
I-21
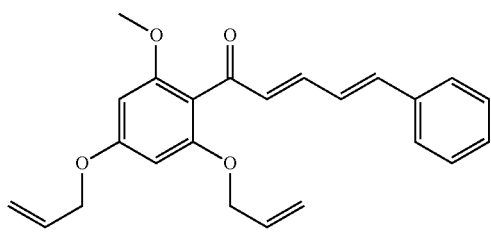
I-22
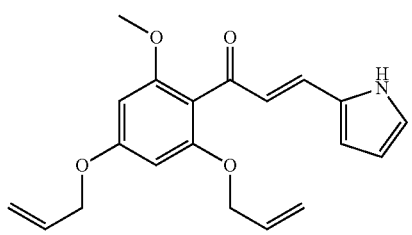
I-23
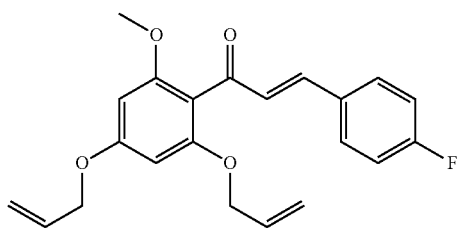
I-24
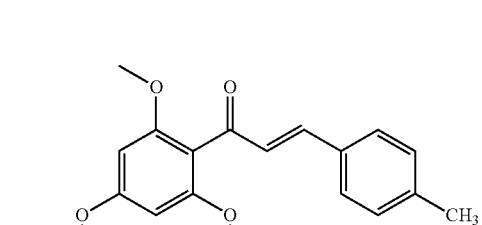
I-25
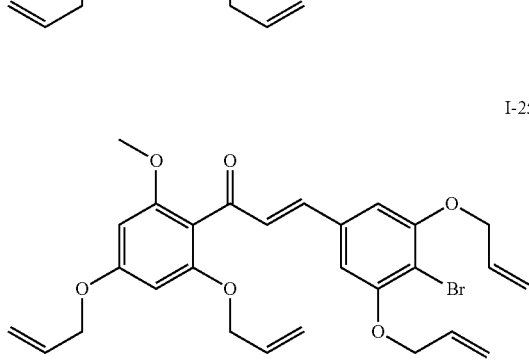
I-26
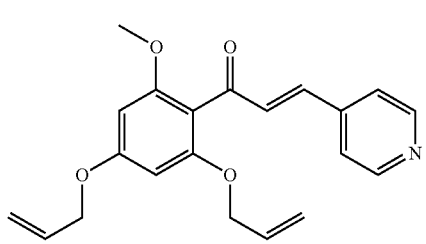
-continued
I-27
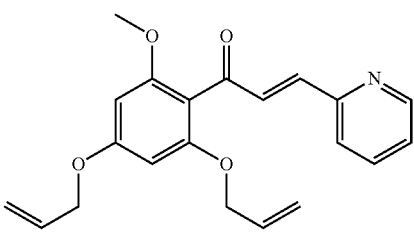
I-28
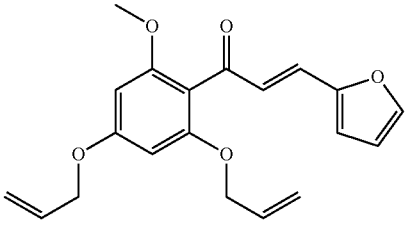
I-29
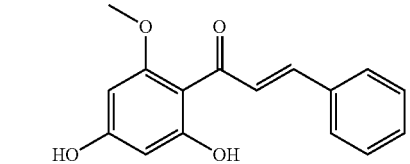
I-30
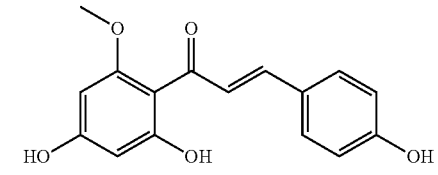
I-31
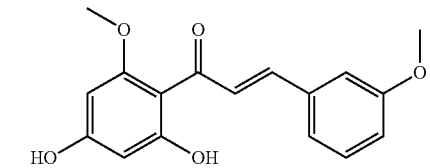
I-32
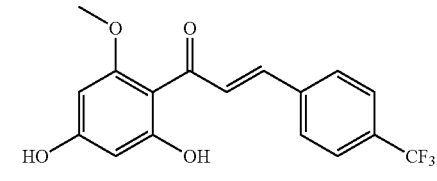
I-33
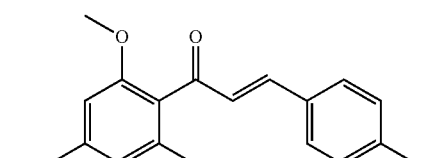
I-34
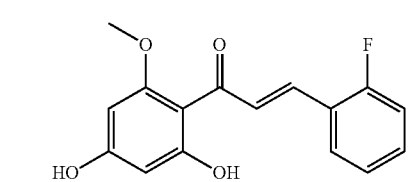

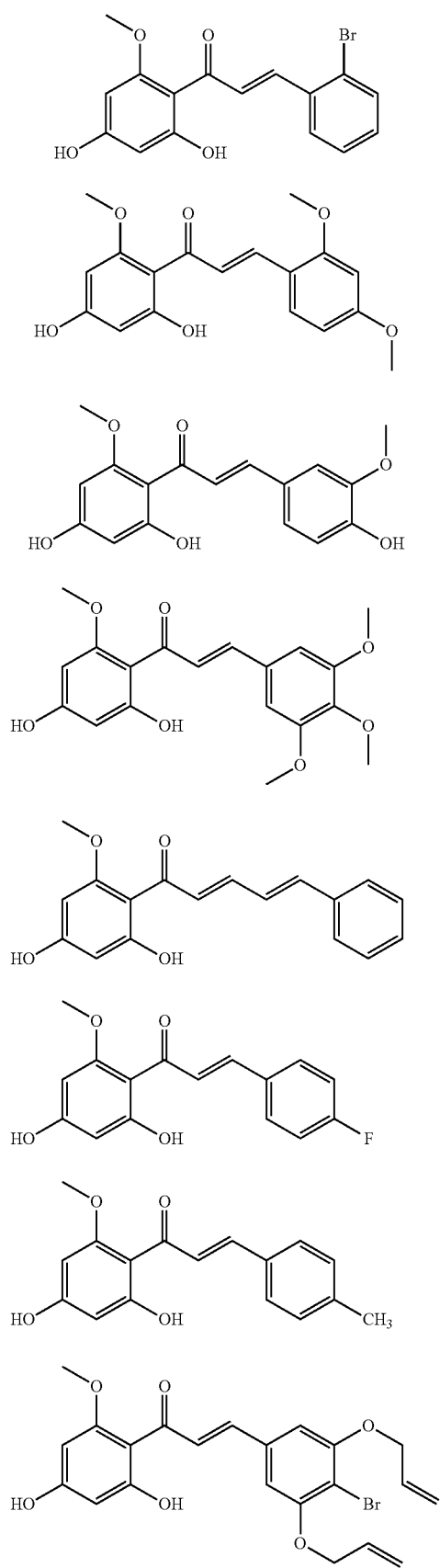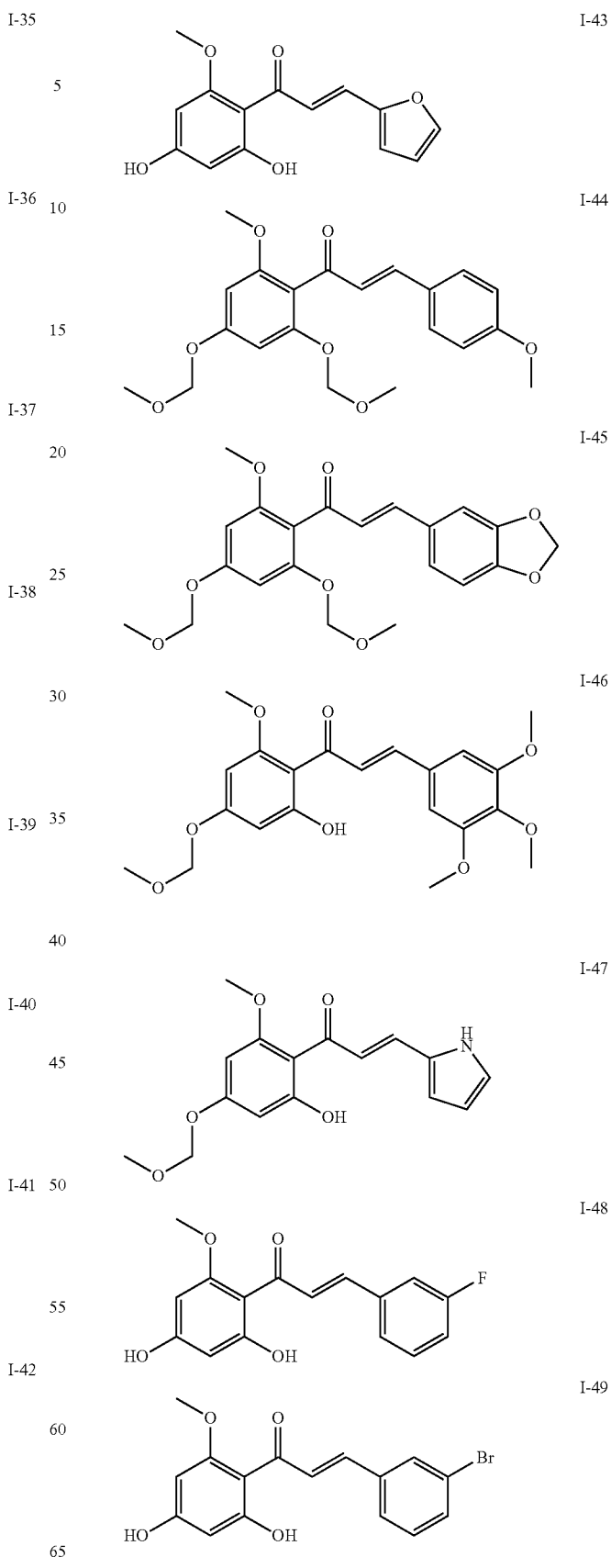

In some embodiments, Formula (I) excludes at least one of the following compounds:

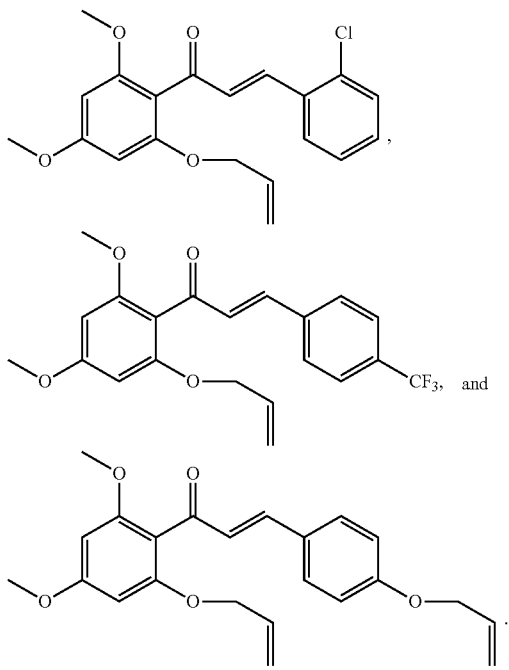

In some embodiments, the synthesis of the Formula (I) compounds can comprise subjecting

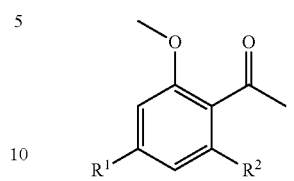

to a condensation reaction, and recovering

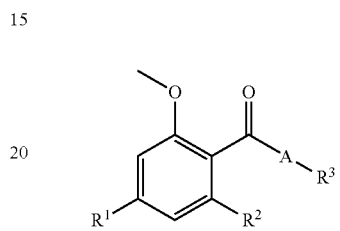

from the reaction mixture.

In some embodiments, the synthesis of the Formula (I) compounds starts with the preparation of related acetophenones, as exemplified in Scheme A.

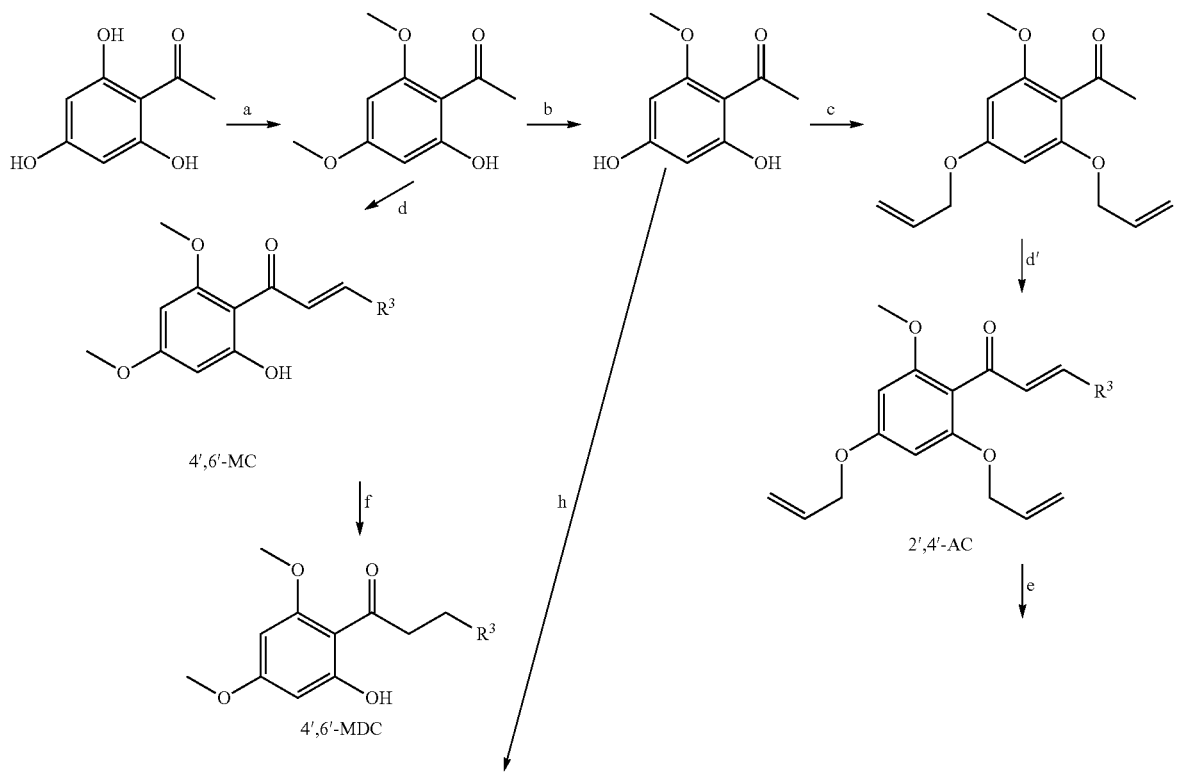

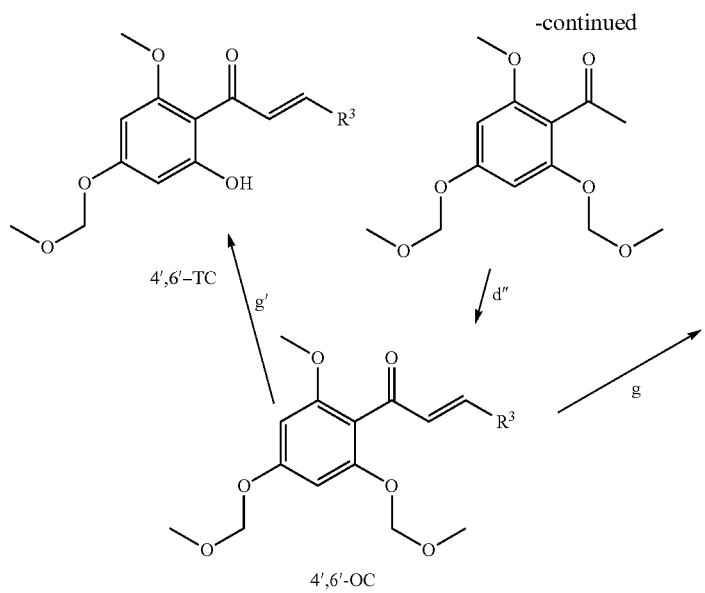

4',6'-TC

4',6'-OC

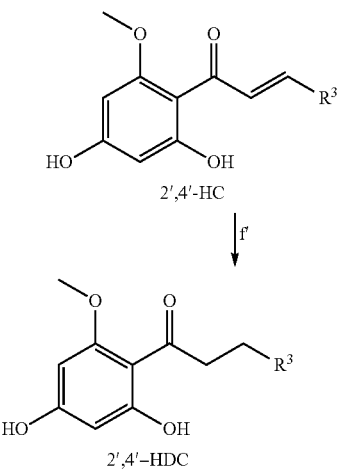

2',4'-HC

2',4'-HDC

In Scheme A, step (a) can be an alkylation reaction, which can occur, for example, by combining a substituted acetophenone with $(CH_3)_2SO_4$, $K_2CO_3$, and $(CH_3)_2CO$ at about 65° C. for about 6 h. Step (b) can be a dealkylation reaction, which can occur, for example, by combining the product of (a) with $AlCl_3$ and benzene, and refluxing for about 1 hour. Step (c) can be a protection (allylation) reaction, which can occur by combining the product of step (b) allyl bromide, $K_2CO_3$ and DMF at room temperature (e.g., about 25° C.) overnight. Steps (d), (d'), and (d") can be condensation reactions (e.g., Claisen-Schmidt aldol condensation) and can have the same or different conditions (using for example different hydroxyl bases). For example, the products of (a), (c), or (h) can be combined with an aromatic aldehyde, KOH, $H_2O$, $CH_3OH$ at room temperature (e.g., about 25° C.) for from about 1 h to about 48 h. Step (e) can be a deprotection (dealkylation) reaction to provide a protection group removal step, which can occur by combining the product of (d') with catalytic $Pd(PPh_3)_4$ in $K_2CO_3$ and MeOH at about 60° C. for about 1 h. Steps (f) and (f') can be reducing steps and can be the same or different. For example, the product of (d) or (e) can be combined with catalytic Pd/C 5%, $H_2$ gas at about 250 psi and EtOAc at room temperature (e.g., about 25° C.) for about 1.5 h. Steps (g) and (g') can be a deprotection or dealkylation reaction and can be the same or different. For example, the product of (d") can be refluxed with about 3N HCl in methanol for about 30 min. Step (h) can be an alkylation or protection reaction. For example, the product of step (b) can be refluxed with $K_2CO_3$, $(CH_3)_2CO$, $CH_3OCH_2Cl$ for about 3 hours. Products of steps (d), (d'), (d"), (e), (f), (f'), (g), and (g') can include compounds of formula (I). Of course, conditions (such temperatures, times, solvents, etc.) can be varied to provide optimized or varied outcomes (such as product yields).

In some embodiments Scheme A can include reaction sequences as follows: Initially, 2,4,6-trihydroxyacetophenone is transformed into 2,4-dihydroxy-6-methoxyacetophenone using dimethyl sulphate as methylating agent. Then, the methyl group on the para-methoxy position of the acetophenone is cleaved using $AlCl_3$, to obtain 2,4-dihydroxy-6-methoxyacetophenone, which is protected using allyl bromide to give 2,4-allyloxy-6-methoxylacetophenone. Claisen-Schmidt aldol condensation of acetophenone with the corresponding aromatic aldehyde in the presence of aqueous KOH, gives a chalcone product. After a mild deprotection procedure to remove the allyl-protecting groups, using $Pd(PPh_3)_4$ and $K_2CO_3$, the resulting 2'4'-dihydroxy-6-methoxy chalcones were finally reduced to produce the corresponding dihydrochalcones.

In Scheme A and when discussed below, 2',4'-AC include some 2',4'-diallyloxy-6'-methoxychalcones; 2',4'-HC include some 2',4'-dihydroxy-6'-methoxychalcones; 2',4'-HDC include some 2',4'-dihydroxy-6'-methoxy-dihydrochalcones; 4',6'-MC include some 4',6'-dimethoxy-2'-hydroxychalcones; 4',6'-MDC include some 4',6'-dimethoxy-2'-hydroxydihydrochalcones; 4',6'-TC include some 2'-hydroxy-4'-methoxymethyl-6'-methoxychalcones; and 4',6'-OC include some 2',4'-dimethoxymethyl-6'-methoxychalcones.

SCHEME B

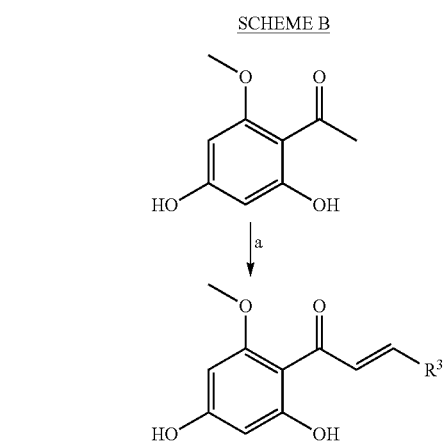

Scheme B demonstrates another strategy for synthesizing compounds of formula (I). This one pot synthesis can include combining the reactant with $K_2CO_3$, MOMCl (methoxymethyl chloride), and methanol at room temperature (e.g., about 25° C.) for about 2 hours. An aldehyde is added to the solution and combined for about 2 hours at room temperature (e.g., about 25° C.). A protonation workup, using an acid solution, occurs for from about 2 to about 4 hours, to remove the methoxymethyl protecting group. Of course, conditions (such temperatures, times, solvents, etc.) can be varied to provide optimized or varied outcomes (such as product yields).

The compounds of the present invention can include Formula (II) compounds such as

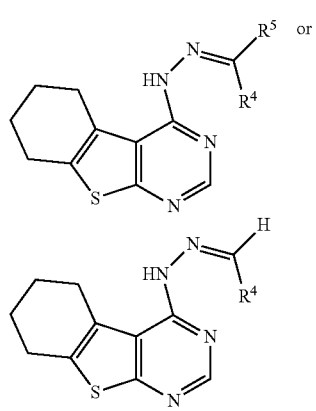

R⁴ and R⁵ can be the same or different.

R⁴ and R⁵ can be H, methyl, ethyl, propyl, isopropyl, butyl, sec-butyl, or t-butyl.

R⁴ and R⁵ can be a substituted or unsubstituted four-, five-, six-, or seven-member ring that may include one or more heteroatoms in the ring. Embodiments include rings that have, for example, one, two, three, four, five, or six substitutions. The ring can be conjugated, aromatic, unsaturated, or saturated. When the rings include heteroatoms, these heterocycles can have 1, 2, 3, or 4 heteroatoms (such as N, S, or O), which can be the same or different for a given ring. In some embodiments, R⁴ or R⁵ can be a substituted or unsubstituted phenyl, naphthyl, furan, pyridine, or pyrrole. Substitutions can include, but are not limited to alkoxy (such as methoxy, ethoxy, or propoxy), hydroxyl, amine, amide, halogens (e.g., F, Cl, or Br), nitro, allyloxy, alkyloxyalkyl (such as methoxymethyl), alkyl (such as methyl, ethyl, or propyl), substituted alkyl (e.g., tri-halogenated methyl or trifluoromethyl).

In some embodiments, R⁴ and R⁵ also include the rings (as just described) and a link to the core structure. The link can be a bivalent, substituted or unsubstituted, branched or unbranched alkane or alkene. In some instances, the link is a mixture of saturated and unsaturated hydrocarbon groups. In some embodiments, the link can be,

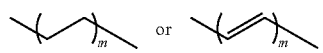

where m can be 1, 2, 3, or 4. In some instances, the link is —CH₂CH₂—, —CH₂CH₂CH₂CH₂—, —CHCH—, or —CHCHCHCH—. In some embodiments, R⁴ is a cinnamyl group.

R⁴ or R⁵ can also be substituted with moieties that are attached at two ring positions to create a fused ring system such as alkylenedioxy (e.g., methylenedioxy (i.e., —OCH₂O)), naphthyl (e.g., 1-naphthyl or 2-naphthyl), benzofuranyl, indolyl, or quinolyl.

In some instances, R⁵, R⁴, or both, are hydrogen.

R⁴ and R⁵ can be the same or different and can be:

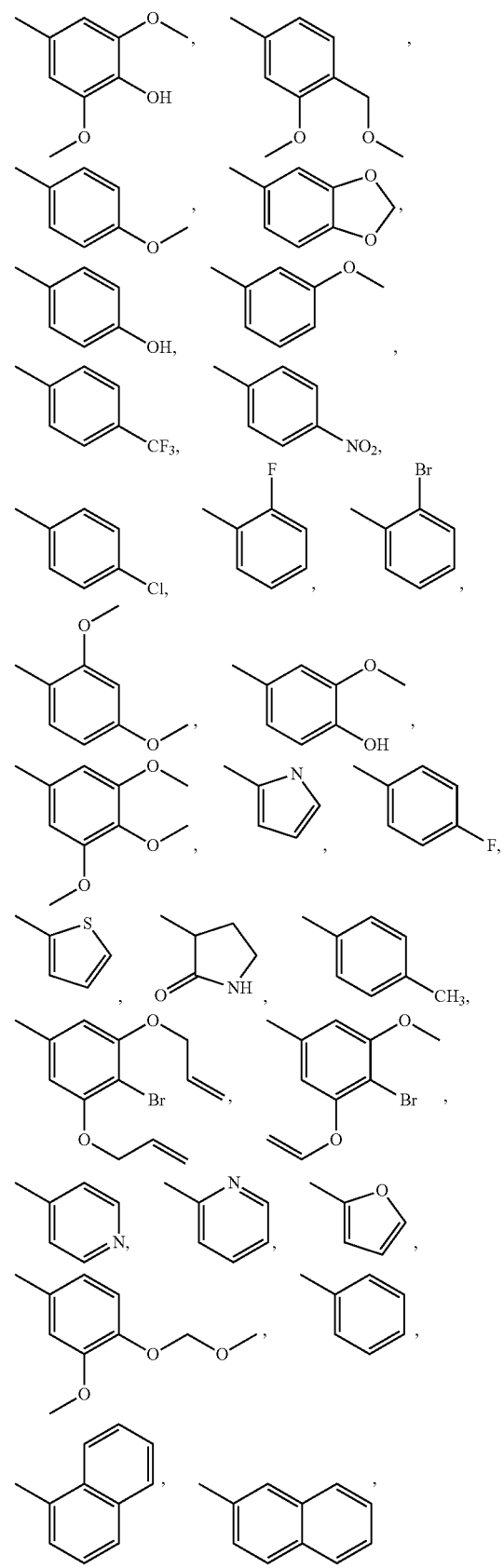

-continued

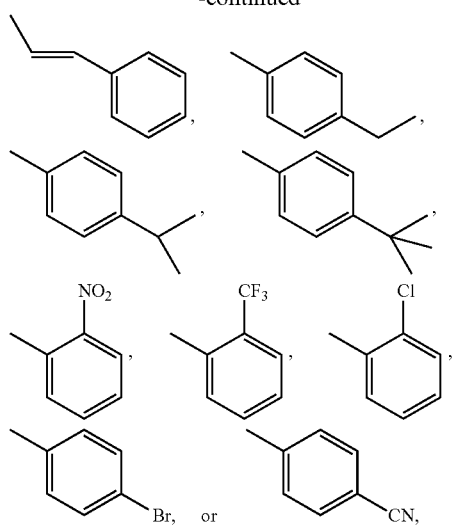

In some embodiments, R⁴ and R⁵ can be selected according to (i) or (ii), as follows:

(i) $R^4$=methyl and $R^5$=phenyl; $R^4$=$R^5$=methyl; $R^4$=$R^5$=ethyl; or $R^4$=$R^5$=phenyl, or (ii) at least one of $R^4$ and $R^5$ is selected from the group consisting of:

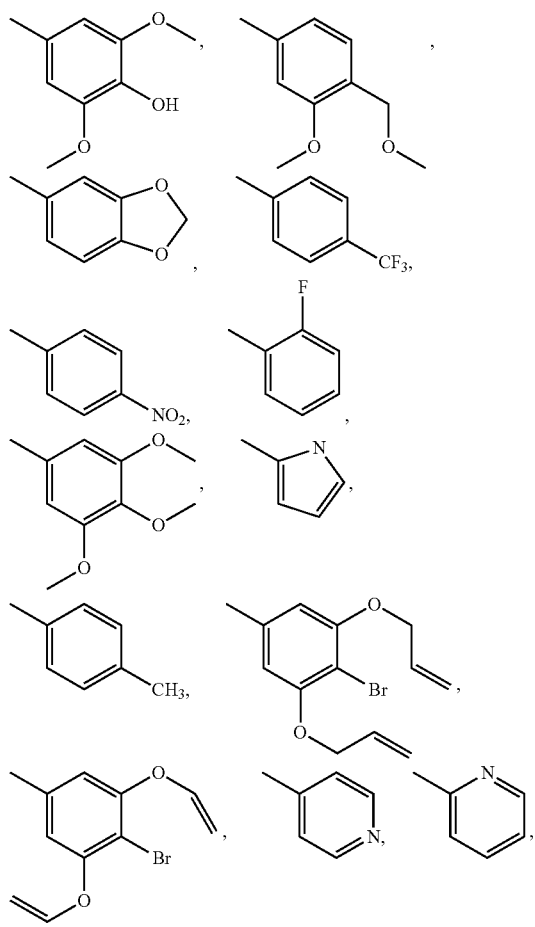

-continued

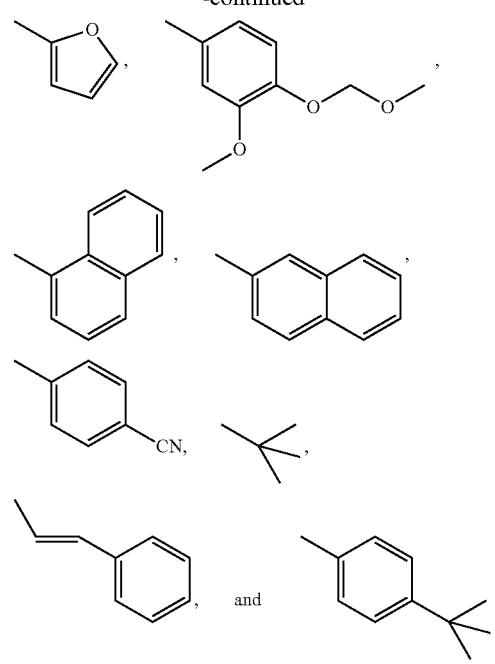

In some embodiments, Formula (II) can be (with molecular formulas and calculated molecular weights):

II-01

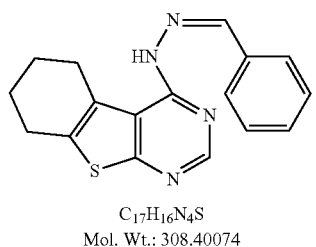

$C_{17}H_{16}N_4S$
Mol. Wt.: 308.40074

II-02

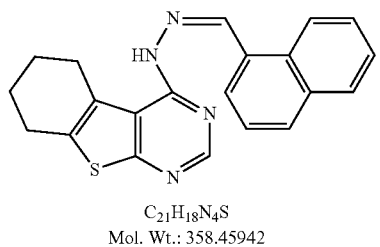

$C_{21}H_{18}N_4S$
Mol. Wt.: 358.45942

II-03

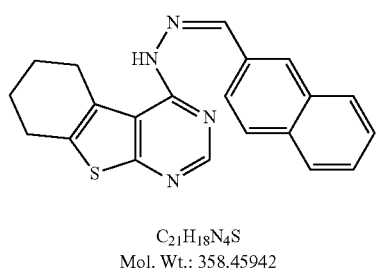

$C_{21}H_{18}N_4S$
Mol. Wt.: 358.45942

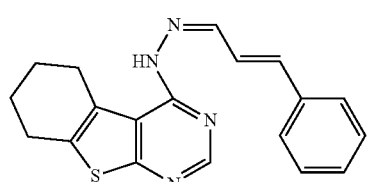
C₁₉H₁₈N₄S
Mol. Wt.: 334.43802
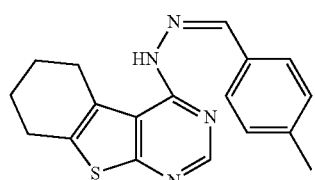
C₁₈H₁₈N₄S
Mol. Wt.: 322.42732
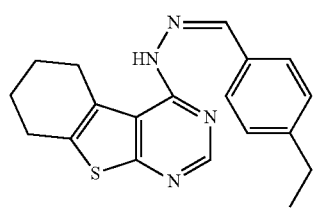
C₁₉H₂₀N₄S
Mol. Wt.: 336.45390
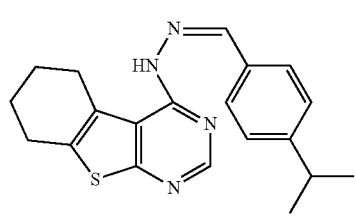
C₂₀H₂₂N₄S
Mol. Wt.: 350.48048
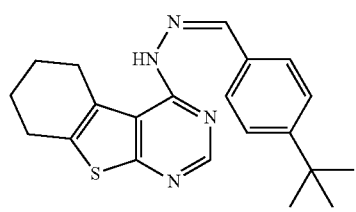
C₂₁H₂₄N₄S
Mol. Wt.: 364.50706
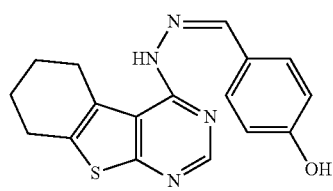
C₁₇H₁₆N₄OS
Mol. Wt.: 324.40014
II-04
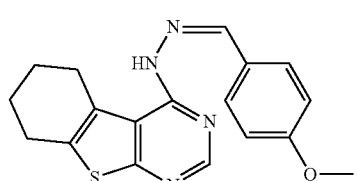
C₁₈H₁₈N₄OS
Mol. Wt.: 338.42672
II-05
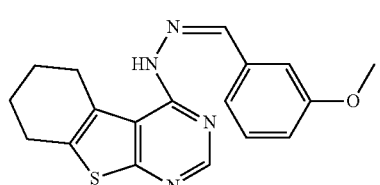
C₁₈H₁₈N₄OS
Mol. Wt.: 338.42672
II-06
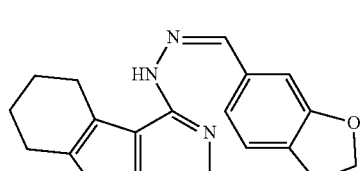
C₁₈H₁₆N₄O₂S
Mol. Wt.: 352.41024
II-07
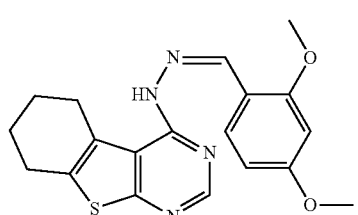
C₁₉H₂₀N₄O₂S
Mol. Wt.: 368.45270
II-08
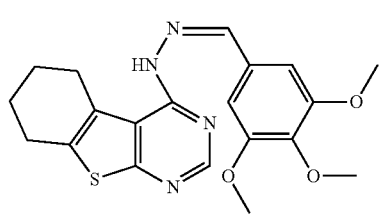
C₂₀H₂₂N₄O₃S
Mol. Wt.: 398.47868
II-09
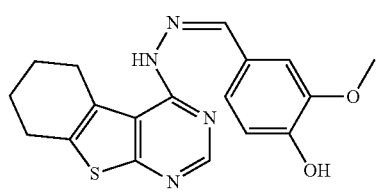
C₁₈H₁₈N₄O₂S
Mol. Wt.: 354.42612
II-10
II-11
II-12
II-13
II-14
II-15

-continued
II-16
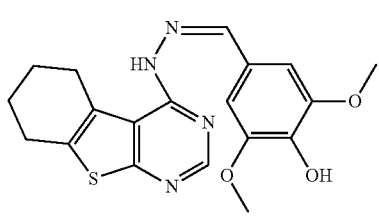
C$_{19}$H$_{20}$N$_4$O$_3$S
Mol. Wt.: 384.45210
II-17
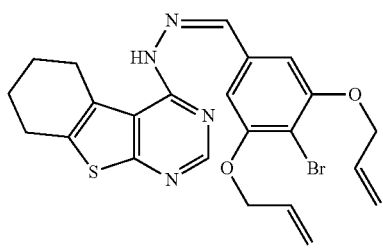
C$_{23}$H$_{23}$BrN$_4$O$_2$S
Mol. Wt.: 499.42332
II-18
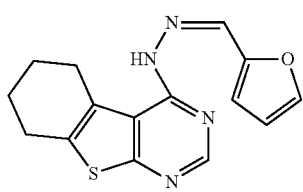
C$_{15}$H$_{14}$N$_4$OS
Mol. Wt.: 298.36286
II-19
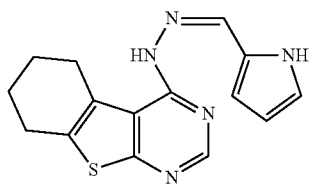
C$_{15}$H$_{15}$N$_5$S
Mol. Wt.: 297.37810
II-20
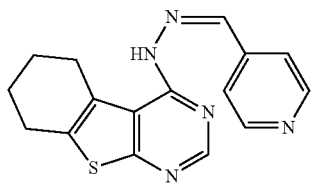
C$_{16}$H$_{15}$N$_5$S
Mol. Wt.: 309.38880
II-21
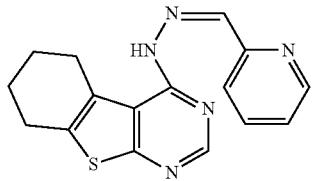
C$_{16}$H$_{15}$N$_5$S
Mol. Wt.: 309.38880
-continued
II-22
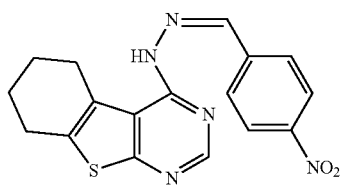
C$_{17}$H$_{15}$N$_5$O$_2$S
Mol. Wt.: 353.39830
II-23
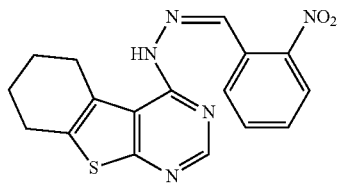
C$_{17}$H$_{15}$N$_5$O$_2$S
Mol. Wt.: 353.39830
II-24
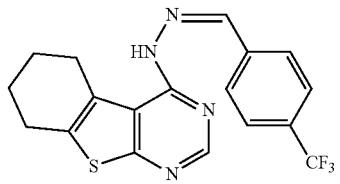
C$_{18}$H$_{15}$F$_3$N$_4$S
Mol. Wt.: 376.39871
II-25
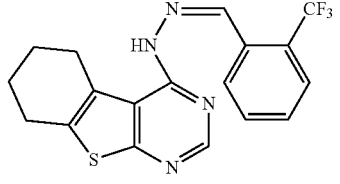
C$_{18}$H$_{15}$F$_3$N$_4$S
Mol. Wt.: 376.39871
II-26
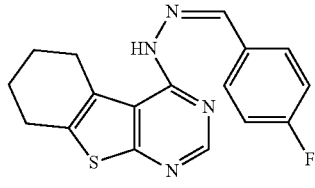
C$_{17}$H$_{15}$FN$_4$S
Mol. Wt.: 326.39120
II-27
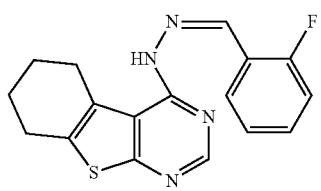
C$_{17}$H$_{15}$FN$_4$S
Mol. Wt.: 326.39120

-continued

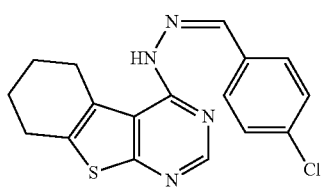

C$_{17}$H$_{15}$ClN$_4$S
Mol. Wt.: 342.84580

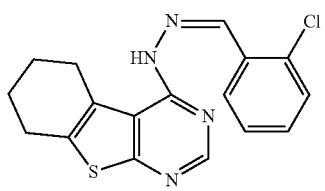

C$_{17}$H$_{15}$ClN$_4$S
Mol. Wt.: 342.84580

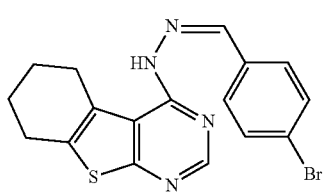

C$_{17}$H$_{15}$BrN$_4$S
Mol. Wt.: 387.29680

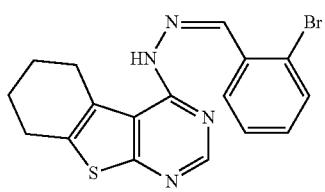

C$_{17}$H$_{15}$BrN$_4$S
Mol. Wt.: 387.29680

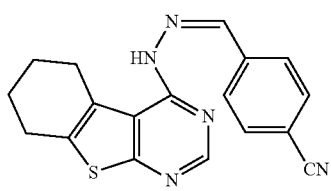

C$_{18}$H$_{15}$N$_5$S
Mol. Wt.: 333.41020

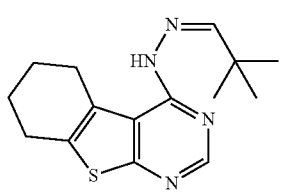

C$_{15}$H$_{20}$N$_4$S
Mol. Wt.: 288.41110

-continued

II-28

II-29

II-30

II-31

II-32

II-36

II-44

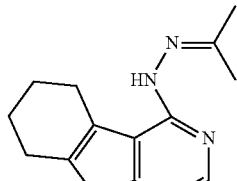

C$_{13}$H$_{16}$N$_4$S
Mol. Wt.: 260.35794

II-47

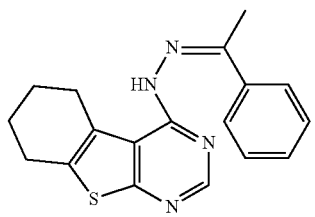

C$_{18}$H$_{18}$N$_4$S
Mol. Wt.: 322.42732

II-48

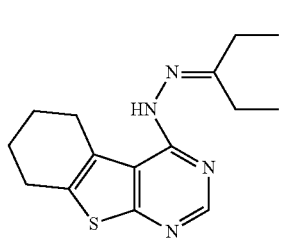

C$_{15}$H$_{20}$N$_4$S
Mol. Wt.: 288.41110

II-49

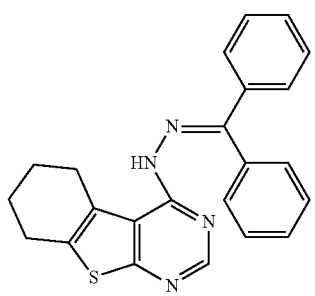

C$_{23}$H$_{20}$N$_4$S
Mol. Wt.: 384.49670

Some compounds of Formula (II) can be synthesized, in some embodiments, as summarized in Scheme C, below. In step (a), a Gewald reaction can be used to prepare the thiol ethyl ester by, for example, combining the reactants (and in some instance refluxing) with S$_8$, a cyclic or alkyl ketone, Et$_2$NH (or any other secondary amine), and ethanol for about 30 minutes to about 2 hours. In step (b), the product of step (a) is treated using a condensation reaction. For example, the step (a) product is combined with a formamide to make the corresponding pyrimidinone. In step (c), the product of step (b) is treated to provide a leaving group for step (d)'s nucleophilic displacement reaction. For example, step (c) can be a chlorination reaction such as refluxing with POCl$_3$ for about 3 hours to about 6 hours. In step (d), the nucleophilic displacement reaction can occur by refluxing with hydrazine and ethanol for about 5 hours. For step (e), the product of step (d)

can be reacted (via a condensation reaction) to form a Schiff base with the corresponding ketone or aldehyde by, for example, refluxing the step (d) product with methanol or ethanol and the corresponding ketone or aldehyde for about 2 hours to about 24 hours (e.g., about 4 hours). Of course, conditions (such temperatures, times, solvents, etc. . . . ) can be varied to provide optimized or varied outcomes (such as product yields).

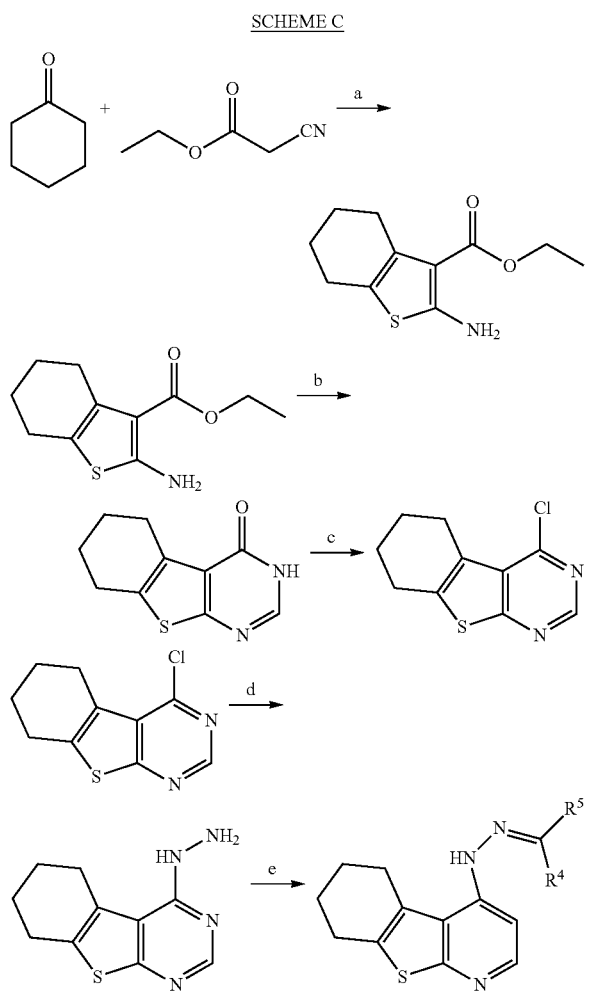

SCHEME C

The compounds of Formula (I) and Formula (II) can be administered to animals by any number of administration routes or formulations. The compounds can also be used to treat animals for a variety of diseases. Animals include but are not limited to canine, bovine, porcine, avian, mammalian, and human.

Diseases that can be treated or cured using the compounds include, but are not limited to Leishmaniasis, Chagas disease, Cancer, diseases related to *Helicobacter* (e.g., gastric ulcer), tuberculosis, Malaria, helminth infectious diseases, African sleeping sickness, onchocerciasis, blinding trachoma, buruli ulcer, Cholera, Dengue, Dracunculiasis (guinea worm disease), Fascioliasis, Leprosy, yaws, lymphatic filariasis, and schistosomiasis. Moreover, the compounds can have many disease state-effects including but not limited to antimicrobial, anti-inflammatory, antibacterial, antiprotozoan, antifungal, anti-cancer, antiviral, immunomodulatory, immunosuppressive, and antineoplastic effects. In some instances, the compounds can modulate (e.g., disrupt) membrane dynamics of the Golgi apparatus of the parasite. In some instances, the compounds can be used to inhibit an infecting organism's enzymatic pathway and the animal being treated is minimally affected because it does not have the inhibited enzymatic pathway.

The route of administration of the compounds may be of any suitable route such as that which provides a concentration in the blood corresponding to a therapeutic concentration. Administration routes that can be used, but are not limited to the oral route, the parenteral route, the cutaneous route, the nasal route, the rectal route, the vaginal route and the ocular route. The choice of administration route can depend on the compound identity, such as the physical chemical properties of the compound, as well as the age and weight of the animal, the particular disease, and the severity of the disease. For example, Leishmaniasis treatment can use a cream, ointment, or oil. Treatment for Tuberculosis can include administration by intravenous delivery, by pill or by cutaneous injection. Of course, combinations of administration routes can be administered, as desired.

The compounds of Formula (I) and Formula (II) can be part of a pharmaceutical composition and can be in an amount from about 1% to about 95% by weight of the total composition (or from about 10% to about 90%, or from about 25% to about 75%). The composition can be presented in a dosage form which is suitable for the oral, parenteral, rectal, cutaneous, nasal, vaginal, or ocular administration route. The composition can be of the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

Pharmaceutical compositions can be formulated to release the active compound substantially immediately upon the administration or any substantially predetermined time or time after administration. Such formulations can include, for example, controlled release formulations such as various controlled release compositions and coatings. Such formulations also include pro-drug principles, such as converting the active drug substance into an inactive derivative; when the pro-drug is administered to the organism, the organism converts the pro-drug to the active drug (e.g., by an enzymatic or non-enzymatic process) so the active drug can exert its therapeutic effect.

Other formulations include those incorporating the drug (or control release formulation) into food, food stuffs, feed, or drink.

The compounds of Formula (I) and Formula (II) can be in the form of salts, optical and geometric isomers, and salts of isomers. Also, the compounds can be in various forms, such as uncharged molecules, components of molecular complexes, or non-irritating pharmacologically acceptable salts, e.g. the hydrochloride, hydrobromide, sulphate, phosphate, nitrate, borate, acetate, maleate, tartrate, salicylate, etc. For acidic compounds, salts include metals, amines, or organic cations (e.g. quaternary ammonium). Furthermore, simple derivatives of the compounds (such as ethers, esters, amides, etc.) which have desirable retention and release characteristics but which are easily hydrolyzed by body pH, enzymes, etc., can be employed.

In some embodiments, certain properties of the compounds may help determine their desirability and may influence experimental or therapeutic properties. For example, the molecular weight of the compounds can be from about 175 to about 1000. For Formula (I) compounds the range of molecular weights can be from about 250 to about 750. For Formula (II) compounds the range of molecular weights can be from about 200 to about 600.

Other properties include the ability of the compound to selectively inhibit an undesired microorganism compared to a desired animal cell, as provided by the Selectivity Index (SI) (defined as that ratio of $IC_{50}$ for a desired cell (e.g. animal cell) to the $IC_{50}$ for an undesired cell (e.g., microorganism)). SI can be about 2, about 5, about 10, about 20, about 50, about 100, about 150, about 200, about 250, about 300, about 400, and about 500. SI can, for example, be from about 2 to about 30, from about 5 to about 25, from about 15 to about 25, from about 2 to about 250, from about 10 to about 250, from about 2 to about 500, from about 10 to about 500, from about 15 to about 250, from about 10 to about 100, or from about 15 to about 100. The parasitic cells can be a pathogenic microorganism (e.g., Prokaryotes, Eukaryotes, or Protists) including, for example, bacteria, mycobacterium, parasite, virus, worms, or fungi. The animal cells can be, for example, macrophage cells, VERO cells or any animal tissue cell (e.g., skin, heart, intestine cell). In some instances, the pathogenic microorganism is a parasite (e.g., *Trypanosoma cruzi* or *Leishmania amazonensis*) and the animal cell is a VERO cell or a macrophage cell. Of course, the parasites may be in the promastigote or amastigote morphological form. In some instances, the pathogenic microorganism is a mycobacterium (e.g., *M. tuberculosis*) and the animal cell is a VERO cell or a macrophage cell.

Other properties include the ability of the compound to reduce the parasite burden of an animal. The parasites can be, for example, *Trypanosoma cruzi* or *Leishmania amazonensis*. The animal can be a mammal, such as a mouse or a human. The reduction in parasite burden can be the result of daily treatments (e.g., 3, 4, 5, 6, 7, or 8 treatments) over many weeks (e.g., 4, 5, 6, 7, 8, 9, or 10 weeks) at a fixed or variable dosage of the compound (e.g., 2, 3, 4, 5, 6, 7, 8, 9, or 10 mg/kg/day). The percent reduction in parasite burden can be about 10%, about 20%, about 50%, about 60%, about 75%, about 85%, about 90%, about 95%, or about 100%. The percent reduction in parasite burden can be at least about 5%, at least about 10%, or at least about 25%. The percent reduction in parasite burden can be from about 5% to about 95%, from about 10% to about 95%, from about 25% to about 95%, from about 5% to about 75%, from about 10% to about 75%, or from about 25% to about 75%.

Variations of the structural components of the compounds can influence the activity (e.g., on cell growth in vitro), selectivity (e.g., as provided by the Selectivity Index (SI), which is defined as that ratio of $IC_{50}$ for a desired animal cell to the $IC_{50}$ for an undesired microorganism), or therapeutic effect of the compound. For example, cytotoxicities of Formula (I) compounds with the α,β unsaturated carbonyl group can be higher than their dihydro counterparts lacking the α,β unsaturated carbonyl group; the latter can sometimes react with nucleophiles such as glutathione (GSH). In some embodiments, the activity or selectivity of Formula (I) compounds can be influenced by the planarity of the Formula (I) compound's phenyl ring relative to the adjacent ketone; this planarity can be affected by substituents on the phenyl ring, such as in the ortho positions. In other embodiments, the electron withdrawing or donating influence of $R^3$ can also alter the activity and selectivity. In some instances, an electron withdrawing $R^3$ can provide high activity. In some instances, an electron donating $R^3$ can provide a high selectivity index (e.g., at least 5 or at least 7 or at least 9 or at least 12). The inclusion of two or more double bonds in A can produce a loss of activity. Variation in the heterocyclic nature (e.g., choice of which hetero atoms are in the heterocycle) of $R^3$ can also produce changes in the activity and selectivity index.

Other properties that could be useful include those calculated for the ADME study such as the topological polar surface area and the number of Lipinski's rule violations. A computational study can be used to predict ADME (absorption, distribution, metabolism, and elimination) which can aid in drug discovery. In such an analysis, topological polar surface area (TPSA) can be a good indicator of compound absorbance in the intestines, Caco-2 monolayers penetration, and blood-brain barrier crossing. TPSA can be used to calculate the percentage of absorption (% ABS) according to the equation: % ABS=109-0.345×TPSA, as reported by Zhao et al. (Zhao et al., *Rate-limited steps of human oral absorption and QSAR studies*, Pharm. Res. 2002, Vol. 19, pp. 1446-1457). In addition, the number of rotatable bonds (n-ROTB), and Lipinski's rule of five, can also be calculated. From one or more of these parameters, accurate predictions can sometimes be made regarding the potential utility to compounds for therapy.

EXAMPLES

Embodiments of Some Syntheses of Formula (I) Compounds

Scheme 1. Strategy for the synthesis of some compounds.

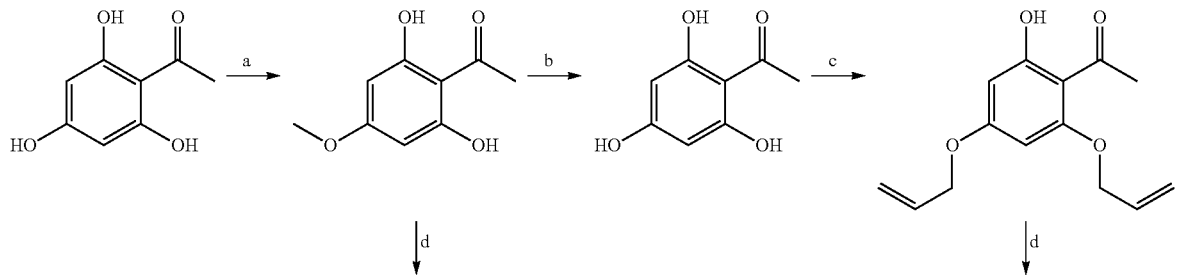

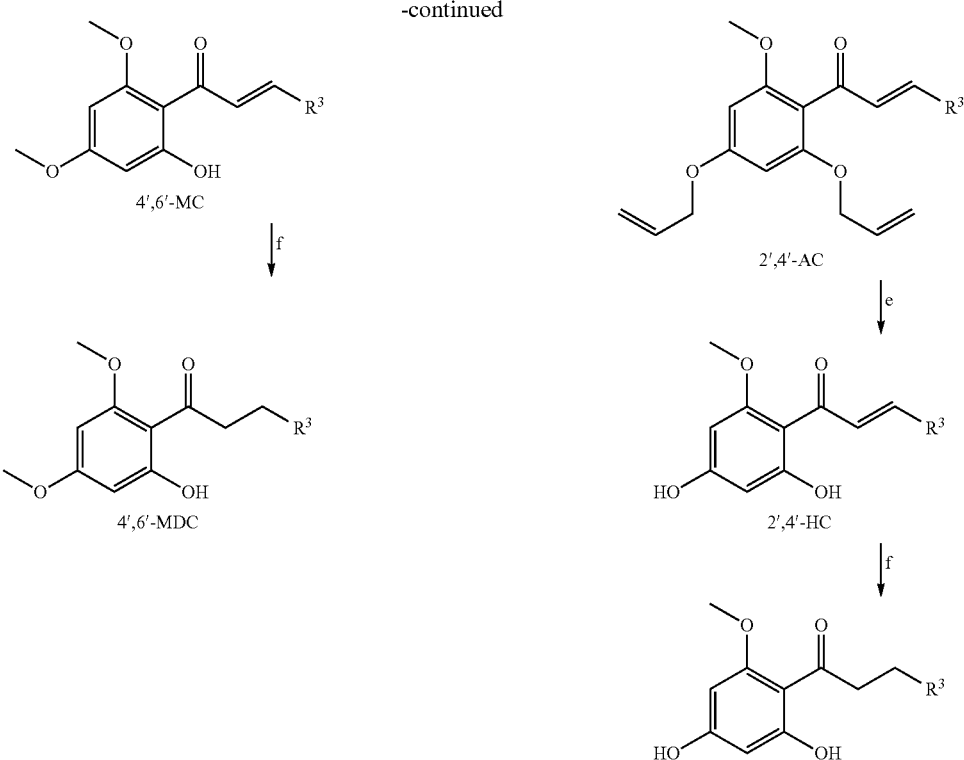

Reagents and conditions in Scheme 1 were: (a) K₂CO₃, (CH₃)₂SO₄, (CH₃)₂CO, 65° C., 6 h. (b) AlCl₃, benzene, reflux, 1 h. (c) K₂CO₃, allyl bromide, DMF, room temperature (e.g., 25° C.), overnight. (d) Claisen-Schmidt aldol condensation of an acetophenone with an aromatic aldehyde, KOH, H₂O, CH₃OH, room temperature (e.g., 25° C.), 1-48 h. (e) K₂CO₃, catalytic Pd(PPh₃)₄, MeOH, 60° C., 1 h. (f) catalytic Pd/C 5%, H₂ gas, 250 psi, EtOAc, room temperature (e.g., 25° C.), 1.5 h.

Example Syntheses of Some Formula (I) Compounds, Such as Acetophenone-Related Compounds.

To a refluxing solution of 2,4,6-trihydroacetophenone-monohydrate (10 g, 53.7 mmol) and K₂CO₃ (15 g, 108.7 mmol) in acetone (150 mL), (CH₃)₂SO₄ was added at three hour intervals (3×3.5 mL, 40.0 mmol). The solution was filtered and the solvent was evaporated to afford 2,4-dimethoxy-6-hydroxyacetophenone as a yellow solid (98%). To obtain 2,4-dihydroxy-6-methoxyacetophenone, anhydrous AlCl₃ (11.0 g, 82.5 mmol) and 2,4-dimethoxy-6-hydroxyacetophenone (11.0 g, 56.1 mmol) were suspended in chlorobenzene (133 mL) and refluxed for 1 h. After cooling and evaporating of the solvent, an ice-cold H₂O—HCl (1:1, 290 mL) solution was added to the residue and sonicated until the white precipitate seemed homogeneous. The solution was filtered and the solid was dissolved in EtOAc (200 mL) and extracted with an aqueous solution of NaOH (10%, 3×200 mL). The aqueous portions were mixed and neutralized with HCl (conc., 40 mL) to finally be extracted with EtOAc (2×250 mL) and recrystallized from the same solvent (44.1%). 2,4-diallyloxy-6-methoxyacetophenone, was prepared by mixing 2,4-dihydroxy-6-methoxyacetophenone (5.8 g, 10.0 mmol), K₂CO₃ (21.8 g, 50.0 mmol) and allylbromide (11.0 mL, 40 mmol) in DMF (100 mL). After stiffing for 18 hours, the mixture was dissolved in deionized water (100 mL) and extracted with diethyl ether (3×75 mL). The organic layers were pooled and extracted with deionized water (3×50 mL). Finally, the organic phases were combined and dried to be subjected to column chromatography using hexanes-EtOAc step gradient (40:1 to 5:1, colorless oil, 85.0%).

Example Syntheses of Some Formula (I) Compounds, Such as Chalcone- and Dihydrochalcone-Related Compounds.

To prepare chalcone-related compounds, the corresponding acetophenone (1.2 mmol), aromatic aldehyde (1.4 mmol), KOH (1.5 g, 26.7 mmol), H₂O (1.5 mL) and CH₃OH (3.0 mL) were stirred at room temperature (e.g., 25° C.) for 1 to 48 hours. Deionized water (50 mL) was added and the solution was extracted with EtOAc (2×30 mL), the organic layer was dried over MgSO₄ and evaporated. The crude extract was subjected to column chromatography using hexanes-EtOAc gradient (10:1 to 1:1). To obtain 2,4-dihydroxy-6-methoxychalcone, the appropriate 2,4-diallyloxy-6-methoxychalcone (0.25 mmol) and Pd(Ph₃P)₄ (1 mmol %) were dissolved in CH₃OH (3 mL), after 1 min of sonication, K₂CO₃ (6 eq) was added to the mixture and flushed with argon gas for 3 min. The solution was stirred for 1 h at 60° C. and then it was poured over a solution of HCl (2N, 20 mL). The aqueous solution was extracted with EtOAc (2×20 mL) and the organic phase was dried over MgSO₄ and evaporated. The orange residue was purified by column chromatography using Hexanes-EtOAc step gradients (6:1 to 1:2). 2,4-dihydroxy-6-methoxydihydrochalcones, were obtained by mixing the appropriate chalcone (1.5 mmol) with Pd/C 5% (0.1 eq) in EtOAc (10 mL) and stiffing the solution in a Parr flask under 250 psi of H₂ gas at room temperature (e.g., 25° C.) for 1.5 hour. Then the solvent was evaporated and the residue purified by column chromatography using Hexanes-EtOAc step gradients (20:1 to 4:1).

Compound Data:

¹H and ¹³C NMR spectra were recorded at 500 and 125 MHz respectively, using CDCl₃ or CDCl₃/CD₃OD as a solvent on a Varian Inova 500. The chemical shifts are reported in ppm values relative to $CHCl_3$ (7.27 ppm for $^1H$ NMR and 77.0 ppm for $^{13}C$ NMR). Coupling constants (J) are reported in hertz (Hz). Melting points were measured on a Thomas Hoover capillary melting point apparatus and are uncorrected. All air and/or moisture sensitive reactions were carried out under argon atmosphere. Elemental analysis was performed at Atlantic Microlab, Inc., Norcross, Ga. Column chromatography was carried out over Silicycle silica gel (230-400 mesh). Reactions and fractions obtained from column chromatography were monitored on Merck silica gel 60 F254 aluminum sheets. TLC spots were visualized by inspection of plates under UV light (254 and 365 nm) and after submersion in 5% sulphuric acid or in 4% phosphomolybdic acid and heating (110° C.). All commercial reagents were obtained either from Aldrich, Acros or Alfa Aesar and used without any further purification. 3,5-Bisallyloxy-4-bromobenzaldehyde was available from our laboratory.

The data for each compound below is: Aspect (melting point); isolated yield; $^1H$, $^{13}C$ NMR ($CDCl_3$ or $CDCl_3/CD_3OD$); and Elemental Analysis.

(2E)-1-(2-Hydroxy-4,6-dimethoxyphenyl)-3-(4-methoxyphenyl)-2-propen-1-one (I-01)

Yellow solid (mp: 112° C.); 70.1%; $^1H$ NMR: δ 7.78 (d, J=16.5 Hz, 1H); 7.77 (d, J=16 Hz, 1H); 7.58 (d, J=8.5 Hz, 2H); 6.94 (d, J=8.5 Hz, 2H); 6.12 (d, J=2 Hz, 1H); 5.97 (d, J=2.5 Hz, 1H); 3.93 (s, 3H); 3.86 (s, 3H); 3.84 (s, 3H). $^{13}C$ NMR: δ 192.8, 168.6, 166.3, 162.7, 161.6, 142.7, 130.4, 130.4, 128.6, 125.4, 114.6, 114.6, 106.6, 94.1, 91.5, 56.1, 55.8, 55.6 Anal. ($C_{18}H_{18}O_5$) C: calcd, 68.78 found, 68.99; H: calcd, 5.77 found, 5.82.

(2E)-3-(1,3-Benzodioxol-5-yl)-1-(2-hydroxy-4,6-dimethoxyphenyl)-2-propen-1-one (I-02)

Yellow solid (mp: 163° C.); 16.0%; $^1H$ NMR: δ 7.78 (d, J=15.5 Hz, 1H); 7.73 (d, J=15.5 Hz, 1H); 7.13 (s, 1H); 7.10 (d, J=8 Hz, 1H); 6.84 (d, J=8 Hz, 1H); 6.12 (d, J=2.5 Hz, 1H); 6.03 (s, 2H); 5.97 (d, J=2 Hz, 1H); 3.93 (s, 3H); 3.85 (s, 3H). $^{13}C$ NMR: δ 192.7, 168.6, 166.3, 162.7, 149.8, 148.5, 142.7, 130.3, 125.8, 125.3, 108.9, 106.8, 106.6, 101.8, 94.1, 91.5, 56.1, 55.8 Anal. ($C_{18}H_{16}O_6$) C: calcd, 65.85 found, 65.82; H: calcd, 4.91 found, 4.86.

1-(2-Hydroxy-4,6-dimethoxyphenyl)-3-(4-methoxyphenyl)-1-propanone (I-03)

White solid (mp: 107° C.); 63.8%; $^1H$ NMR: δ 7.18 (d, J=9 Hz, 2H); 6.86 (d, J=9 Hz, 2H); 6.09 (d, J=2.5 Hz, 1H); 5.94 (d, J=2.5 Hz, 1H); 3.85 (s, 3H); 3.83 (s, 3H); 3.81 (s, 3H); 3.30 (t, J=8 Hz, 2H); 2.95 (t, J=7.5 Hz, 2H). $^{13}C$ NMR: δ 204.8, 167.9, 167.9, 166.2, 166.2, 162.9, 158.1, 133.9, 129.8, 114.1, 105.9, 93.8, 91.1, 55.7, 55.6, 55.4, 46.3, 30.1 Anal. ($C_{18}H_{20}O_5$) C: calcd, 68.34 found, 68.43; H: calcd, 6.71 found, 6.50.

3-(1,3-Benzodioxol-5-yl)-1-(2-hydroxy-4,6-dimethoxyphenyl)-1-propanone (I-04)

White solid (mp: 125° C.); 33.8%; $^1H$ NMR: δ 6.75 (d, J=7.5 Hz, 2H); 6.69 (d, J=8 Hz, 1H); 6.08 (d, J=1.5 Hz, 1H); 5.93 (s, 1H); 5.93 (s, 2H); 3.85 (s, 3H); 3.82 (s, 3H); 3.28 (t, J=8 Hz, 2H); 2.92 (t, J=8 Hz, 2H). $^{13}C$ NMR: δ 204.6, 167.9, 166.2, 162.9, 147.8, 145.9, 135.8, 121.5, 109.2, 108.6, 105.9, 101.1, 93.9, 91.1, 55.8, 55.7, 46.2, 30.6 Anal. ($C_{18}H_{18}O_6$) C: calcd, 56.45 found, 65.45; H: calcd, 5.49 found, 5.46.

(E)-1-(2,4-Dihydroxy-6-methoxyphenyl)-3-(4-methoxyphenyl)-2-propen-1-one (I-05)

Yellow solid (decomposes: 157° C.); 80.4%; $^1H$ NMR: δ 7.73 (d, J=16 Hz, 1H); 7.66 (d, J=15 Hz, 1H); 7.50 (d, J=9 Hz, 2H); 6.87 (d, J=9 Hz, 2H); 5.94 (d, J=2 Hz, 1H); 5.90 (d, J=1.5 Hz, 1H); 3.85 (s, 3H); 3.79 (s, 3H); 3.04 (s, 2H). $^{13}C$ NMR: δ 192.8, 167.3, 164.9, 163.4, 161.5, 142.4, 130.2, 130.2, 128.5, 125.5, 114.5, 114.5, 105.8, 96.4, 91.8, 55.9, 55.5 Anal. ($C_{17}H_{16}O_5$) C: calcd, 67.99 found, 75.32; H: calcd, 5.37 found, 8.39.

(2E)-3-(1,3-Benzodioxol-5-yl)-1-(2,4-dihydroxy-6-methoxyphenyl)-2-propen-1-one (I-06)

Yellow solid (decomposes: 182° C.); 24.1%; $^1H$ NMR: δ 7.63 (d, J=15.5 Hz, 1H); 7.54 (d, J=15.5 Hz, 1H); 6.99 (s, 1H); 6.96 (d, J=8 Hz, 1H); 6.71 (d, J=8 Hz, 1H); 5.90 (s, 2H); 5.89 (d, J=2.5 Hz, 1H); 5.85 (d, J=2 Hz, 1H); 3.87 (s, 2H); 3.80 (s, 3H). $^{13}C$ NMR: δ 192.6, 167.3, 165.0, 163.4, 149.7, 148.4, 142.3, 130.2, 125.8, 125.1, 108.7, 106.6, 105.8, 101.7, 96.4, 91.8, 55.9 Anal. ($C_{17}H_{14}O_6$) C: calcd, 64.97 found, 65.59; H: calcd, 4.40 found, 4.89.

1-(2,4-Dihydroxy-6-methoxyphenyl)-3-(4-methoxyphenyl)-1-propanone (I-07)

White solid (mp: 166° C.); 40.2%; $^1H$ NMR: δ 7.14 (d, J=8.5 Hz, 2H); 6.83 (d, J=8.5 Hz, 2H); 5.96 (d, J=2 Hz, 1H); 5.90 (d, J=2 Hz, 1H); 3.81 (s, 3H); 3.78 (s, 3H); 3.25 (t, J=8 Hz, 2H); 2.91 (t, J=8 Hz, 2H). $^{13}C$ NMR: δ 204.8, 166.8, 166.9, 164.5, 164.3, 163.7, 158.0, 134.0, 129.6, 114.1, 105.4, 96.3, 91.4, 55.8, 55.5, 46.2, 30.2 Anal. ($C_{17}H_{18}O_5$) C: calcd, 67.54 found, 67.77; H: calcd, 6.00 found, 6.20.

(2E)-1-[2-Methoxy-4,6-bis(2-propenyloxy)phenyl]-3-(phenyl)-2-propen-1-one (I-08)

Yellow oil; 63.5%; $^1H$ NMR: δ 7.53 (d, J=3.5 Hz, 2H); 7.37 (m, 4H); 6.99 (d, J=15.5 Hz, 1H); 6.19 (d, J=9 Hz, 2H); 6.08 (m, 1H); 5.92 (m, 1H); 5.46 (d, J=17 Hz, 1H); 5.33 (m, 2H); 5.18 (d, J=11 Hz, 1H); 4.58 (d, J=4 Hz, 2H); 4.52 (d, J=3.5 Hz, 2H); 3.77 (s, 3H). $^{13}C$ NMR: δ 194.3, 161.5, 159.1, 158.0, 144.3, 135.3, 133.1, 132.9, 130.4, 129.3, 129.0, 129.0, 128.6, 128.6, 118.3, 117.6, 112.7, 93.0, 92.1, 69.6, 69.3, 56.2. Anal. ($C_{22}H_{22}O_4$) C: calcd, 75.41 found, 73.69; H: calcd, 6.33 found, 6.33.

(2E)-1-[2-Methoxy-4,6-bis(2-propenyloxy)phenyl]-3-(4-hydroxyphenyl)-2-propen-1-one (I-09)

Yellow oil; 64.9%; $^1H$ NMR: δ 8.09 (s, 1H); 7.37 (m, 3H); 6.86 (m, 3H); 6.16 (d, J=6 Hz, 2H); 6.07 (m, 1H); 5.89 (m, 1H); 5.44 (d, J=17.5 Hz, 1H); 5.32 (m, 2H); 5.16 (d, J=10.5 Hz, 1H); 4.55 (d, J=4 Hz, 2H); 4.49 (d, J=3.5 Hz, 2H); 3.73 (s, 3H). $^{13}C$ NMR: δ 196.0, 161.6, 159.6, 159.0, 158.0, 146.5, 133.1, 132.9, 130.7, 130.7, 126.8, 126.2, 118.4, 117.7, 116.4, 116.4, 112.2, 93.0, 92.1, 69.6, 69.3, 56.1. Anal. ($C_{22}H_{22}O_5$) C: calcd, 72.12 found, 70.82; H: calcd, 6.05 found, 6.12.

(2E)-1-[2-Methoxy-4,6-bis(2-propenyloxy)phenyl]-3-(4-methoxyphenyl)-2-propen-1-one (I-10)

Yellow oil; 72.5%; $^1H$ NMR: δ 7.43 (d, J=8.5 Hz, 2H); 7.32 (d, J=16 Hz, 1H); 6.85 (d, J=15.5 Hz, 1H); 6.83 (d, J=9 Hz, 2H); 6.15 (d, J=7 Hz, 2H); 6.02 (m, 1H); 5.86 (m, 1H); 5.42 (d, J=17 Hz, 1H); 5.28 (m, 2H); 5.12 (d, J=10.5 Hz, 1H); 4.53 (d, J=5 Hz, 2H); 4.61 (d, J=4.5 Hz, 2H); 3.75 (s, 3H); 3.70 (s, 3H). $^{13}$C NMR: δ 194.3, 161.7, 161.4, 158.9, 157.8, 144.3, 133.2, 133.0, 130.2, 130.2, 127.8, 127.2, 118.1, 117.4, 114.5, 114.5, 112.7, 93.0, 92.1, 69.5, 69.2, 56.1, 55.6. Anal. ($C_{23}H_{24}O_5$) C: calcd, 72.61 found, 72.84; H: calcd, 6.36 found, 6.56.

(2E)-1-[2-Methoxy-4,6-bis(2-propenyloxy)phenyl]-3-(3-methoxyphenyl)-2-propen-1-one (I-11)

Yellow oil; 83.7%; $^1$H NMR: δ 7.37 (d, J=16 Hz, 1H); 7.27 (m, 1H); 7.11 (d, J=8 Hz, 1H); 7.05 (s, 1H); 6.97 (d, J=16 Hz, 1H); 6.92 (dd, J=2, 8.5 Hz, 1H); 6.19 (dd, J=2, 9.5 Hz, 2H); 6.07 (m, 1H); 5.92 (m, 1H); 5.45 (dd, J=1.5, 17.5 Hz, 1H); 5.32 (m, 2H); 5.17 (dd, J=1.5, 11 Hz, 1H); 4.57 (d, J=5 Hz, 2H); 4.51 (dd, J=1.5, 3.5 Hz, 2H); 3.82 (s, 3H); 3.77 (s, 3H). $^{13}$C NMR: δ 194.2, 161.6, 160.1, 159.1, 158.0, 144.1, 136.7, 133.1, 132.9, 130.0, 129.6, 121.3, 118.3, 117.6, 116.4, 113.3, 112.6, 93.0, 92.1, 69.6, 69.3, 56.1, 55.6. Anal. ($C_{23}H_{24}O_5$) C: calcd, 72.61 found, 72.73; H: calcd, 6.36 found, 6.48.

(2E)-1-[2-Methoxy-4,6-bis(2-propenyloxy)phenyl]-3-[4-(trifluoromethyl)phenyl]-2-propen-1-one (I-12)

Yellow oil; 46.6%; $^1$H NMR: δ 7.60 (s, 4H); 7.40 (d, J=16 Hz, 1H); 7.04 (d, J=16 Hz, 1H); 6.19 (d, J=8.5 Hz, 2H); 6.05 (m, 1H); 5.90 (m, 1H); 5.44 (dd, J=1, 17 Hz, 1H); 5.33 (m, 2H); 5.17 (dd, J=1.5, 10.5 Hz, 1H); 4.56 (d, J=5 Hz, 2H); 4.51 (d, J=4.5 Hz, 2H); 3.76 (s, 3H). $^{13}$C NMR: δ 193.3, 161.9, 159.3, 158.3, 141.4, 138.8, 133.0, 132.8, 131.5, 131.3, 129.4, 128.6, 128.6, 125.9, 125.9, 118.3, 117.6, 112.3, 93.0, 92.2, 69.6, 69.3, 56.1. Anal. ($C_{23}H_{21}F_3O_4$) C: calcd, 66.02 found, 66.14; H: calcd, 5.06 found, 5.16.

(2E)-1-[2-Methoxy-4,6-bis(2-propenyloxy)phenyl]-3-(4-nitrophenyl)-2-propen-1-one (I-13)

Yellow wax; 64.6%; $^1$H NMR: δ 8.23 (d, J=9 Hz, 2H); 7.67 (d, J=9 Hz, 2H); 7.46 (d, J=16.5 Hz, 1H); 7.10 (d, J=16 Hz, 1H); 6.19 (dd, J=2, 10 Hz, 2H); 6.06 (m, 1H); 5.94 (m, 1H); 5.46 (dd, J=1.5, 17 Hz, 1H); 5.35 (m, 2H); 5.20 (dd, J=1.5, 11 Hz, 1H); 4.58 (dd, J=1.5, 4 Hz, 2H); 4.53 (dd, J=1.5, 3.5 Hz, 2H); 3.79 (s, 3H). $^{13}$C NMR: δ 192.7, 162.1, 159.5, 158.4, 148.5, 141.7, 139.9, 132.9, 132.8, 132.7, 129.0, 129.0, 124.3, 124.3, 118.5, 117.7, 112.2, 93.0, 92.2, 69.7, 69.3, 56.2. Anal. ($C_{22}H_{21}NO_6$) C: calcd, 66.83 found, 65.93; H: calcd, 5.35 found, 5.38.

(2E)-3-(4-Chlorophenyl)-1-[2-methoxy-4,6-bis(2-propenyloxy)phenyl]-2-propen-1-one (I-14)

Yellow oil; 85.0%; $^1$H NMR: δ 7.45 (d, J=8.5 Hz, 2H); 7.36 (d, J=16 Hz, 1H); 7.34 (m, 2H); 6.95 (d, J=16.5 Hz, 1H); 6.18 (dd, J=1.5, 9.5 Hz, 2H); 6.07 (m, 1H); 5.93 (m, 1H); 5.45 (dd, J=1, 17 Hz, 1H); 5.33 (m, 2H); 5.18 (dd, J=0.5, 10.5 Hz, 1H); 4.57 (d, J=5.5 Hz, 2H); 4.51 (d, J=4.5 Hz, 2H); 3.77 (s, 3H). $^{13}$C NMR: δ 193.8, 161.7, 159.2, 158.1, 142.4, 136.2, 133.8, 133.0, 132.9, 129.7, 129.7, 129.7, 129.3, 129.3, 118.4, 117.6, 112.5, 93.0, 92.2, 69.6, 69.3, 56.2. Anal. ($C_{22}H_{21}ClO_4$) C: calcd, 68.66 found, 68.44; H: calcd, 5.50 found, 5.62.

(2E)-3-(2-Fluorophenyl)-1-[2-methoxy-4,6-bis(2-propenyloxy)phenyl]-2-propen-1-one (I-15)

Yellow oil; 83.2%; $^1$H NMR: δ 7.58 (m, 1H); 7.55 (d, J=16.5 Hz, 1H); 7.33 (m, 1H); 7.14 (m, 1H); 7.07 (d, J=16 Hz, 1H); 7.06 (m, 1H); 6.19 (dd, J=1.5, 9.5 Hz, 2H); 6.08 (m, 1H); 5.92 (m, 1H); 5.44 (dd, J=1.5, 17 Hz, 1H); 5.32 (m, 2H); 5.18 (dd, J=1.5, 10.5 Hz, 1H); 4.57 (dd, J=1.5.4 Hz, 2H); 4.52 (d, J=3.5 Hz, 2H); 3.85 (s, 3H). $^{13}$C NMR: δ 194.1, 162.6, 161.7, 160.6, 159.2, 158.1, 136.3, 133.1, 131.8, 131.4, 129.1, 124.6, 123.4, 118.3, 117.6, 116.4, 112.4, 93.0, 92.2, 69.6, 69.3, 56.2. Anal. ($C_{22}H_{21}FO_4$) C: calcd, 71.73 found, 71.68; H: calcd, 5.75 found, 5.78.

(2E)-3-(4-Bromophenyl)-1-[2-methoxy-4,6-bis(2-propenyloxy)phenyl]-2-propen-1-one (I-16)

Yellow oil; 94.3%; $^1$H NMR: δ 7.75 (d, J=16 Hz, 1H); 7.64 (dd, J=1.5, 8 Hz, 1H); 7.58 (d, J=8 Hz, 1H); 7.32 (t, J=7.5 Hz, 1H); 7.21 (m, 1H); 6.89 (d, J=16 Hz, 1H); 6.19 (dd, J=2, 9 Hz, 2H); 6.06 (m, 1H); 5.93 (m, 1H); 5.45 (dd, J=1.5, 17.5 Hz, 1H); 5.33 (m, 2H); 5.18 (dd, J=1.5, 10.5 Hz, 1H); 4.57 (d, J=5.5 Hz, 2H); 4.52 (dd, J=1.5, 3.5 Hz, 2H); 3.78 (s, 3H). $^{13}$C NMR: δ 194.1, 161.7, 159.1, 158.1, 142.8, 135.3, 133.6, 133.1, 133.0, 131.7, 131.3, 128.2, 127.9, 125.8, 118.3, 117.6, 112.2, 93.0, 92.1, 69.7, 69.3, 56.1. Anal. ($C_{22}H_{21}BrO_4$) C: calcd, 61.55 found, 61.65; H: calcd, 4.93 found, 5.10.

(2E)-3-(2,4-Dimethoxyphenyl)-1-[2-methoxy-4,6-bis(2-propenyloxy)phenyl]-2-propen-1-one (I-17)

Yellow oil; 98.8%; $^1$H NMR: δ 7.63 (d, J=16.5 Hz, 1H); 7.46 (d, J=8 Hz, 1H); 6.98 (d, J=16.5 Hz, 1H); 6.49 (dd, J=2, 8.5 Hz, 1H); 6.42 (d, J=2 Hz, 1H); 6.18 (dd, J=2, 10.5 Hz, 2H); 6.06 (m, 1H); 5.91 (m, 1H); 5.44 (dd, J=1.5, 17.5 Hz, 1H); 5.32 (m, 2H); 5.16 (dd, J=1.5, 10.5 Hz, 1H); 4.55 (d, J=5 Hz, 2H); 4.51 (dd, J=2, 4 Hz, 2H); 3.83 (s, 3H); 3.81 (s, 3H); 3.75 (s, 3H). $^{13}$C NMR: δ 195.1, 163.0, 161.1, 160.2, 158.9, 157.8, 140.3, 140.3, 133.2, 130.6, 127.7, 127.7, 118.2, 117.4, 113.2, 105.5, 98.6, 93.1, 92.2, 69.6, 69.3, 56.1, 55.7, 55.7. Anal. ($C_{24}H_{26}O_6$) C: calcd, 70.23 found, 69.97; H: calcd, 6.38 found, 6.45.

(2E)-1-[2-Methoxy-4,6-bis(2-propenyloxy)phenyl]-3-(3-methoxy-4-hydroxyphenyl)-2-propen-1-one (I-18)

Yellow oil; 49.8%; $^1$H NMR: δ 6.47 (d, J=16 Hz, 1H); 6.22 (s, 2H); 6.08 (d, J=8.5 Hz, 1H); 6.03 (d, J=16.5 Hz, 1H); 5.37 (d, J=9.5 Hz, 2H); 5.27 (m, 1H); 5.24 (s, 1H); 5.08 (m, 1H); 4.63 (d, J=17 Hz, 1H); 4.51 (m, 2H); 4.35 (d, J=11 Hz, 1H); 3.75 (d, J=4 Hz, 2H); 3.69 (d, J=4 Hz, 2H); 3.08 (s, 3H); 2.94 (s, 3H). $^{13}$C NMR: δ 194.5, 161.4, 158.9, 157.9, 148.3, 147.0, 145.1, 133.1, 133.0, 127.7, 127.1, 123.7, 118.3, 117.5, 114.9, 112.7, 109.9, 93.0, 92.1, 69.6, 69.3, 56.2, 56.2. Anal. ($C_{23}H_{24}O_6$) C: calcd, 69.68 found, 67.64; H: calcd, 6.10 found, 6.38.

(2E)-3-(1,3-Benzodioxol-5-yl)-1-[2-methoxy-4,6-bis(2-propenyloxy)phenyl]-2-propen-1-one (I-19)

Yellow oil; 88.1%; $^1$H NMR: δ 7.26 (d, J=16.5 Hz, 1H); 6.99 (d, J=1 Hz, 1H); 6.93 (d, J=8 Hz, 1H); 6.78 (d, J=16 Hz, 1H); 6.72 (d, J=8 Hz, 1H); 6.15 (dd, J=2, 8.5 Hz, 2H); 6.01 (m, 1H); 5.92 (s, 2H), 5.88 (m, 1H); 5.41 (dd, J=1.5, 17.5 Hz, 1H); 5.28 (m, 2H); 5.12 (dd, J=1.5, 10.5 Hz, 1H); 4.52 (d, J=5 Hz, 2H); 4.45 (d, J=4.5 Hz, 2H); 3.71 (s, 3H). $^{13}$C NMR: δ 194.0, 161.4, 159.0, 158.8, 149.8, 148.5, 144.1, 133.1, 132.9, 129.6, 127.5, 124.9, 118.2, 117.5, 112.7, 108.7, 106.9, 101.8, 93.0, 92.1, 69.5, 69.2, 56.1. Anal. ($C_{23}H_{22}O_6$) C: calcd, 70.04 found, 70.28; H: calcd, 5.62 found, 5.75.

(2E)-1-[2-Methoxy-4,6-bis(2-propenyloxy)phenyl]-3-(3,4,5-trimethoxyphenyl)-2-propen-1-one (I-20)

Yellow oil; 97.5%; ¹H NMR: δ 7.27 (d, J=16.5 Hz, 1H); 6.88 (d, J=16 Hz, 1H); 6.75 (s, 2H); 6.19 (dd, J=2, 9.5 Hz, 2H); 6.06 (m, 1H); 5.92 (m, 1H); 5.44 (dd, J=1.5, 17.5 Hz, 1H); 5.32 (m, 2H); 5.18 (dd, J=1.5, 10.5 Hz, 1H); 4.56 (d, J=5.5 Hz, 2H); 4.51 (d, J=5 Hz, 2H); 3.87 (s, 9H); 3.76 (s, 3H). ¹³C NMR: δ 194.2, 161.5, 159.0, 157.9, 153.6, 144.5, 140.3, 133.1, 133.0, 130.7, 128.8, 118.3, 117.5, 112.6, 105.7, 105.7, 93.0, 92.1, 69.6, 69.3, 61.2, 56.4, 56.4, 56.4, 56.2. Anal. ($C_{25}H_{28}O_7$) C: calcd, 68.17 found, 68.05; H: calcd, 6.41 found, 6.48.

(2E,4E)-1-[2-Methoxy-4,6-bis(2-propenyloxy)phenyl]-5-phenyl-2,4-pentadien-1-one (I-21)

Orange oil; 97.2%; ¹H NMR: δ 7.45 (d, J=7 Hz, 2H); 7.35 (m, 3H); 7.16 (dd, J=10.5, 15.5 Hz, 1H); 6.96 (dd, J=10.5, 15 Hz, 1H); 6.85 (d, J=15.5 Hz, 1H); 6.53 (d, J=15 Hz, 1H); 6.18 (m, 2H); 6.07 (m, 1H); 5.94 (m, 1H); 5.40 (dd, J=1.5, 17.5 Hz, 1H); 5.32 (m, 2H); 5.21 (dd, J=1.5, 12 Hz, 1H); 4.57 (dd, J=1.5, 3.5 Hz, 2H); 4.51 (m, 2H); 3.77 (s, 3H). ¹³C NMR: δ 194.4, 161.4, 159.0, 157.9, 144.5, 140.9, 136.5, 133.1, 133.0, 132.8, 129.2, 129.0, 129.0, 128.6, 127.4, 127.4, 118.3, 117.5, 112.7, 93.0, 92.1, 69.6, 69.3, 56.1. Anal. ($C_{24}H_{24}O_4$) C: calcd, 76.57 found, 74.63; H: calcd, 6.43 found, 6.44.

(2E)-3-(1H-pyrrol-2-yl)-1-[2-methoxy-4,6-bis(2-propenyloxy)phenyl]-2-propen-1-one (I-22)

Yellow wax; 10.4%; ¹H NMR: δ 9.15 (s, 1H), 7.25 (d, J=16 Hz, 1H); 6.95 (s, 1H), 6.65 (d, J=15.5 Hz, 1H); 6.52 (s, 1H), 6.26 (d, J=3.5 Hz, 1H); 6.18 (d, J=6.5 Hz, 2H); 6.07 (m, 1H); 5.91 (m, 1H); 5.44 (dd, J=1.5, 17.5 Hz, 1H); 5.33 (m, 2H); 5.17 (dd, J=1.5, 10.5 Hz, 1H); 4.56 (d, J=5 Hz, 2H); 4.49 (d, J=5 Hz, 2H); 3.74 (s, 3H). ¹³C NMR: δ 194.7, 161.2, 158.8, 157.7, 135.3, 133.0, 133.0, 129.1, 123.6, 123.1, 118.3, 117.5, 115.7, 112.5, 111.2, 93.0, 92.0, 69.6, 69.3, 56.1. Anal. ($C_{20}H_{21}NO_4$) C: calcd, 70.78 found, 69.28; H: calcd, 6.24 found, 6.24.

(2E)-3-(4-Fluorophenyl)-1-[2-methoxy-4,6-bis(2-propenyloxy)phenyl]-2-propen-1-one (I-23)

Yellow oil; 79.7%; ¹H NMR: δ 7.49 (m, 2H); 7.35 (d, J=16.5 Hz, 1H); 7.04 (t, J=9 Hz, 2H); 6.89 (d, J=16 Hz, 1H); 6.18 (dd, J=2, 9 Hz, 2H); 6.06 (m, 1H); 5.91 (m, 1H); 5.45 (dd, J=1.5, 17 Hz, 1H); 5.31 (m, 2H); 5.16 (dd, J=1.5, 11 Hz, 1H); 4.55 (d, J=5.5 Hz, 2H); 4.50 (d, J=3.5 Hz, 2H); 3.75 (s, 3H). ¹³C NMR: δ 193.9, 165.0, 163.0, 161.6, 159.1, 158.0, 142.8, 133.1, 132.9, 131.5, 130.4, 129.1, 118.3, 117.5, 116.3, 116.1, 112.5, 93.0, 92.1, 69.6, 69.3, 56.1. Anal. ($C_{22}H_{21}FO_4$) C: calcd, 71.73 found, 71.63; H: calcd, 5.75 found, 5.92.

(2E)-1-[2-Methoxy-4,6-bis(2-propenyloxy)phenyl]-3-(4-methylphenyl)-2-propen-1-one (I-24)

Yellow oil; 93.9%; ¹H NMR: δ 7.41 (d, J=8 Hz, 2H); 7.37 (d, J=16.5 Hz, 1H); 7.17 (d, J=7.5 Hz, 2H); 6.95 (d, J=16 Hz, 1H); 6.20 (dd, J=2, 9.5 Hz, 2H); 6.07 (m, 1H); 5.91 (m, 1H); 5.45 (dd, J=1.5, 17.5 Hz, 1H); 5.32 (m, 2H); 5.16 (dd, J=1.5, 10.5 Hz, 1H); 4.57 (dd, J=1.5, 4.5 Hz, 2H); 4.50 (dd, J=1.5, 4 Hz, 2H); 3.75 (s, 3H); 2.36 (s, 3H). ¹³C NMR: δ 194.4, 161.5, 159.0, 157.9, 144.5, 140.8, 133.1, 132.9, 132.5, 129.8, 129.8, 128.6, 128.6, 128.4, 118.3, 117.5, 112.7, 93.0, 92.1, 69.6, 69.3, 56.1, 21.6. Anal. ($C_{23}H_{24}O_4$) C: calcd, 75.80 found, 75.64; H: calcd, 6.64 found, 6.82.

(2E)-3-(3,5-Bis(2-propenyloxy)-4-bromophenyl)-1-[2-methoxy-4,6-bis(2-propenyloxy)phenyl]-2-propen-1-one (I-25)

Yellow oil; 72.1%; ¹H NMR: δ 7.28 (d, J=16 Hz, 1H); 6.93 (d, J=16.5 Hz, 1H); 6.68 (s, 2H); 6.17 (dd, J=2, 10.5 Hz, 2H); 6.07 (m, 3H); 5.91 (m, 1H); 5.46 (m, 3H); 5.29 (m, 4H); 5.17 (dd, J=1.5, 10.5 Hz, 1H); 4.60 (d, J=5.5 Hz, 4H); 4.57 (d, J=5.5 Hz, 2H); 4.50 (d, J=5.5 Hz, 2H); 3.76 (s, 3H). ¹³C NMR: δ 193.7, 161.7, 159.2, 158.1, 156.6, 156.6, 143.3, 135.4, 133.0, 132.9, 132.6, 132.6, 132.6, 129.8, 118.3, 118.0, 118.0, 117.6, 112.5, 106.2, 106.2, 93.0, 92.2, 70.1, 70.1, 69.6, 69.3, 56.2. Anal. ($C_{28}H_{29}BrO_6$) C: calcd, 62.11 found, 62.62; H: calcd, 5.40 found, 5.39.

(2E)-1-[2-Methoxy-4,6-bis(2-propenyloxy)phenyl]-3-(4-pyridinyl)-2-propen-1-one (I-26)

Yellow oil; 42.2%; ¹H NMR: δ 8.58 (dd, J=1.5, 5 Hz, 2H); 7.28 (d, J=16.5 Hz, 1H); 7.31 (m, 2H); 7.10 (d, J=16 Hz, 1H); 6.15 (dd, J=2, 9.5 Hz, 2H); 6.02 (m, 1H); 5.87 (m, 1H); 5.40 (dd, J=1.5, 17 Hz, 1H); 5.30 (m, 2H); 5.15 (dd, J=1.5, 10.5 Hz, 1H); 4.53 (ddd, J=1.5, 5, 1.5 Hz, 2H); 4.48 (ddd, J=1.5, 5, 1.5 Hz, 2H); 3.74 (s, 3H). ¹³C NMR: δ 192.8, 162.0, 159.4, 158.4, 150.7, 150.7, 142.7, 139.9, 132.9, 132.9, 132.8, 122.2, 122.2, 118.3, 117.7, 112.1, 93.0, 92.1, 69.6, 69.3, 56.2. Anal. ($C_{21}H_{21}NO_4$) C: calcd, 71.78 found, 70.49; H: calcd, 6.02 found, 6.04.

(2E)-1-[2-Methoxy-4,6-bis(2-propenyloxy)phenyl]-3-(2-pyridinyl)-2-propen-1-one (I-27)

Yellow oil; 84.3%; ¹H NMR: δ 8.52 (d, J=5 Hz, 1H); 7.59 (td, J=2, 7.5 Hz, 1H); 7.38 (d, J=8 Hz, 1H); 7.33 (d, J=16 Hz, 1H); 7.27 (d, J=16.5 Hz, 1H); 7.13 (m, 1H); 6.09 (d, J=7 Hz, 2H); 5.95 (m, 1H); 5.81 (m, 1H); 5.35 (dd, J=1.5, 17.5 Hz, 1H); 5.23 (m, 2H); 5.06 (dd, J=1.5, 10.5 Hz, 1H); 4.47 (d, J=5 Hz, 2H); 4.41 (dd, J=1.5, 3.5 Hz, 2H); 3.65 (s, 3H). ¹³C NMR: δ 194.2, 161.6, 159.1, 158.0, 153.9, 150.2, 142.7, 136.9, 133.1, 132.9, 132.5, 124.2, 124.1, 118.1, 117.5, 112.3, 93.0, 92.1, 69.5, 69.2, 56.0. Anal. ($C_{21}H_{21}NO_4$) C: calcd, 71.78 found, 71.52; H: calcd, 6.02 found, 5.96.

(2E)-3-(2-furanyl)-1-[2-methoxy-4,6-bis(2-propenyloxy)phenyl]-2-propen-1-one (1-28)

Orange wax; 87.2%; ¹H NMR: δ 7.42 (s, 1H), 7.11 (d, J=16 Hz, 1H); 6.81 (d, J=15.5 Hz, 1H); 6.54 (d, J=3 Hz, 1H); 6.39 (dd, J=1.5, 3 Hz, 1H); 6.13 (dd, J=2, 7.5 Hz, 2H); 5.99 (m, 1H); 5.86 (m, 1H); 5.37 (dd, J=1.5, 18 Hz, 1H); 5.26 (m, 2H); 5.11 (dd, J=1.5, 11 Hz, 1H); 4.51 (d, J=5 Hz, 2H); 4.45 (dd, J=1, 3 Hz, 2H); 3.67 (s, 3H). ¹³C NMR: δ 193.6, 161.5, 159.0, 157.9, 151.6, 145.1, 133.1, 132.9, 130.4, 126.9, 118.1, 117.4, 115.4, 112.7, 112.4, 93.0, 92.1, 69.5, 69.2, 56.1. Anal. ($C_{20}H_{20}O_5$) C: calcd, 70.57 found, 68.72; H: calcd, 5.92 found, 5.82.

(2E)-1-(2,4-Dihydroxy-6-methoxyphenyl)-3-(phenyl)-2-propen-1-one (I-29)

Yellow solid (186-188° C.); 10.2%; ¹H NMR: δ 7.82 (d, J=15.5 Hz, 1H); 7.65 (d, J=15.5 Hz, 1H); 7.53 (d, J=8 Hz, 2H); 7.33 (m, 3H); 5.93 (d, J=2.5 Hz, 1H); 5.89 (s, 1H); 3.85 (s, 3H); 3.57 (s, 2H). ¹³C NMR: δ 192.8, 167.4, 165.2, 163.5, 142.2, 135.7, 130.2, 129.0, 129.0, 128.4, 128.4, 127.9, 105.8, 96.4, 91.8, 55.9 Anal. ($C_{16}H_{14}O_4$) C: calcd, 71.10 found, 71.55; H: calcd, 5.22 found, 6.16.

(2E)-1-(2,4-Dihydroxy-6-methoxyphenyl)-3-(4-hydroxyphenyl)-2-propen-1-one (I-30)

Yellow solid (decomposes: 220° C.); 52.6%; $^1$H NMR: δ 7.67 (d, J=16 Hz, 1H); 7.60 (d, J=15.5 Hz, 1H); 7.38 (d, J=8.5 Hz, 2H); 6.74 (d, J=8.5 Hz, 2H); 5.89 (d, J=2.5 Hz, 1H); 5.86 (d, J=2 Hz, 1H); 3.86 (s, 3H); 3.81 (s, 3H). $^{13}$C NMR: δ 191.9, 166.2, 163.8, 162.3, 158.4, 141.9, 129.4, 129.4, 126.3, 123.6, 114.9, 114.9, 104.7, 95.3, 90.7, 54.8 Anal. ($C_{16}H_{14}O_5$) C: calcd, 67.13 found, 66.55; H: calcd, 4.93 found, 5.03.

(2E)-1-(2,4-Dihydroxy-6-methoxyphenyl)-3-(3-methoxyphenyl)-2-propen-1-one (I-31)

Yellow solid (159-162° C.); 5.9%; $^1$H NMR: δ 7.79 (d, J=15.5 Hz, 1H); 7.63 (d, J=16 Hz, 1H); 7.25 (t, J=8 Hz, 1H); 7.14 (d, J=7.5 Hz, 1H); 7.05 (s, 1H); 6.87 (dd, J=2.5, 8.5 Hz, 1H); 5.93 (d, J=2.5 Hz, 1H); 5.89 (d, J=2.5 Hz, 1H); 3.84 (s, 3H); 3.78 (s, 3H); 3.20 (s, 2H). $^{13}$C NMR: δ 192.8, 167.4, 165.2, 163.5, 159.9, 142.0, 137.2, 130.0, 128.3, 121.1, 115.7, 113.7, 105.8, 96.4, 91.9, 55.9, 55.5 Anal. ($C_{17}H_{16}O_5$) C: calcd, 67.99 found, 68.73; H: calcd, 5.37 found, 6.34.

(2E)-1-(2,4-Dihydroxy-6-methoxyphenyl)-3-[4-(trifluoromethyl)phenyl]-2-propen-1-one (I-32)

Yellow solid (231-233° C.); 7.3%; $^1$H NMR: δ 7.85 (d, J=16 Hz, 1H); 7.61 (m, 4H); 7.56 (d, J=8.5 Hz, 1H); 5.94 (d, J=2.5 Hz, 1H); 5.89 (d, J=2 Hz, 1H); 3.84 (s, 3H); 3.58 (s, 2H). $^{13}$C NMR: δ 192.3, 167.5, 165.6, 163.5, 139.8. 139.8, 139.2, 130.4, 130.4, 128.5.2, 128.5, 125.9, 125.9, 105.7, 96.4, 91.9, 56.0 Anal. ($C_{17}H_{13}F_3O_4$) C: calcd, 60.36 found, 62.82; H: calcd, 3.87 found, 4.86.

(2E)-3-(4-Chlorophenyl)-1-(2,4-dihydroxy-6-methoxyphenyl)-2-propen-1-one (I-33)

Yellow solid (171-174° C.); 11.5%; $^1$H NMR: δ 7.83 (d, J=16 Hz, 1H); 7.65 (d, J=15.5 Hz, 1H); 7.50 (d, J=8.5 Hz, 2H); 7.34 (d, J=8.5 Hz, 2H); 5.99 (d, J=2.5 Hz, 1H); 5.93 (d, J=2 Hz, 1H); 3.89 (s, 3H); 2.62 (bs, 2H). $^{13}$C NMR: δ 192.5, 167.5, 165.2, 163.5, 140.7, 135.9, 134.3, 129.6, 129.6, 129.3, 129.3, 128.4, 105.9, 96.5, 91.9, 56.1 Anal. ($C_{16}H_{13}ClO_4$) C: calcd, 63.06 found, 63.89; H: calcd, 4.30 found, 4.69.

(2E)-1-(2,4-Dihydroxy-6-methoxyphenyl)-3-(2-fluorophenyl)-2-propen-1-one (I-34)

Yellow solid (184-186° C.); 25.7%; $^1$H NMR: δ 7.94 (d, J=15.5 Hz, 1H); 7.75 (d, J=16 Hz, 1H); 7.54 (t, J=7.5, 15 Hz, 1H); 7.28 (m, 1H); 7.13 (t, J=7.5, 15 Hz, 1H); 7.05 (t, J=9.5, 19 Hz, 1H); 5.95 (d, J=2.5 Hz, 1H); 5.90 (d, J=1.5 Hz, 1H); 3.85 (s, 3H). $^{13}$C NMR: δ 192.8, 167.4, 165.3, 163.5, 162.8, 160.8, 134.8, 131.5, 130.4, 129.7, 124.6, 116.4, 105.8, 96.4, 91.9, 55.9 Anal. ($C_{16}H_{13}FO_4$) C: calcd, 66.66 found, 66.96; H: calcd, 4.55 found, 4.71.

(2E)-3-(2-Bromophenyl)-1-(2,4-dihydroxy-6-methoxyphenyl)-2-propen-1-one (I-35)

Yellow solid (181-183° C.); 7.8%; $^1$H NMR: δ 7.98 (d, J=15.5 Hz, 1H); 7.74 (d, J=16 Hz, 1H); 7.61 (d, J=7.5 Hz, 1H); 7.55 (d, J=8.5 Hz, 1H); 7.28 (m, 1H); 7.15 (m, 1H); 5.93 (s, 1H); 5.89 (s, 1H); 3.83 (s, 3H); 3.59 (s, 2H). $^{13}$C NMR: δ 192.4, 167.5, 165.4, 163.5, 140.2, 135.7, 133.6, 131.0, 130.6, 127.9, 127.8, 125.9, 105.8, 96.4, 91.8, 55.9 Anal. ($C_{16}H_{13}BrO_4$) C: calcd, 55.04 found, 61.11; H: calcd, 3.75 found, 5.49.

(2E)-1-(2,4-Dihydroxy-6-methoxyphenyl)-3-(2,4-dimethoxyphenyl)-2-propen-1-one (I-36)

Yellow solid (166-168° C.); 32.8%; $^1$H NMR: δ 8.02 (d, J=15.5 Hz, 1H); 7.86 (d, J=15.5 Hz, 1H); 7.50 (d, J=8.5 Hz, 1H); 6.50 (dd, J=2.5, 8.5 Hz, 1H); 6.43 (d, J=2.5 Hz, 1H); 5.95 (d, J=2.5 Hz, 1H); 5.91 (d, J=2 Hz, 1H); 3.86 (s, 3H); 3.86 (s, 3H); 3.81 (s, 3H); 3.08 (s, 2H). $^{13}$C NMR: δ 193.3, 167.3, 164.6, 163.4, 162.9, 160.4, 138.2, 130.6, 125.7, 117.9, 106.0, 105.7, 98.5, 96.3, 91.8, 55.9, 55.8, 55.6 Anal. ($C_{18}H_{18}O_6$) C: calcd, 65.45 found, 65.16; H: calcd, 5.49 found, 5.46.

(2E)-1-(2,4-Dihydroxy-6-methoxyphenyl)-3-(3-methoxy-4-hydroxyphenyl)-2-propen-1-one (I-37)

Yellow solid (205-207° C.); 44.6%; $^1$H NMR: δ 7.57 (d, J=16 Hz, 1H); 7.48 (d, J=15.5 Hz, 1H); 6.93 (m, 2H); 6.67 (d, J=8 Hz, 1H); 5.79 (s, 1H); 5.78 (s, 1H); 4.22 (s, 3H); 3.72 (s, 3H); 3.71 (s, 3H). $^{13}$C NMR: δ 192.7, 167.2, 164.9, 163.3, 148.8, 147.7, 142.9, 127.7, 124.8, 122.8, 122.8, 115.4, 110.9, 105.6, 96.2, 91.6, 55.6 Anal. ($C_{17}H_{16}O_6$) C: calcd, 64.55 found, 64.31; H: calcd, 5.10 found, 5.14.

(2E)-1-(2,4-Dihydroxy-6-methoxyphenyl)-3-(3,4,5-trimethoxydroxyphenyl)-2-propen-1-one (I-38)

Orange solid (181-183° C.); 32.6%; $^1$H NMR: δ 7.63 (d, J=15.5 Hz, 1H); 7.45 (d, J=15.5 Hz, 1H); 6.67 (s, 2H); 5.84 (s, 1H); 5.80 (s, 1H); 4.22 (s, 2H); 3.74 (s, 6H); 3.73 (s, 3H); 3.71 (s, 3H). $^{13}$C NMR: δ 192.5, 167.4, 165.1, 163.3, 153.4, 153.4, 141.9, 139.8, 131.4, 127.4, 105.7, 105.6, 105.6, 96.4, 91.7, 60.9, 56.0, 55.7, 55.7 Anal. ($C_{19}H_{20}O_7$) C: calcd, 63.33 found, 62.55; H: calcd, 5.59 found, 5.59.

(2E,4E)-1-(2,4-Dihydroxy-6-methoxyphenyl)-5-phenyl-2,4-pentadien-1-one (I-39)

Orange solid (199-201° C.); 44.3%; $^1$H NMR: δ 7.57 (m, 1H); 7.48 (m, 2H); 7.42 (m, 1H); 7.35 (m, 2H); 7.29 (m, 1H); 6.99 (m, 2H); 5.98 (d, J=2 Hz, 1H); 5.92 (d, J=2 Hz, 1H); 3.88 (s, 3H), 2.32 (s, 2H). $^{13}$C NMR: δ 192.6, 167.5, 164.8, 163.4, 143.0, 141.0, 136.6, 131.3, 129.2, 129.0, 129.0, 128.5, 127.9, 127.4, 105.9, 96.5, 91.8, 55.9. Anal. ($C_{18}H_{16}O_4$) C: calcd, 72.96 found, 72.69; H: calcd, 5.44 found, 5.41.

(2E)-1-(2,4-Dihydroxy-6-methoxyphenyl)-3-(4-fluorophenyl)-2-propen-1-one (I-40)

Yellow solid (216-219° C.); 79.9%; $^1$H NMR: δ 7.77 (d, J=15.5 Hz, 1H); 7.64 (d, J=15.5 Hz, 1H); 7.53 (m, 2H); 7.05 (m, 2H); 5.96 (d, J=2.5 Hz, 1H); 5.91 (d, J=2 Hz, 1H); 3.87 (s, 3H); 3.17 (bs, 2H). $^{13}$C NMR: δ 192.6, 167.4, 165.2, 164.9, 163.5, 162.9, 140.9, 132.0, 130.3, 127.7, 116.2, 116.1, 105.8, 96.4, 91.9, 56.0 Anal. ($C_{16}H_{13}FO_4$) C: calcd, 66.66 found, 67.56; H: calcd, 4.55 found, 4.92.

(2E)-1-(2,4-Dihydroxy-6-methoxyphenyl)-3-(4-methylphenyl)-2-propen-1-one (I-41)

Orange solid (165-167° C.); 20.2%; $^1$H NMR: δ 7.84 (d, J=15 Hz, 1H); 7.73 (d, J=15.5 Hz, 1H); 7.48 (d, J=8 Hz, 2H);

7.19 (d, J=8 Hz, 2H); 5.99 (d, J=2.5 Hz, 1H); 5.94 (d, J=2 Hz, 1H); 3.89 (s, 3H); 2.37 (s, 3H). $^{13}$C NMR: δ 192.9, 167.4, 164.8, 163.5, 142.5, 140.7, 133.0, 129.8, 129.8, 128.6, 128.6, 126.9, 105.9, 96.5, 91.9, 56.1, 21.7 Anal. ($C_{17}H_{16}O_4$) C: calcd, 71.82 found, 71.82; H: calcd, 5.67 found, 5.67.

(2E)-3-(3,5-Bis(2-propenyloxy)-4-bromophenyl)-1-(2,4-dihydroxy-6-methoxyphenyl)-2-propen-1-one (I-42)

Yellow solid (168-170° C.); 22.4%; $^1$H NMR: δ 7.68 (d, J=15.5 Hz, 1H); 7.44 (d, J=16 Hz, 1H); 6.64 (s, 2H); 5.96 (m, 2H); 5.89 (s, 1H); 5.83 (s, 1H); 5.38 (d, J=17.5 Hz, 2H); 5.20 (d, J=10.5 Hz, 2H); 5.54 (s, 4H); 3.95 (s, 2H); 3.77 (s, 3H). $^{13}$C NMR: δ 192.4, 167.4, 165.4, 163.4, 156.4, 156.4, 141.2, 135.9, 132.6, 132.6, 128.6, 117.8, 117.7, 106.1, 106.1, 105.7, 104.4, 96.4, 91.8, 70.0, 70.0, 55.8 Anal. ($C_{22}H_{21}BrO_6$) C: calcd, 57.28 found, 57.26; H: calcd, 4.59 found, 4.57.

(2E)-1-(2,4-Dihydroxy-6-methoxyphenyl)-3-(2-furanyl)-2-propen-1-one (I-43)

Yellow solid (174-175° C.); 65.1%; $^1$H NMR: δ 7.70 (d, J=15.5 Hz, 1H); 7.44 (d, J=15 Hz, 1H); 7.43 (s, 1H); 6.58 (d, J=3.5 Hz, 1H); 6.41 (dd, J=2, 3 Hz, 1H); 5.91 (d, J=2 Hz, 1H); 5.87 (d, J=2 Hz, 1H); 3.82 (s, 3H). $^{13}$C NMR: δ 192.3, 167.4, 165.1, 163.5, 152.3, 144.9, 128.9, 125.2, 115.6, 112.7, 105.8, 96.3, 91.7, 55.8. Anal. ($C_{14}H_{12}O_5$) C: calcd, 64.61 found, 64.79; H: calcd, 4.65 found, 4.60.

(2E)-1-(2,4-Dimethoxymethyl-6-methoxyphenyl)-3-(4-methoxyphenyl)-2-propen-1-one (I-44)

Yellow wax; 100.0%; $^1$H NMR: δ 7.40 (d, J=8.5 Hz, 2H); 7.27 (d, J=16 Hz, 1H); 6.82 (m, 3H); 6.47 (s, 1H); 6.33 (s, 1H); 5.13 (s, 2H); 5.04 (s, 2H); 3.73 (s, 3H); 3.68 (s, 3H); 3.43 (s, 3H); 3.31 (s, 3H). $^{13}$C NMR: δ 194.3, 161.8, 159.9, 158.6, 156.0, 144.9, 130.2, 127.7, 127.1, 114.6, 114.6, 114.2, 96.2, 94.8, 74.7, 94.3, 94.2, 56.4, 56.1, 55.5, 55.4 Anal. ($C_{21}H_{24}O_7$) C: calcd, 64.94 found, 61.86; H: calcd, 6.23 found, 5.95.

(2E)-3-(1,3-Benzodioxol-5-yl)-1-(2,4-dimethoxymethyl-6-methoxyphenyl)-2-propen-1-one (I-45)

Yellow wax; 60.9%; $^1$H NMR: δ 7.21 (d, J=16.5 Hz, 1H); 6.98 (s, 1H); 6.90 (d, J=8 Hz, 1H); 6.71 (m, 2H); 6.44 (s, 1H); 6.31 (s, 1H); 5.89 (s, 2H); 5.12 (s, 2H); 5.04 (s, 2H); 3.68 (s, 3H); 3.42 (s, 3H); 3.01 (s, 3H). $^{13}$C NMR: δ 194.1, 160.0, 158.6, 156.0, 149.9, 148.6, 144.7, 129.4, 127.4, 125.0, 114.1, 108.7, 106.8, 101.8, 96.2, 94.6, 94.2, 56.4, 56.1, 56.1, 56.0 Anal. ($C_{21}H_{22}O_8$) C: calcd, 62.68 found, 58.64; H: calcd, 5.51 found, 5.13.

(2E)-1-(2-Hydroxy-4-methoxymethyl-6-methoxyphenyl)-3-(3,4,5-trimethoxyphenyl)-2-propen-1-one (I-46)

Yellow solid (136-138° C.); 25.5%; $^1$H NMR: δ 7.75 (d, J=15.5 Hz, 1H); 7.66 (d, J=15.5 Hz, 1H); 6.81 (s, 2H); 6.23 (s, 1H); 6.05 (s, 1H); 5.17 (s, 2H); 3.88 (s, 12H); 3.47 (s, 3H). $^{13}$C NMR: δ 192.7, 168.0, 163.9, 162.8, 153.6, 142.7, 140.4, 131.3, 127.1, 107.2, 105.9, 105.9, 96.9, 94.3, 94.2, 92.0, 61.2, 56.7, 56.4, 56.1, 56.0 Anal. ($C_{21}H_{24}O_8$) C: calcd, 62.37 found, 62.65; H: calcd, 5.98 found, 6.17.

1-(2-Hydroxy-4,6-dimethoxyphenyl)-ethanone

Yellow solid; quantitative; $^1$H NMR: δ 5.98 (d, J=2 Hz, 1H); 5.87 (d, J=2 Hz, 1H); 3.79 (s, 3H); 3.76 (s, 3H); 3.07 (s, 1H); 2.54 (s, 3H). $^{13}$C NMR: δ 203.5, 167.2, 166.3, 163.2, 106.1, 93.6, 90.9, 55.7, 55.6, 33.1.

1-(2,4-Dihydroxy-6-methoxyphenyl)-ethanone

Yellow solid; 44.1%; $^1$H NMR: δ 5.95 (d, J=2 Hz, 1H); 5.88 (d, J=2 Hz, 1H); 4.87 (s, 2H); 3.86 (s, 3H); 2.55 (s, 3H). $^{13}$C NMR: δ 203.0, 167.1, 165.5, 164.0, 105.0, 95.6, 90.8, 54.9, 31.8.

1-[2-Methoxy-4,6-bis(2-propenyloxy)phenyl]-ethanone

Colorless oil; 85.0%; $^1$H NMR: δ 6.06 (dd, J=1.5, 8 Hz, 2H); 5.93 (m, 2H); 5.32 (m, 2H); 5.18 (ddd, J=1, 10.5, 24 Hz, 2H); 4.45 (d, J=5 Hz, 2H); 4.43 (d, J=5 Hz, 2H); 3.69 (s, 3H); 2.39 (s, 3H). $^{13}$C NMR: δ 201.6, 161.3, 158.3, 157.3, 133.1, 132.9, 118.0, 117.6, 114.4, 92.7, 91.9, 69.5, 69.1, 55.9, 32.7.

Example Syntheses of Some Formula (II) Compounds when $R^5$ is H

Some Formula (II) compounds can be synthesized, in some embodiments, as summarized in Scheme 2. This Scheme begins with the preparation of the 2-amino-4,5,6,7-tetrahydrobenzo[b]thienophene-3-carboxylic acid ethyl ester by using the Gewald reaction and then preparing the cyclic pyrimidinone compound F, by reacting the 2-aminothiophene carboxylic ester with excess of formamide. Compound F undergoes chlorination using phosphorus oxychloride ($POCl_3$) yielding the suitable electrophile for the nucleophilic displacement using aqueous hydrazine generating the corresponding aromatic hydrazine derivative compound G (which is also referred to as PC for precursor). The Scheme concludes with the synthesis of the Formula (II) compounds by forming the Schiff base upon reaction of compound G with the corresponding aromatic aldehyde.

Scheme 2. Synthesis of Some Formula (II) Compounds when $R^5$ is H.

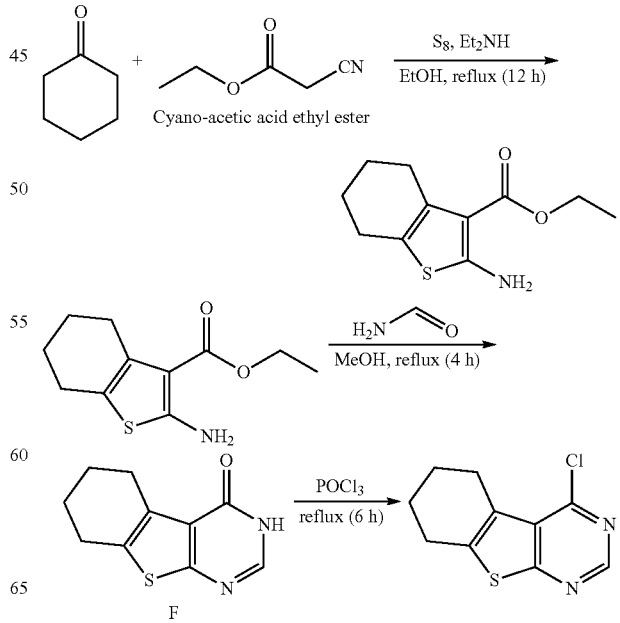

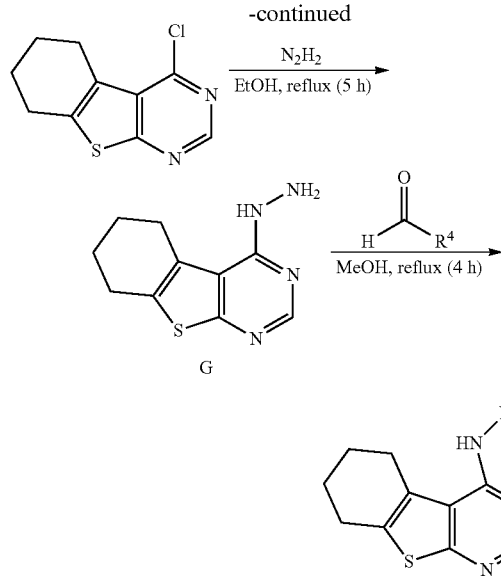

Examples Syntheses of Formula (II) Including Yields of Some Intermediates

| Compound | Aldehyde/Ketone | Yield (%) |
|---|---|---|
| II-16 | $R^5$ = H, $R^4$ = $C_6H_2$-3,5-$OCH_3$, 4-OH | 59.6 |
| II-17 | $R^5$ = H, $R^4$ = $C_6H_2$-3,5-Allyloxy, 4-Br | 95.2 |
| II-18 | $R^5$ = H, $R^4$ = 2-Furyl | 67.5 |
| II-19 | $R^5$ = H, $R^4$ = 2-Pyrrolyl | 61.9 |
| II-20 | $R^5$ = H, $R^4$ = 4-Pyridinyl | 76.3 |
| II-21 | $R^5$ = H, $R^4$ = 2-Pyridinyl | 82.8 |
| II-22 | $R^5$ = H, $R^4$ = $C_6H_4$-4-$NO_2$ | 85.6 |
| II-23 | $R^5$ = H, $R^4$ = $C_6H_4$-2-$NO_2$ | 91.7 |
| II-24 | $R^5$ = H, $R^4$ = $C_6H_4$-4-$CF_3$ | 94.4 |
| II-25 | $R^5$ = H, $R^4$ = $C_6H_4$-2-$CF_3$ | 40.8 |
| II-26 | $R^5$ = H, $R^4$ = $C_6H_4$-4-F | 99.4 |
| II-27 | $R^5$ = H, $R^4$ = $C_6H_4$-2-F | 86.6 |
| II-28 | $R^5$ = H, $R^4$ = $C_6H_4$-4-Cl | 97.7 |
| II-29 | $R^5$ = H, $R^4$ = $C_6H_4$-2-Cl | 88.3 |
| II-30 | $R^5$ = H, $R^4$ = $C_6H_4$-4-Br | 95.4 |
| II-31 | $R^5$ = H, $R^4$ = $C_6H_4$-2-Br | 90.7 |
| II-32 | $R^5$ = H, $R^4$ = $C_6H_4$-4-CN | 95.8 |
| II-33 | $R^5$ = H, $R^4$ = $C_6H_4$-2-CN | — |
| II-34 | $R^5$, $R^4$ = H | — |
| II-35 | $R^5$ = H, $R^4$ = $CH_3$ | — |
| II-36 | $R^5$ = H, $R^4$ = $C(CH_3)_3$ | 97.9 |
| II-37 | $R^5$ = H, $R^4$ = CH=$CH_2$ | — |
| II-38 | $R^5$ = H, $R^4$ = $C_5H_{11}$ | — |
| II-39 | $R^5$ = H, $R^4$ = $C_6H_{11}$ | — |
| II-40 | $R^5$ = H, $R^4$ = $CH_2CH_2$—($C_6H_5$) | — |
| II-41 | $R^5$ = H, $R^4$ = $CH_2$—O—$CH_2$—($C_6H_5$) | — |
| II-42 | $R^5$ = H, $R^4$ = $CH_2CH_2$—S—$CH_3$ | — |
| II-43 | $R^5$ = H, $R^4$ = $CH_2CH$-3-(methyl-2-furyl)-$CH_3$ | — |

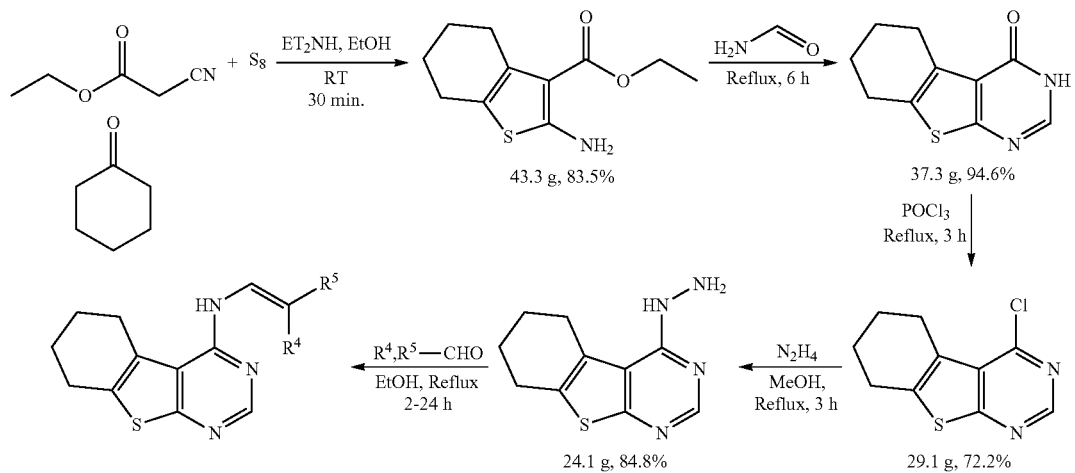

Yields of Some Compound (II) Syntheses

| Compound | Aldehyde/Ketone | Yield (%) |
|---|---|---|
| II-1 | $R^5$ = H, $R^4$ = $C_6H_5$ | 99.2 |
| II-2 | $R^5$ = H, $R^4$ = 1-Naphthalenyl | 47.6 |
| II-3 | $R^5$ = H, $R^4$ = 2-Naphthalenyl | 70.1 |
| II-4 | $R^5$ = H, $R^4$ = Cinnamyl | 66.6 |
| II-5 | $R^5$ = H, $R^4$ = $C_6H_4$-4-$CH_3$ | 92.1 |
| II-6 | $R^5$ = H, $R^4$ = $C_6H_4$-4-$CH_2CH_3$ | 85.4 |
| II-7 | $R^5$ = H, $R^4$ = $C_6H_4$-4-$CH(C_2H_6)$ | 65.9 |
| II-8 | $R^5$ = H, $R^4$ = $C_6H_4$-4-$C(C_3H_9)$ | 60.2 |
| II-9 | $R^5$ = H, $R^4$ = $C_6H_4$-4-OH | 77.1 |
| II-10 | $R^5$ = H, $R^4$ = $C_6H_4$-4-$OCH_3$ | 93.9 |
| II-11 | $R^5$ = H, $R^4$ = $C_6H_4$-3-$OCH_3$ | 81.8 |
| II-12 | $R^5$ = H, $R^4$ = $C_6H_3$-3,4-O—$CH_2$—O | 89.6 |
| II-13 | $R^5$ = H, $R^4$ = $C_6H_3$-2,4-$OCH_3$ | 76.0 |
| II-14 | $R^5$ = H, $R^4$ = $C_6H_2$-3,4,5-$OCH_3$ | 62.4 |
| II-15 | $R^5$ = H, $R^4$ = $C_6H_3$-3-$OCH_3$, 4-OH | 80.0 |
| II-44 | $R^5$ = $CH_3$, $R^4$ = $CH_3$ | 43.9 |
| II-45 | $R^5$ = $CH_3$, $R^4$ = $CH_2CH_3$ | — |
| II-46 | $R^5$ = $CH_3$, $R^4$ = $CHCH_2$ | — |
| II-47 | $R^5$ = $CH_3$, $R^4$ = $C_6H_5$ | 18.9 |
| II-48 | $R^5$, $R^4$ = $CH_2CH_3$ | 56.3 |
| II-49 | $R^5$, $R^4$ = $C_6H_5$ | 69.9 |
| II-50 | $R^5$, $R^4$ = $CH_2$—$(CH_2)_3$—$CH_2$ | — |
| II-51 | $R^5$ = H, $R^4$ = O—$CH_2$—O—$CH_3$ | — |

Cell Growth Inhibition Bioassay—Tables 1A and 1B.

The cytotoxicity of compounds was assayed as follows. Growth inhibition was evaluated by preparing serial dilutions of each fraction or compound (up to a maximum concentration of 62.5 µg/mL) and incubating the cells in 96-well plates in the presence or absence of these fractions for 48 h at 37° C.

Appropriate solvent controls were tested for comparison. The percent inhibition of cell growth relative to the control was evaluated colorimetrically using a sulforhodamine B dye by comparison to the control. The calorimetric procedure followed that published in Skehan et al., *J. Nat. Cancer Inst.*, Vol. 4, pp. 1107-1112 (1990) and Boyd & Paull, *Drug Dev. Res.*, Vol. 34, pp. 91-109 (1995). The $GI_{50}$ value is defined as the concentration of test sample resulting in a 50% reduction of absorbance as compared with untreated controls that received a serial dilution of the solvent in which the test samples were dissolved, and was determined by linear regression analysis. The cell lines are: 3T3 cells are BALB/3T3 clone A31 embryonic mouse fibroblast cells; H460 cells are human large cell lung cancer cells; DU145 cells are human prostate carcinoma cells; MCF-7 cells are human breast adenocarcinoma cells; M-14 cells are human melanoma cells; HT-29 cells are human colon adenocarcinoma cells; PC3 cells are human prostate adenocarcinoma cells; K562 cells are human chronic myelogenous leukemia cells; and VERO cells are African Green Monkey kidney epithelial cells.

TABLE 1a

Cytotoxicity of Some Formula (I) Compounds

| Compound | $GI_{50}$ (μM) in indicated cell line | | | | | | | |
|---|---|---|---|---|---|---|---|---|
| | 3T3 | H460 | DU145 | MCF-7 | M-14 | HT-29 | PC3 | K562 |
| I-07 | >206 | 128.0 | >206 | 65.5 | 109.2 | >206 | 59.9 | 22.8 |
| I-03 | >197 | >197 | >197 | >197 | >197 | >197 | >197 | >197 |
| I-04 | 21.5 | 105.3 | 60.2 | 42.4 | 82.0 | 144.7 | 39.1 | 28.2 |
| I-01 | 17.2 | 24.1 | 30.8 | 17.5 | 22.5 | 45.3 | 15.2 | 20.5 |
| I-02 | 39.0 | >190 | >190 | 140.1 | >190 | >190 | 118.5 | 18.9 |
| I-05 | 6.7 | 14.0 | 9.0 | 17.3 | 19.6 | 21.6 | 19.3 | 17.0 |
| I-06 | 5.1 | 15.6 | 12.4 | 20.4 | 22.6 | 20.7 | 18.5 | 16.2 |
| I-10 | 41.0 | 20.0 | 21.0 | 19.5 | 27.6 | 28.4 | 18.1 | 16.6 |
| I-19 | 31.7 | 14.5 | 17.5 | 10.9 | 17.2 | 24.1 | 9.6 | 12.2 |
| 5FU[a] | <1.54 | 4.1 | 15.4 | 6.5 | 22.4 | 8.9 | 14.6 | 16.7 |

[a]5FU, 5-Fluorouracil

TABLE 1b

Cytotoxicity of Some Formula (II) Compounds

| Compound | $GI_{50}$ (μg/mL) in indicated cell line | | | | | | | |
|---|---|---|---|---|---|---|---|---|
| | 3T3 | H460 | VERO | DU145 | MCF-7 | M-14 | HT-29 | K562 |
| PC | <0.98 | 2.1 | 2.5 | 3.1 | 2.0 | 5.4 | 4.6 | 2.4 |
| II-01 | 6.7 | 5.6 | 5.3 | 6.2 | 3.5 | 5.6 | 3.8 | 4.1 |
| II-02 | 6.0 | 7.1 | 4.3 | 8.6 | 2.3 | 6.6 | 2.2 | 1.7 |
| II-03 | 10.0 | 7.4 | 2.9 | 8.7 | 3.3 | 12.6 | 6.9 | 2.2 |
| II-04 | 1.5 | 0.7 | 0.6 | 1.8 | 0.7 | 1.6 | 2.7 | 0.5 |
| II-05 | 12.1 | 42.9 | 10.0 | >62.5 | 4.2 | >62.5 | >62.5 | 2.3 |
| II-06 | 12.1 | 9.5 | 6.6 | 19.8 | 6.2 | 64.0 | 10.8 | 3.7 |
| II-07 | 3.3 | 2.1 | 2.1 | 3.8 | 1.8 | 6.2 | 2.1 | 1.4 |
| II-08 | 8.4 | 2.3 | 2.5 | 8.0 | 2.3 | 11.0 | 5.7 | 2.3 |
| II-09 | 2.1 | 4.8 | 6.8 | 6.8 | 5.5 | 5.6 | 6.3 | 5.1 |
| II-10 | 5.0 | 5.8 | 6.4 | 7.8 | 4.2 | 5.5 | 5.9 | 4.7 |
| II-11 | 6.0 | 5.5 | 6.2 | 6.0 | 5.0 | 48.4 | 2.5 | 5.3 |
| II-12 | >93.75 | >93.75 | >93.75 | >93.75 | 41.36 | >93.75 | >93.75 | >93.75 |
| II-13 | 7.3 | 10.9 | 17.7 | 7.4 | 7.8 | 34.8 | 7.4 | 2.9 |
| II-14 | 9.0 | 11.3 | 9.7 | 9.0 | 4.2 | 6.2 | 4.6 | 1.9 |
| II-15 | 3.6 | 7.2 | 7.0 | 3.5 | 4.8 | 6.7 | 6.6 | 3.2 |
| II-16 | 10.5 | >62.5 | >62.5 | 10.5 | >62.5 | >62.5 | >62.5 | >62.5 |
| II-17 | <0.98 | 1.6 | 2.2 | <0.98 | 1.9 | 6.4 | 1.9 | 2.0 |
| II-18 | 2.3 | 2.1 | 2.6 | 4.7 | 0.3 | 3.3 | 2.5 | 1.2 |
| II-19 | 0.7 | 0.5 | 0.6 | 1.4 | 0.1 | 0.7 | 1.1 | 0.6 |
| II-20 | 25.7 | 52.4 | 38.3 | 26.0 | 26.0 | >62.5 | 47.3 | 33.8 |
| II-21 | 0.013 | 0.123 | 0.156 | 0.115 | 0.026 | 0.078 | 0.030 | 0.051 |
| II-22 | >62.5 | >62.5 | >62.5 | >62.5 | >62.5 | >62.5 | >62.5 | >62.5 |
| II-23 | >62.5 | 18.7 | >62.5 | 36.4 | 18.4 | 58.9 | 70.5 | 61.6 |
| II-24 | 4.0 | 5.8 | 5.4 | 5.6 | 2.0 | 6.4 | 2.6 | 2.5 |
| II-25 | 6.0 | 2.0 | 1.7 | 1.3 | 1.8 | 2.5 | 1.7 | 0.6 |
| II-26 | 6.7 | 3.1 | 4.2 | 4.5 | 2.4 | 5.7 | 3.4 | 2.9 |
| II-27 | >93.75 | >93.75 | >93.75 | >93.75 | 24.47 | >93.75 | >93.75 | 26.49 |
| II-28 | 6.4 | 4.4 | 3.0 | 5.0 | 2.9 | >62.5 | 5.2 | 2.3 |
| II-29 | 30.2 | 21.6 | 9.9 | 26.7 | 7.5 | >62.5 | 19.4 | 6.8 |
| II-30 | 6.8 | 4.1 | 2.8 | 5.6 | 2.3 | 13.0 | 4.8 | 2.2 |
| II-31 | 4.3 | 3.0 | 2.0 | 2.8 | 1.7 | 6.0 | 3.1 | 1.2 |
| II-32 | 50.1 | >62.5 | >62.5 | >62.5 | 33.9 | >62.5 | >62.5 | >62.5 |
| II-36 | 2.1 | 7.1 | 9.7 | 7.2 | 7.5 | 9.4 | 9.5 | 7.9 |
| II-44 | <0.98 | 2.4 | 3.7 | 3.0 | 3.2 | 6.1 | 8.6 | 3.5 |
| II-47 | 1.7 | 5.1 | 9.3 | 5.2 | 5.3 | 6.4 | 7.1 | 3.5 |
| II-48 | 1.4 | 4.4 | 7.4 | 4.3 | 4.4 | 5.9 | 11.2 | 3.3 |
| II-49 | >62.5 | >62.5 | >62.5 | >62.5 | >62.5 | >62.5 | >62.5 | >62.5 |

In Vitro Anti-*T. Cruzi* Activity—Tables 2-4.

*Trypanosoma cruzi* (Tulahuen C4) transfected with β-galactosidase (Lac Z) gene was obtained from Instituto de Investigaciones Cientificas Avanzadas y servicios de Alta Tecnología—Panamá (AIP). This transfected *T. cruzi* can be made using, for example, the procedures provided in Buckner et al., *Efficient technique for screening drugs for activity against Trypanosoma cruzi using parasites expressing β-galactosidase*, Antimicrob. Agents Chemother. 1996, Vol. 40, pp. 2592-2597. This strain permits high throughput screening of compounds using a colorimetric enzyme assay. Compounds that inhibit the growth of *T. cruzi* (Tulahuen C4) will have no or little color while those that do not inhibit growth will permit the strain to grow as determined by a purple color change. The strain was maintained in monolayer VERO cells (African Green Monkey kidney epithelial cells) in complete RPMI 1640 medium without phenol red (Sigma company, St. Louis Mo.), supplemented with 10% heat inactivated fetal bovine serum. All cultures and assays were conducted at 37° C. under an atmosphere of 5% $CO_2$, 95% air mixture.

The antitrypanoside activity of compounds was evaluated by the colorimetric method based on the reduction of the substrate chlorophenol red β-D-galactopyranoside (CPRG) by β-galactosidase resulting from the expression of the gene for *T. cruzi* Tulahuen C4. The assay was performed in 96 well plates containing monolayer VERO cells which were infected with $5 \times 10^4$ trypomastigotes (Tulahuen C4) per well, 24 hours later 10 μg/mL of each compound were added and incubated at 37° C. After 120 hours 25 μl of 900 μM CPRG substrate (Roche) solution were added to each well to determine the antitrypanoside activity of the compound. Then they were incubated at 37° C., for 4-5 hours until color developed. The compounds that had antitrypanoside activity (<50% growing inhibition) were then assayed to determine the inhibitory concentration for 50% growth of the parasites ($IC_{50}$). These compounds were evaluated at 10, 2, 0.4, 0.8, and 0.16 μg/mL. Each compound and concentration was made in duplicate. The intensity of color resulting from the cleavage of CPRG by β-galactosidase was measured at 570 nm using a VersaMax Micro™ microplate reader. The $IC_{50}$ is of the compounds were calculated by logarithmic regression of the OD values obtained, compared with the untreated control. All active compounds also went through an evaluation of the cytotoxicity using Thiozol Blue (MTT; 3-[4.5 dimethylthiazol-2-yl]-2,5-diphenyl tetrazolium bromide) (Aldrich, St. Louis Mo.). This can be important because in some instances compounds that may inhibit the parasite may also be toxic, and thus may factor against a drug candidate. This reaction was measured at 570 nm using a VersaMax Micro™ microplate reader. Nifurtimox (Bayer) was used as positive control at concentrations of 0.1, 1, and 10 βg/mL. The negative control comprised a media containing 0.1% DMSO. $IC_{50}$ is the concentration that produces a 50% inhibitory effect. VERO are normal African green monkey kidney epithelial cells. SI is the Selectivity index which is $IC_{50, VERO}/IC_{50, T. cruzi}$. ND means the data was not determined.

Table 2 ($IC_{50}$ reported in μg/mL)) is an expanded data set of Table 3 ($IC_{50}$ reported in μM).

TABLE 2

In vitro Anti-*T. cruzi* Activity of Some Compounds; Expanded Data Set

| Compound | T. cruzi Inhib. (%) | $IC_{50}$ - T. cruzi (μg/mL) | $IC_{50}$ - VERO Cytotoxicity (μg/mL) | SI |
|---|---|---|---|---|
| I-01 | 41.36 | ND | ND | — |
| I-02 | 11.77 | ND | ND | — |
| I-03 | 19.79 | ND | ND | — |
| I-04 | 12.96 | ND | ND | — |
| I-05 | 68.88 | 5.98 | 5.00 | 0.84 |
| I-06 | 49.61 | ND | ND | — |
| I-07 | 20.47 | ND | ND | — |
| I-10 | 63.54 | 7.28 | 48.00 | 6.59 |
| I-19 | 74.13 | 7.33 | 49.00 | 6.68 |
| I-01 | 28.97 | ND | ND | — |
| I-02 | 22.80 | ND | ND | — |
| I-03 | 7.78 | ND | ND | — |
| I-04 | 3.24 | ND | ND | — |
| I-05 | 38.57 | ND | ND | — |
| I-06 | 69.78 | 2.97 | 8.00 | 2.69 |
| I-07 | 27.74 | ND | ND | — |
| I-08 | 71.54 | 6.70 | 6.00 | 0.90 |
| I-09 | 52.58 | 7.44 | 28.00 | 3.76 |
| I-10 | 62.86 | 8.14 | 38.00 | 4.67 |
| I-11 | 72.39 | 5.37 | 54.00 | 10.06 |
| I-12 | 64.18 | 6.53 | 3.00 | 0.46 |
| I-13 | 68.64 | 1.62 | 5.00 | 3.09 |
| I-14 | 66.33 | 3.30 | 4.00 | 1.21 |
| I-15 | 66.50 | 2.29 | 6.00 | 2.62 |
| I-16 | 63.41 | 5.95 | 6.00 | 1.01 |
| I-17 | 67.75 | 5.38 | 38.00 | 7.06 |
| I-18 | 27.88 | ND | ND | — |
| I-19 | 58.82 | 5.35 | 29.00 | 5.42 |
| I-20 | 76.07 | 1.50 | 18.00 | 12.00 |
| I-21 | 47.73 | ND | ND | — |
| I-22 | 1.25 | ND | ND | — |
| I-23 | 66.55 | 5.27 | 5.00 | 0.95 |
| I-24 | 60.23 | 6.28 | 77.00 | 12.26 |
| I-25 | 51.24 | 3.73 | 52.00 | 13.94 |
| I-26 | 73.63 | 0.52 | 1.00 | 1.92 |
| I-27 | 77.18 | 0.67 | 1.00 | 1.49 |
| I-28 | 59.09 | 4.14 | 65.00 | 15.70 |
| II-15 | 59.79 | 7.28 | 83.00 | 11.40 |
| II-51 | −1.61 | ND | ND | — |
| II-28 | 74.66 | 6.50 | 27.00 | 4.15 |
| II-14 | 2.00 | ND | ND | — |
| II-27 | 78.88 | 4.37 | 7.00 | 1.60 |
| II-22 | 11.62 | ND | ND | — |
| II-01 | 80.12 | 3.92 | 29.00 | 7.40 |
| II-16 | 58.57 | 8.74 | 124.00 | 14.19 |
| II-15 | 31.32 | ND | ND | — |

TABLE 3

In vitro Anti-*T. cruzi* Activity of Some Compounds

| Compound | $IC_{50}$ (μM)[a] | | SI[c] |
|---|---|---|---|
| | T. cruzi | VERO[b] | |
| I-07 | >25 | ND[d] | — |
| I-03 | >100 | ND | — |
| I-04 | >100 | ND | — |
| I-01 | >25 | ND | — |
| I-02 | >25 | ND | — |
| I-05 | >25 | ND | — |
| I-06 | 9.4 | 25.5 | 2.7 |
| I-10 | 21.4 | 99.9 | 4.7 |
| I-19 | 13.6 | 73.5 | 5.4 |
| I-08 | 17.1 | 17.1 | 1.0 |
| I-24 | 17.2 | 211.3 | 12.3 |
| I-11 | 14.2 | 141.9 | 9.9 |
| I-09 | 20.3 | 76.4 | 3.8 |
| I-18 | >25 | ND[d] | — |
| I-17 | 13.1 | 92.6 | 7.1 |
| I-20 | 3.4 | 40.9 | 12.0 |

TABLE 3-continued

In vitro Anti-*T. cruzi* Activity of Some Compounds

| | IC$_{50}$ (μM)[a] | | |
|---|---|---|---|
| Compound | *T. cruzi* | VERO[b] | SI[c] |
| I-12 | 15.6 | 7.2 | 0.5 |
| I-14 | 8.6 | 10.4 | 1.2 |
| I-23 | 14.3 | 13.6 | 0.9 |
| I-15 | 6.2 | 16.3 | 2.6 |
| I-16 | 13.9 | 13.9 | 1.0 |
| I-13 | 4.1 | 12.6 | 3.1 |
| I-25 | 6.9 | 96.3 | 13.9 |
| I-21 | >25 | ND | — |
| I-26 | 1.5 | 2.8 | 1.9 |
| I-27 | 1.9 | 2.8 | 1.5 |
| I-22 | >100 | ND | — |
| I-28 | 12.2 | 190.9 | 15.6 |
| Nifurtimox | 0.52 | 80.1 | 154.0 |

[a]IC$_{50}$: concentration that produces 50% inhibitory effect.
[b]VERO, normal African green monkey kidney epithelial cells.
[c]SI: Selectivity index = IC$_{50,\ VERO}$/IC$_{50,\ T.\ cruzi}$.
[d]Not determined

TABLE 4

In vitro Anti-*T. cruzi* Activity of Some Compounds

| Compound | *T. cruzi* IC$_{50}$[a] (μg/mL) Lab A[e] | *T. cruzi* IC$_{50}$ (μg/mL) Lab B[e] | Cytotoxicity VERO[b] Lab B | Selectivity Index[c] Lab B |
|---|---|---|---|---|
| PC | 4.1 | 4.7 | 9.0 | 1.9 |
| II-01 | 1.9 | 4.4 | 8.0 | 1.8 |
| II-02 | ND[d] | 4.7 | 1.0 | 0.2 |
| II-03 | ND | 4.8 | 5.0 | 1.1 |
| II-04 | 0.4 | 0.5 | 7.0 | 14.6 |
| II-05 | ND | 49.50 | 11.0 | — |
| II-06 | ND | 48.50 | 4.0 | — |
| II-07 | 0.9 | 1.8 | 1.0 | 0.5 |
| II-08 | 1.3 | 4.1 | 5.0 | 1.2 |
| II-09 | 2.6 | 3.7 | 4.0 | 1.1 |
| II-10 | ND | 5.4 | 6.0 | 1.1 |
| II-11 | 1.5 | 5.7 | 5.0 | 0.9 |
| II-12 | 2.3 | 8.0 | 6.0 | 0.7 |
| II-13 | ND | 6.8 | 12.0 | 1.8 |
| II-14 | 3.0 | 43.0 | 11.0 | — |
| II-15 | 2.8 | 6.2 | 4.0 | 0.6 |
| II-16 | 4.9 | 20.5 | ND | — |
| II-17 | 10.2 | 7.7 | 3.0 | 0.4 |
| II-18 | 1.2 | 4.8 | 3.0 | 0.6 |
| II-19 | 0.6 | 6.8 | 1.0 | 0.1 |
| II-20 | ND | 5.0 | ND | — |
| II-21 | 0.1 | 1.2 | <0.08 | 0.1 |
| II-22 | ND | 1.0 | ND | — |
| II-23 | 1.1 | 30.0 | ND | — |
| II-24 | ND | 4.0 | 3.0 | 0.8 |
| II-25 | 0.5 | 5.2 | 3.0 | 0.6 |
| II-26 | 1.9 | 6.0 | 6.0 | 1.0 |
| II-27 | ND | 3.5 | 6.0 | 1.7 |
| II-28 | 1.6 | 4.5 | 7.0 | 1.6 |
| II-29 | ND | 7.3 | 5.0 | 0.7 |
| II-30 | 1.1 | 7.9 | 6.0 | 0.8 |
| II-31 | 0.8 | 3.6 | 3.0 | 0.8 |
| II-32 | ND | 19.0 | ND | — |
| II-36 | 5.3 | 24.5 | ND | — |
| II-44 | 3.2 | 3.7 | 10.0 | 2.7 |
| II-47 | 1.3 | 4.4 | 4.0 | 0.9 |
| II-48 | 4.8 | 6.0 | 6.0 | 1.0 |
| II-49 | ND | 12.5 | ND | — |

[a]IC$_{50}$: concentration that produces 50% inhibitory effect.
[b]VERO, normal African green monkey kidney epithelial cells.
[c]SI: Selectivity index = IC$_{50,\ VERO}$/IC$_{50,\ T.\ cruzi}$.
[d]Not determined.
[e]Lab A and Lab B experiments were performed at different facilities.

In general, compound cytotoxicities were higher than their dihydro counterparts lacking the α,β unsaturated carbonyl group, which could react with nucleophiles such as glutathione (GSH). I-05 and I-06 were more active than I-01, I-02, I-10, and I-19. The lower cytotoxic activity of I-01, I-02, I-10, and I-19 might be explained by the substitutions on the ortho position of the ring, which could affect the planarity of the molecule. Compound I-10 is slightly less active than its structurally related I-01, this might indicate that the cytotoxicity decreases as the size of the ortho substituent on the ring increases; however, it might also demonstrate that some variations are possible in the substitution pattern before the activity is lost. Although active, it can be observed that compounds bearing electron withdrawing groups on the $R^3$ ring (e.g., I-12, I-13, I-14, I-15, I-16, I-23, I-25, I-26, and I-27) could be highly toxic to VERO cells. On the other hand, compounds having electron donating groups on the $R^3$ ring (e.g., I-11, I-17, I-20, I-24, and I-28) could have selectivity indexes of at least 7. In these data, the addition of an extra double bond produces the loss of activity when compared with compounds I-07 and I-21. The high activity of pyridinium $R^3$ compounds (I-26 and I-27) could not be maintained by the pyrrole analog I-22. However, when pyrrole was replaced by furan (I-28), we obtained the highest selectivity index of the series.

Anti-Tuberculosis Assays Using *M. tuberculosis* H37Rv and *M. tuberculosis* MDR—Tables 5 and 6

Table 5 shows the anti-Tuberculosis activity of some compounds against two different strains of *M. tuberculosis* (H37Rv and MDR). Compounds containing a para Chloro (4-Cl or p-Cl) substituent or ortho Fluoro (2-F or o-F) in $R^3$, showed the highest activity and lowest cytotoxicity against VERO cells (normal African green monkey kidney epithelial cells).

For the preparation of the inoculum, a suspension of *M. tuberculosis* was made by mixing growth from slants (20-30 days old) with 100 μL of Tween 80 into 0.2% bovine serum albumin (Sigma Chemical Co., St. Louis, Mo.). Turbidity of the suspension was then adjusted to a McFarland standard No. 1 (3×10$^7$ CFU/mL) by adding Tween 80 and bovine serum albumin. The bacterial suspension (300 μL) was further transferred to 7.2 mL of 7H9GC broth (4.7 g of Middlebrook 7H9 broth base (Difco, Detroit, Mich.), 20 mL of 10% glycerol, 1 g of Bacto Casitone (Difco), 880 mL of distilled water, 100 mL OADC (oleic acid, albumin, dextrose, catalase) (Remel, Lenexa, Kans.). For the bioassay, pure compounds were resuspended in DMSO at a concentration of 4 mg/mL (stock solution). These stock solutions were further diluted with appropriate volumes of 7H9GC broth to yield final concentrations of 0.4 to 25 μg/mL. Final compound concentration ranges of standard antibiotics used as positive controls were 0.125 to 32 μg/mL for isoniazid and 0.063 to 16 μg/mL for rifampin. The compound (100 μL) was mixed in the wells with 100 μL of bacterial inoculum, resulting in a final bacterial concentration of approx. 1.2×10$^6$ CFU/mL. The wells in column 11 served as inoculum-only controls. Solvent (DMSO) was included in every experiment as a negative control. The plates were sealed in plastic bags and then incubated at 37° C. for 5 days. On day 5, 50 μL of the tetrazolium-Tween 80 mixture was added to the wells and the plate was incubated at 37° C. for 24 h. The tetrazolium-Tween 80 mixture was 1.5 mL of tetrazolium [3-(4,5-dimethylthiazol-2-yl)-2,5-diphenyltetrazolium bromide] (Aldrich Chemical Co., Milwaukee, Wis.) at a dilution of 1 mg/mL in absolute ethanol and 1.5 mL of 10% Tween 80. After the incubation period, the growth of the microorganism was visualized by the change in color of the dye from yellow to purple. The tests were carried out in triplicate. MIC is defined as the lowest compound that prevents the aforementioned change in color. 'ND' means not determined.

TABLE 5

Anti-Tuberculosis Bioassays

| Compound | Mycobacterium MIC (mg/mL) | | VERO Cells IC$_{50}$ (mg/mL) |
|---|---|---|---|
| | H$_{37}$Rv | MDR | |
| II-01 | 6.25 | 6.25 | ND |
| II-14 | >25 | >25 | ND |
| II-15 | >25 | >25 | ND |
| II-16 | >25 | >25 | ND |
| II-51 | >25 | >25 | ND |
| II-22 | >25 | >25 | ND |
| II-28 | 12.5 | 6.25 | >80 (SI ≥ 10) |
| II-27 | 3.12 | 3.12 | 27.7 (SI = 9) |

Table 6 displays results from in vitro low oxygen recovery assays (LORA) and conventional aerobic (MABA) culture assays. Prior to use, cultures were thawed, diluted in Middlebrook 7H12 broth (Middlebrook 7H9 broth containing 1 mg/ml casitone, 5.6 µg/ml palmitic acid, 5 mg/ml bovine serum albumin, and 4 µg/ml catalase, filter-sterilized), and sonicated for 15 s. Cultures were diluted to obtain an A$_{570}$ of 0.03-0.05 and 3000-7000 relative light units (RLU) per 100 µl. This corresponds to 5×10$^5$ to ~2×10$^6$ cfu/ml. Two-fold serial dilutions of the antimicrobial agents were prepared in a volume 100 µL in black 96 well microtiter plates and 100 µl of the cell suspension was added. For LORA, the microplate cultures were placed under anaerobic conditions (oxygen less than 0.16%) using an Anoxomat Model WS-8080 (MART Microbiology) using three cycles of evacuation and filling with a mixture of 10% H$_2$, 5% CO$_2$, and the balance N$_2$. An anaerobic indicator strip was placed inside the chamber to visually confirm the removal of oxygen. Plates are incubated at 37° C. for 10 days and then transferred to an ambient gaseous condition (5% CO$_2$-enriched air) incubator for a 28 hour "recovery". Colony forming units (determined by sub-culture onto 7H11 agar) during the day incubation did not increase and remained essentially unchanged. On day 11 (after the 28 hr aerobic recovery) 1000 culture were transferred to white 96-well microtiter plates for determination of luminescence. For conventional assay, the microplate cultures were placed under ambient gaseous condition (5% CO$_2$-enriched air) incubator for 7 days and 100 µl culture was transferred to white 96-well microtiter plates for determination of luminescence. A 10% solution of n-decanal aldehyde (Sigma) in ethanol was freshly diluted ten-fold in PBS and 1000 was added to each well with an auto injector. Luminescence was measured in a Victor2 multilabel reader (PerkinElmer Life Sciences) using a reading time of 1 second. The MIC was defined as the lowest drug concentration effecting an inhibition of >90% relative to drug-free controls. MIC values were numerically extrapolated from transformed inhibition-concentration plots as previously described.

TABLE 6

Anti-Tuberculosis Bioassays

| Compound | MIC µg/mL MABA (MIC µg/mL LORA) | Cytotoxicity VERO cell (µg/mL) | Selectivity Index H37Rv (Selectivity Index LORA) |
|---|---|---|---|
| PC | 82.5 | 26.9 | 0.3 |
| II-01 | 23.4 | 11.1 | 0.5 |
| II-02 | >100 | ND | — |
| II-03 | >100 | ND | — |
| II-04 | 11.7 | 1.2 | 0.1 |
| II-05 | >100 | ND | — |
| II-06 | >100 | ND | — |
| II-07 | >100 | ND | — |
| II-08 | >100 | ND | — |
| II-09 | 23.4 | 14.6 | 0.6 |
| II-10 | 24.1 (9.1) | 76.7 | 3.2 (8.5) |
| II-11 | 40.4 | 22.7 | 0.6 |
| II-12 | >100 | ND | — |
| II-13 | >100 | ND | — |
| II-14 | >100 | ND | — |
| II-15 | >100 | ND | — |
| II-16 | >100 | ND | — |
| II-17 | >100 | ND | — |
| II-18 | 11.9 (2.9) | 12.3 | 1.0 (4.3) |
| II-19 | 6.2 | 4 | 0.7 |
| II-20 | >100 | ND | — |
| II-21 | 44.9 | 10.8 | 0.2 |
| II-22 | >100 | ND | — |
| II-23 | >100 | ND | — |
| II-24 | 6.1 (6.0) | 33.5 | 5.5 (5.5) |
| II-25 | 5.9 (5.8) | 7.6 | 1.3 (1.3) |
| II-26 | 23.2 | 12.8 | 0.6 |
| II-27 | >100 | ND | — |
| II-28 | >100 | ND | — |
| II-29 | 42.6 | 29.3 | 0.7 |
| II-30 | >100 | ND | — |
| II-31 | 9.4 | 7.7 | 0.8 |
| II-32 | >100 | ND | — |
| II-36 | 86.3 | 29.6 | 0.3 |
| II-44 | 62.4 | 32.7 | 0.5 |
| II-47 | 23.4 (2.8) | 32.3 | 1.4 (11.5) |
| II-48 | 46.2 | 32.9 | 0.7 |
| II-49 | >100 | ND | — |
| Rifampin | 0.09 | 97.2 | 1025.8 |

The fatty acid elongation system FAS-II is involved in the biosynthesis of mycolic acids, which are major and specific long-chain fatty acids of the cell envelope of *Mycobacterium tuberculosis* and other mycobacteria, including *Mycobacterium smegmatis*. The protein MabA, also named FabG1, may be part of FAS-II and may catalyze the NADPH-specific reduction of long chain β-ketoacyl derivatives. This activity could correspond to the second step of an FAS-II elongation round. FAS-II may be inhibited by the antituberculous drug isoniazid through the inhibition of the 2-trans-enoyl-acyl carrier protein reductase InhA. Thus, inhibition of MabA can be used in the bioassay to measure the anti-tuberculosis activity of a given compound.

Luminescence-based low oxygen recovery assay (LORA) is a bioassay developed to screen antimicrobial agents against the physiological state of non-replicating persistence *Mycobacterium tuberculosis* (NRP-TB) responsible for antimicrobial tolerance in many bacterial infections.

Anti-*Leishmania amazonensis* Assays—Tables 7, 8a, and 8b

To test for anti-Leishmaniasis, the compounds were first tested against the parasite (i.e., amastigotes), if they exhibit a high activity, then the compounds were tested in macrophages. Experiments were conducted on promastigotes and axenic amastigotes of *L. amazonensis* (strain MHOM/BR/76/LTB-012).

Promastigotes were maintained at 25° C.±1° C. by weekly sub-passages in RPMI 1640 medium with 25 mM HEPES and 2 mM NaHCO$_3$ (pH 7.2) and supplemented with 20% heat-inactivated fetal bovine serum in 25 cm$^2$ tissue culture flasks. Axenically grown amastigotes were maintained by weekly sub-passages in MAA/20 medium at 32° C.±1° C. in 25 cm² tissue culture flasks. Cultures were initiated with 5×10⁵ promastigotes or amastigotes/mL in 25 cm² tissue culture flasks with 5 mL of medium. To determine the activity of the compounds, the 3-(4,5-dimethylthiazol-2-yl)-2,5-diphenyltetrazolium bromide (MTT) micromethod was used. Briefly, 100 μL of axenically grown promastigotes or amastigotes, from late log phage of growth, was seeded in 96-well flat bottom microtiter plates. Compounds, dissolved in DMSO, were added at final concentrations ranging from 100 to 1 μg/mL. The final DMSO concentration was not greater than 0.1%. After 72 h of incubation, 10 μL of MTT (10 mg/mL) was added to each well and plates were further incubated for 4 h. The enzymatic reaction was then stopped with 100 μL of 50% isopropanol-10% sodium dodecyl sulphate and incubated for an additional 30 min under agitation at room temperature (e.g., 25° C.). Finally, the optical density (OD) was read at 570 nm with a 96-well scanner (Bio-Rad).

Peritoneal macrophages were prepared as follows. Non-inflammatory macrophages (10⁶) were collected from each BALB/C mouse. The cells adhered at 37° C. after 2 h under 5% $CO_2$ in a $CO_2$ incubator. The plates were then rinsed two to three times with 0.5 mL of RPMI+buffer MOPS without fetal calf serum to eliminate non-adhering cells. The supernatant on the plates was replaced by fresh medium (RPMI+ glutamine+FCS+antibiotics), 0.5 mL of medium per well. To determine the toxicity of the compounds to macrophages, dilutions of compounds were added on a part of the macrophages prepared above. The contact between the compounds and macrophages alone was 48 h at 37° C. in 5% $CO_2$. The medium was then removed and 1 μL of sterile Trypan Blue was added. Cover glasses N° 1 were left where cells were plated and then the number of macrophages in a microscope was determined with a haemocytometer. All experiments were performed in triplicate.

TABLE 7

In Vitro Activity of Compounds Against Axenic Amastigotes of *L. amazonensis* and Macrophage

| Compounds | $IC_{50}$ (μM)[a] | | $SI^b$ |
|---|---|---|---|
| | *L. amazonensis* | Macrophage | |
| I-01 | 17.2 | ND[c] | — |
| I-02 | >300 | ND | — |
| I-08 | 9.4 | 14.8 | 1.6 |
| I-24 | 79.8 | ND | — |
| I-10 | 5.5 | 18.7 | 3.4 |
| I-11 | 8.7 | 13.1 | 1.5 |
| I-09 | 85.2 | ND | — |
| I-18 | 107.2 | ND | — |
| I-19 | 6.6 | ND | — |
| I-17 | 134.5 | ND | — |
| I-20 | 8.2 | 12.0 | 1.5 |
| I-12 | 127.6 | ND | — |
| I-14 | 9.4 | 13.0 | 1.4 |
| I-23 | 9.5 | 13.8 | 1.5 |
| I-15 | 9.5 | 13.3 | 1.4 |
| I-16 | 7.9 | 5.4 | 0.7 |
| I-13 | 8.3 | 13.2 | 1.6 |
| I-25 | >180 | ND | — |
| I-21 | 75.2 | ND | — |
| I-26 | 0.6 | ND | — |
| I-27 | 1.1 | 12.5 | 11.4 |
| I-22 | 94.3 | ND | — |
| I-28 | >300 | ND | — |
| I-29 | 15.9 | 27.0 | 1.7 |
| I-41 | 7.4 | 16.5 | 2.2 |
| I-05 | 10.0 | 166.2 | 16.6 |
| I-31 | 12.0 | 17.6 | 1.5 |
| I-30 | 15.7 | 21.7 | 1.4 |
| I-37 | 14.9 | ND | — |
| I-06 | 4.1 | 157.2 | 38.3 |
| I-36 | 6.4 | >300 | >50 |
| I-38 | 9.7 | ND | — |
| I-32 | 8.6 | 17.1 | 2.0 |
| I-33 | 11.2 | 19.0 | 1.7 |
| I-40 | 11.8 | 28.8 | 2.4 |
| I-34 | 11.8 | 16.0 | 1.4 |
| I-35 | 10.6 | 14.6 | 1.4 |
| I-42 | 1.1 | 11.5 | 10.5 |
| I-39 | 52.6 | ND | — |
| I-43 | 4.6 | 384.3 | 83.5 |
| I-44 | 1.3 | >250 | >200 |
| I-45 | 11.7 | 142.9 | 12.2 |
| I-46 | 6.2 | 132.5 | 21.4 |
| Amphotericin B | 0.1 | 5.3 | 76.0 |

[a]$IC_{50}$: concentration that produces 50% inhibitory effect.
[b]SI: Selectivity index = $IC_{50, macrophage}/IC_{50, L. amazonensis}$.
[c]Not determined.

As shown in Table 7, eight of the most active compounds (I-5, I-6, I-27, I-26, and I-42 to I-46) showed a selectivity index (SI) greater the 10. Among the two largest series of compounds (2',4'-diallyloxy-6'-methoxychalcones, 2',4'-AC and 2',4'-dihydroxy-6'-methoxychalcones, 2',4'-HC), it was the 2',4'-HC series, which showed the a better selectivity against the axenic amastigotes of *L. amazonensis*, even though they sometimes do not have a higher $IC_{50}$ as compared to those in the 2',4'-AC series. Among compounds I-1, I-5, I-10, and I-44, which differ only on the substitution pattern on ring A, can be observed that having a methoxymethyl substituent on the 4'-position, not only maintains the activity of the molecules, but also greatly enhances its selectivity against the parasite, when compared to its allyoxy and hydroxy analogs. This observation suggests that there exists considerable tolerance for the size and substitution pattern on ring A. In the same way, the presence of the 2',4'-diallyloxy moieties on the ring A seem to dramatically decrease the antileishmanial character and SI of the chalcones when comparing compounds I-9, I-12, I-17, I-18, I-24, I-25, and I-28, with their corresponding 2',4'-dihydroxy substituted counterparts. These results appear to be in agreement with the results reported by Liu et al. *Bioorg. Med. Chem*. Vol. 11 p. 2729 (2003). When comparing the rest of active 2',4'-AC (I-8, I-10, I-11, I-14, I-15, I-16, I-19, I-20, and I-23) against their corresponding 2',4'-HC (I-5, I-6, I-29, I-31, I-33, I-34, I-35, I-38, and I-40) all of them bearing electron donating or electron withdrawing groups on the ring B; it appears that the antiparasitic activity is independent of the substitution pattern on the ring A, since the antileishmanial activity is conserved for each analog pair. This appreciation is also applicable for not-as-active compounds such I-21 and I-39, in which can also be seen that the enlargement of the double bond on the α-β unsaturated bridge results in a loss of bioactivity.

In Tables 8a and 8b, the $IC_{50}$ data are reported in units of μM.

TABLE 8a

| Compound | Cytotoxicity Against Amastigotes IC$_{50}$ (μM) | Cytotoxicity Against Macrophages IC$_{50}$ (μM) |
|---|---|---|
| II-28 | 3.3 | >10 |
| II-14 | 10.5 | >10 |
| II-27 | 3.2 | >10 |
| II-22 | 33.8 | >10 |
| II-01 | 3.2 | ND |
| II-16 | 21.9 | ND |
| II-15 | 31.4 | ND |
| Amphotericin B (μM) | 0.14 | 5.4 |

ND—Not Determined

TABLE 8b

| Compound | L. amazonensis IC$_{50}$ (μM) | Cytotoxicity Macrophages IC$_{50}$ (μM) | Selectivity Index |
|---|---|---|---|
| PC | 12.0 | 7.4 | 0.6 |
| II-01 | 13.5 | 8.7 | 0.6 |
| II-02 | 4.6 | 6.0 | 1.3 |
| II-03 | 14.0 | 5.7 | 0.4 |
| II-04 | 5.5 | 0.6 | 0.1 |
| II-05 | 13.7 | 6.3 | 0.5 |
| II-06 | 5.3 | 50.9 | 9.6 |
| II-07 | 1.3 | 3.0 | 2.3 |
| II-08 | 0.6 | 2.4 | 3.8 |
| II-09 | 13.5 | 57.8 | 4.3 |
| II-10 | 16.1 | 21.6 | 1.3 |
| II-11 | 12.2 | 5.5 | 0.5 |
| II-12 | 10.4 | 5.7 | 0.6 |
| II-13 | 12.2 | 53.0 | 4.3 |
| II-14 | 2.9 | 3.6 | 1.2 |
| II-15 | 2.6 | 8.5 | 3.3 |
| II-16 | 15.7 | 46.4 | 3.0 |
| II-17 | 2.6 | 1.7 | 0.7 |
| II-18 | 1.2 | 0.7 | 0.6 |
| II-19 | 3.0 | 2.9 | 1.0 |
| II-20 | 72.0 | 47.7 | 0.7 |
| II-21 | 0.2 | 2.0 | 13.0 |
| II-22 | 13.6 | 70.4 | 5.2 |
| II-23 | 38.1 | >100 | ND |
| II-24 | 0.7 | 3.1 | 4.1 |
| II-25 | 0.4 | 1.2 | 2.6 |
| II-26 | 3.2 | 3.1 | 1.0 |
| II-27 | 1.1 | 3.3 | 3.1 |
| II-28 | 0.6 | 48.8 | 85.2 |
| II-29 | 0.8 | 3.8 | 5.0 |
| II-30 | 0.3 | 3.0 | 8.8 |
| II-31 | 0.5 | 2.9 | 5.8 |
| II-32 | 10.8 | 53.9 | 5.0 |
| II-36 | 32.5 | 50.7 | 1.6 |
| II-44 | 10.6 | 62.0 | 5.9 |
| II-47 | 9.2 | 51.3 | 5.6 |
| II-48 | 5.5 | 46.7 | 8.5 |
| II-49 | 70.1 | 59.8 | 0.9 |
| Amphotericin B (μM) | 0.1 | 5.4 | 43.5 |

ND—Not Determined

Activity Against Macrophages Infected with Three *Leishmania* Species—Table 9

Table 9 shows the anti-*L. amazonensis*, anti-*L. braziliensis*, and anti-*L. peruviana* activity of nine chalcones, using macrophages infected with the corresponding parasites.

M199 medium was purchased from Invitrogen, L-glutamine, antibiotics and foetal bovine serum from Bio-Witaker Cambrex, and the remaining chemicals were obtained from Sigma-Aldrich. A cloned line of *Leishmania amazonensis*(strain MHOM/BR/76/LTB-012) was used in all experiments. Axenically grown amastigote forms of *L. amazonensis* were maintained by weekly subpassages in MAA/20 medium (Sereno and Lemesre, Antimicrobial Agents and Chemotherapy 41, 972-976 (1997)) at 32±1° C. in 25 cm² tissue culture flasks. *L. peruviana* (strain MHOM/PE/LCA08) and *L. braziliensis* (strainMHOM/PE/PER006) were maintained in the promastigote stage in a biphasic medium (blood agar with 0.89% NaCl, pH 7.4) at 24° C., with sub-passage every 3 to 4 days. Promastigotes (5×10⁶ parasites) were then transferred to 25 cm2 tissue culture flasks containing 5 ml of M199 medium supplemented with 10% foetal bovine serum (FBS), pH 7.4. After 4 days, exponential phase promastigotes were centrifuged for 10 minutes at 1500 g and 4° C. The supernatant was discarded and replaced by fresh M199 medium supplemented with 20% FBS, pH 5.5. Axenic amastigotes transformation was then induced by increasing the temperature to 34° C. and incubating for 96 h (Teixeira et al., Parasitology Research 88, 963-968 (2002)).

Murine macrophages were harvested from peritoneal cavities of 6-8 week-old female BALB/c mice in ice-cold M199 medium supplemented with 10% FBS (Sauvain et al., Phytotherapy Research, 7, 167-171 (1993)). Extracted cells were immediately deposited on sterile 4×4 mm cover glasses and placed in each well of a 96-well plate. Plates were incubated for 24 h at 37° C., 5% CO2 to allow cell adhesion (Castillo et al, Journal of Ethnopharmacology 112, 410-414 (2007)). Pre-warmed complete M199 medium was used twice to remove non-adherent cells. A neutral red method (Fautz et al., Mutation Research 253, 173-179 (1991)) was employed to determine cell concentration. Approximately 7×10⁴ viable cells were deposited in each well for adhesion.

Infection of macrophages by amastigotes was determined as follows. To assess intracellular antileismanial activity, medium in the wells containing the macrophages was replaced by the suspension of amastigotes using an infection ratio of 3/1 amastigotes/macrophages according to Sauvain et al., 1993 (Sauvain et al., Phytotherapy Research, 7, 167-171 (1993)). Twelve hours after infection, a solution of the compounds to be tested was added to the cultures at various concentrations and maintained at 37° C. in 5% CO$_2$ for a further forty-eight hours more. The plates were fixed with methanol and stained with 10% Giemsa stain. The percentage of infected macrophages was determined microscopically at 100 times magnification. The number of intracellular amastigotes was determined in 300 cells. Following Delorenzi et al. Antimicrobial Agents and Chemotherapy, 45, 1349-1354 (2001)) the percentage of infection rate (% IR) of each culture was calculated as follows:

% IR=100−(infection rate of the treated culture/infection rate of the untreated culture)×100.

IC$_{50}$ was also calculated as the dose capable of a 50% reduction in the number of infected cells (calculated using the Excel trend formula). All experiments were performed in triplicate. ANOVA was used to test for statistical significance of differences (Epi-Info, Statview student program). The total parasite burden was calculated as a mean number of amastigotes per cells multiplied by the number of infected macrophages.

TABLE 9

Activity Against Macrophages Infected with *Leishmania* Species

| Compound | L. amazonensis Lma CL1 IC$_{50}$ (μM) | L. braziliensis PER006 IC$_{50}$ (μM) | L. peruviana LCA08 IC$_{50}$ (μM) |
|---|---|---|---|
| I-27 | 0.9 | 1.4 | 4.0 |
| I-05 | 14.3 | 7.66 | 23.0 |

TABLE 9-continued

Activity Against Macrophages Infected with Leishmania Species

| | IC$_{50}$ (μM) | | |
|---|---|---|---|
| Compound | L. amazonensis Lma CL1 | L. braziliensis PER006 | L. peruviana LCA08 |
| I-06 | 16.6 | 8.6 | 19.7 |
| I-36 | 28.5 | 237.0 | 290.2 |
| I-42 | 4.1 | 14.4 | ND$^a$ |
| I-43 | 17.0 | 30.4 | 34.2 |
| I-44 | 12.1 | 5.15 | 110.8 |
| I-45 | 23.9 | 17.2 | 34.8 |
| I-46 | 28.7 | 13.1 | 19.3 |
| II-06 (μg/mL) | ND | 3.5 | 3.2 |
| II-21 (μg/mL) | ND | 0.19 | 0.2 |
| II-28 (μg/mL) | ND | 5.9 | >10 |
| II-30 (μg/mL) | ND | >0.5 | >0.5 |
| II-48 (μg/mL) | ND | 3.2 | 2.0 |
| Amphotericin B | 0.4 | 0.1 | 0.1 |

$^a$Not determined.

Table 9 shows the bioactivities of the nine compounds which showed the highest SI on the axenic amastigotes assay. From this macrophage-infected model, it can be observed that in general, L. peruviana was the species of parasites which showed the strongest resistance towards all chalcones, while L. braziliensis and L. amazonensis seemed to respond differently depending on the type of chalcone administrated. Compound I-27, containing a pyridinyl moiety seemed to exert the highest bioactivities with values ranging from 0.9 to 4.0 μM. Compound I-44 showed an interesting selectivity against L. braziliensis, as well as compound I-36 towards L. amazonensis. Finally, compounds I-5, I-27, I-42, I-43, and I-45, exhibited higher bioactivity in the macrophage-infected model than against free axenic amastigotes of L. amazonensis.

In Vivo Activity on L. Amazonensis-Infected Balb/c Mice—Tables 10 and 11

One in vivo test was used in the study of the antileishmanial activity of the compounds. The in vivo assay is performed by infecting sensitive BALB/c mice with amastigotes of L. amazonensis in the posterior feet (Sauvain et al., Phytotherapy Research, 7, 167-171 (1993)). Treatment started one week after the infection and consisted of intralesional injections three times each week during six weeks. Growth of cutaneous lesions of the mice is observed during seven consecutive weeks, by measuring the thickening of the posterior legs and measuring the parasitic load by fluorescence (Jackson et al., Science, 227, 435-438 (1985), Barreca et al., Diagn. Microbiol. Infect. Dis., 37, 247-251 (2000)) in the foot tissue. The results are compared with those obtained with an established usual antileishmanial drug (antimonial organic salts).

A nodule extracted from a BALB/c mouse, infected six weeks before with the LV79 strain (MPRO/BR/72/M1841), was homogenized in a sterile Potter crusher and taken up in PBS medium (Sigma, USA) in a dilution that gave 200 000 amastigotes in 10 μL volume; the two posterior feet of group of each ten mice are infected. Seven days after infection, the products to be tested and the reference substance were injected into the lesion three times a week during six weeks in the right posterior foot of each mouse. A solvent control was prepared in the same manner.

The thickness of each leg was measured with a Schnell-tester to evaluate the cutaneous fold one week after the infection and during the following seven weeks which is the time required for the development of a leishmanial nodule before ulceration.

The load of parasites was measured two times (after four and seven weeks of treatment respectively) by a method using fluorescence. In every time of evaluation the infected nodules of both later feet were extracted. The infected nodules were weighed and homogenized in a sterile Potter crusher with 20% SFB M199 medium (Sigma, USA). An aliquot of 50 uL was extracted and serial dilutions were realised with the Ethidium reagent diacetate-Orange acridin (EB-FDAmod) (Sigma, USA). Intralesional alive (green) and died (red) amastigotes was placed in an hemocytometer (Bright-line, Sigma) to quantify the viability and the differentiation of the amastigote stage by means of the identification of the nucleus and kinetoplast of green colour. The parasitic load has been expressed by the number of amastigotes ($\times 10^6$)/mg of infected nodule. The student t-test which was used to compare the averages of the parasitic load between two treatments; the significance was defined as p<0.05.

TABLE 10

In vivo Activity on L. amazonensis-Infected BALB/c Mice (n = 10)$^a$

| | | Reduction of parasite burden (%) | |
|---|---|---|---|
| Compound | Lesion diameter (mm)$^b$ | After 4 weeks | After 7 weeks |
| control | 4.7 | — | — |
| I-27 | 4.1 | -4 | 25$^d$ |
| I-42 | 4.6 | 9 | 8$^d$ |
| I-44 | 4.7 | 11 | 17 |
| I-45 | 4.6 | 92 | 35 |
| I-46 | 5.1 | 74 | 41 |
| Glucantime$^c$ | 2.2 | 100 | 100 |

$^a$Effect of treatments after 8 intralesional inoculations.
$^b$Compounds administrated at 5 mg/kg/day.
$^c$N-methylglucamine antimoniate, administrated at 33 mg/kg/day.
$^d$Compounds I-27 and I-42 were analyzed after 6 weeks treatment.

None of the five tested compounds appeared to be as effective as the positive control (Glucantime) to reduce the lesion diameter. However, because this result depends on a number of parameters such, immune response, inflammation process, and parasite virulence (which are not proportional to the parasite load or the parasite burden), we completed the measurement of the mice's footpad with kaliper by counting the L. amazonensis amastigotes in the foot tissue using a fluorescent probe.

From the count, compounds I-45 and I-46 (administrated to the infected mice in a concentration almost seven times lower than the positive control) showed a high reduction of the parasite burden (with P=0.0004 and P=0.0019, respectively) after the initial four weeks of treatment, providing a reduction of the parasite burden of 92% and 74%, respectively. These results were further confirmed by the experiment at the seventh week in which compounds I-45 and I-46 showed a 35% and 41% reduction of parasite burden, respectively. Compounds I-45 and I-46 did not exhibit any cutaneous toxicity at the tested doses and they may not exhibit a reduction of the lesion diameter, perhaps due to their lack of anti-inflammatory activity.

Tables 11a and 11b show the effect of treatments after 8 inoculations intralesional with N-methylglucamine antimoniate (33 mg Sb (v)/kg/day) and eight compounds (5 mg/kg/day) in Leishmania amazonensis-infected BALB/c mice (n=10).

TABLE 11a

After 4 Weeks Treatment

| Compound | Mean lesion wt (mg) (±SD) | % Variation of lesion wt | Mean parasite quantification (per $10^6$) in lesion per mg (±SD) | % reduction of parasite burden in the lesion | Mean lesion size (mm) |
|---|---|---|---|---|---|
| Control | 60.4 (±4.5) | | 1.70 (±0.04) | | 2.8 |
| II-06 | 70.9 (±9.9) | −17 | 1.19 (±0.27) | 30 | 3.0 |
| II-28 | 60.4 (±31.3) | 0 | 0.92 (±0.32) | 46 | 3.6 |
| II-48 | 38.2 (±11.4) | 37 | 0.60 (±0.44) | 65 | 2.8 |
| Glucantime | 5.6 (±0.4) | 91 | 0 (0) | 100 | 2.1 |

TABLE 11b

After 7 Weeks Treatment

| Compound | Mean lesion wt (mg) (±SD) | % Variation of lesion wt | Mean parasite quantification (per $10^6$) in lesion per mg (±SD) | % reduction of parasite burden in the lesion | Mean lesion size (mm) |
|---|---|---|---|---|---|
| Control | 89.1 (±3.6) | | 2.01 (±0.13) | | 4.7 |
| II-06 | 78.4 (±1.6) | 12 | 1.46 (±0.30) | 2 | 4.7 |
| II-28 | 169.1 (±15.3) | −90 | 1.26 (±0.02) | 25 | 5.2 |
| II-48 | 85.0 (±4.5) | 5 | 1.53 (±0.18) | 17 | 4.9 |
| Glucantime | 13.5 (±2.9) | 85 | 0 (0) | 100 | 2.2 |

Studies of $GI_{50}$, TGI, and $LC_{50}$ for Compound II-21 for Several Cell Lines—Table 12

For Table 12, $GI_{50}$, TGI, and $LC_{50}$ are determined as follows. $GI_{50}$ is the concentration of test compound where 100×(T−T0)/(C−T0)=50. See Boyd et al. in *Cytotoxic Anticancer Drugs Models and Concepts for Drug Discovery and Development*; Vleriote et al. Eds.; Kluwer Academic: Hingham, Mass., 1992; pp 11-34 and Monks et al. *JNCI, J. Natl. Cancer Inst.* 1991, Vol. 83, pp. 757-766. The optical density of the test well after a 48-h period of exposure to test drug is T, the optical density at time zero is T0, and the control optical density is C. The $GI_{50}$ measures the growth inhibitory power of the test compound. The TGI is the concentration of test drug where 100×(T−T0)/(C−T0)=0. Thus, the TGI can signify a cytostatic effect. The $LC_{50}$, which can signify a cytotoxic effect, is the concentration of drug where 100×(T−T0)/T0=−50. The control optical density is not used in the calculation of $LC_{50}$.

TABLE 12

$GI_{50}$, TGI, and $LC_{50}$ for Compound II-21

| Panel/Cell Line | $GI_{50}$ (M) | TGI (M) | $LC_{50}$ (M) |
|---|---|---|---|
| Leukemia | | | |
| CCRF-CEM | 2.42E−7 | 7.69E−7 | >1.00E−4 |
| HL-60(TB) | 1.20E−7 | 4.07E−7 | >1.00E−4 |
| K-562 | 2.84E−7 | 1.08E−5 | >1.00E−4 |
| MOLT-4 | 2.61E−7 | 7.74E−7 | >1.00E−4 |
| RPMI-8226 | 3.50E−7 | 1.25E−5 | >1.00E−4 |
| SR | 3.68E−7 | 9.53E−7 | >1.00E−4 |
| Non-Small Cell Lung Cancer | | | |
| A549/ATCC | 3.89E−7 | 1.49E−5 | 7.13E−5 |
| EKVX | 3.17E−7 | 2.05E−5 | >1.00E−4 |
| HOP-62 | 3.95E−7 | 1.77E−5 | >1.00E−4 |
| HOP-92 | 4.17E−7 | 3.10E−5 | >1.00E−4 |
| NCI-H226 | 3.85E−7 | 1.62E−5 | >1.00E−4 |
| NCI-H23 | 7.05E−7 | 3.43E−5 | >1.00E−4 |
| NCI-H322M | 2.16E−7 | 3.50E−5 | >1.00E−4 |
| NCI-H460 | 3.04E−7 | 1.73E−6 | 3.11E−5 |
| NCI-H522 | 4.19E−7 | 2.32E−5 | >1.00E−4 |
| Colon Cancer | | | |
| COLO 205 | 3.15E−7 | 1.47E−5 | 5.45E−5 |
| HCC-2998 | 1.00E−5 | 2.29E−5 | 5.26E−5 |
| HCT-116 | 1.66E−7 | 1.42E−5 | 6.74E−5 |
| HCT-15 | 4.50E−7 | 2.70E−5 | >1.00E−4 |
| HT29 | 1.80E−7 | 1.51E−5 | 4.49E−5 |
| KM12 | 5.15E−7 | 1.27E−5 | 3.81E−5 |
| SW-620 | 5.61E−7 | 1.79E−5 | 5.95E−5 |
| CNS Cancer | | | |
| SF-268 | 3.56E−7 | 1.51E−5 | 8.30E−5 |
| SF-295 | 3.13E−7 | 1.21E−5 | >1.00E−4 |
| SF-539 | 3.91E−7 | 3.84E−6 | 2.92E−5 |
| SNB-19 | 7.67E−7 | 3.41E−5 | >1.00E−4 |
| SNB-75 | 5.85E−7 | 1.47E−5 | 4.93E−5 |
| U251 | 3.69E−7 | 1.21E−5 | 3.48E−5 |
| Melanoma | | | |
| LOX IMVI | 2.56E−7 | | 3.48E−5 |
| MALME-3M | 2.75E−7 | 1.03E−5 | 5.14E−5 |
| M14 | 2.46E−7 | 5.99E−7 | 3.34E−5 |
| MDA-MB-435 | 4.77E−7 | 2.51E−5 | >1.00E−4 |
| SK-MEL-2 | 7.51E−6 | 2.55E−5 | 6.78E−5 |
| SK-MEL-28 | 4.22E−7 | 1.67E−5 | 5.46E−5 |
| SK-MEL-5 | 3.32E−7 | 1.72E−6 | 2.36E−5 |
| UACC-257 | 3.55E−7 | | 4.17E−5 |
| UACC-62 | 3.79E−7 | 6.54E−6 | 4.84E−5 |
| Ovarian Cancer | | | |
| IGROV1 | 4.50E−7 | 2.89E−5 | >1.00E−4 |
| OVCAR-3 | 1.09E−7 | 1.45E−5 | 4.39E−5 |
| OVCAR-4 | 4.31E−7 | 2.63E−5 | >1.00E−4 |
| OVCAR-5 | 8.23E−7 | 3.14E−5 | >1.00E−4 |
| OVCAR-8 | 4.81E−7 | >1.00E−4 | >1.00E−4 |
| NCI/ADR-RES | 4.27E−7 | 5.81E−5 | >1.00E−4 |
| SK-OV-3 | 4.10E−7 | 2.92E−5 | >1.00E−4 |
| Renal Cancer | | | |
| 786-0 | 3.33E−7 | 9.47E−7 | 4.44E−5 |
| A498 | 4.28E−7 | 8.81E−6 | 3.72E−5 |
| ACHN | 3.13E−7 | 1.10E−5 | >1.00E−4 |
| CAKI-1 | 3.13E−7 | 1.48E−5 | >1.00E−4 |
| RXF 393 | 4.23E−7 | 1.06E−5 | 4.53E−5 |
| SN12C | 4.26E−7 | 1.53E−5 | 8.10E−5 |
| TK-10 | 4.86E−7 | 5.66E−5 | >1.00E−4 |
| UO-31 | 2.86E−7 | 1.65E−6 | 6.30E−5 |
| Prostate Cancer | | | |
| PC-3 | 4.31E−7 | 7.11E−5 | >1.00E−4 |
| DU-145 | 4.10E−7 | 1.51E−5 | 5.16E−5 |
| Breast Cancer | | | |
| MCF7 | 3.36E−7 | 1.53E−5 | 8.00E−5 |
| MDA-MB-231/ATCC | 6.03E−7 | 2.97E−5 | >1.00E−4 |
| HS 578T | 7.48E−7 | 2.39E−5 | >1.00E−4 |
| BT-549 | 3.94E−7 | 2.87E−5 | >1.00E−4 |
| T-47D | 7.64E−8 | 2.80E−5 | >1.00E−4 |
| MDA-MB-468 | 2.00E−7 | 5.05E−7 | 4.10E−5 |

Physicochemical Parameters Calculation—Tables 13 and 14.

A computational study for prediction of ADME was used to predict the properties of the compounds and is presented in Tables 13 and 14. Topological polar surface area (TPSA) can be a good indicator of compound absorbance in the intestines, Caco-2 monolayers penetration, and blood-brain barrier crossing. TPSA was used to calculate the percentage of absorption (% ABS) according to the equation: % ABS=109−0.345×TPSA, as discussed above. In addition, the number of rotatable bonds (n-ROTB), and Lipinski's rule of five, was also calculated. From all these parameters it can be observed that although the oral bioavailability of compounds with selectivity indexes of at least 12, (e.g., I-20, I-24, I-25, and I-28) could be affected (e.g., making them less bioavailable inside the microorganism) (n-ROTB ranged from 10 to 16) they exhibited a great % ABS ranging from 84 to 94%. Furthermore, I-20, I-24, and I-28 violate one or none of Lipinski's parameters, making them potentially promising agents for antitrypanosomal therapy.

Polar surface area (TPSA), mi Log P, number of rotatable bonds and violations of Lipinski's rule of five, were calculated using Molinspiration online property calculation toolkit according to previously reported literature—see (Molinspiration Cheminformatics, Bratislava, Slovak Republic, <<http://www.molinspiration.com/services/properties.html>>). Every Log P refers the logarithm of compound partition coefficient between n-octanol and water; variations in this parameter as tabulated below are given by the software used in the calculation.

TABLE 13

Physical Chemical Properties of Some Formula (I) Compounds.[a]

| Cmpd | % ABS | TPSA (Å²) | n-ROTB | Molecular weight | miLogP | KOWLogP | ALogPS 2.1 | LogP (AB/logP) | MLogP | n-OHNH donors | n-ON acceptors | Lipinski's violations |
|---|---|---|---|---|---|---|---|---|---|---|---|---|
| (rule) | | | | <500 | <5 | <5 | <5 | <5 | <4.15 | <5 | <10 | ≤1 |
| I-07 | 82.8 | 76.0 | 6 | 302.3 | 3.26 | 3.85 | 3.21 | 3.14 | 2.33 | 2 | 5 | 0 |
| I-03 | 86.6 | 65.0 | 7 | 316.4 | 3.79 | 4.41 | 3.30 | 3.59 | 2.57 | 1 | 5 | 0 |
| I-04 | 83.4 | 74.2 | 6 | 330.3 | 3.63 | 4.39 | 2.76 | 3.70 | 1.81 | 1 | 6 | 0 |
| I-01 | 86.6 | 65.0 | 6 | 314.3 | 3.83 | 4.20 | 3.61 | 3.73 | 2.49 | 1 | 5 | 0 |
| I-02 | 83.4 | 74.3 | 5 | 328.3 | 3.66 | 4.18 | 2.81 | 3.84 | 1.74 | 1 | 6 | 0 |
| I-05 | 82.8 | 76.0 | 5 | 300.3 | 3.29 | 3.64 | 3.50 | 3.28 | 2.26 | 2 | 5 | 0 |
| I-06 | 79.6 | 85.2 | 4 | 314.3 | 3.12 | 3.62 | 2.81 | 3.40 | 1.50 | 2 | 6 | 0 |
| I-10 | 90.4 | 54.0 | 11 | 380.4 | 5.18 | 5.67 | 4.71 | 5.13 | 2.95 | 0 | 5 | 1 |
| I-19 | 87.2 | 63.2 | 10 | 394.4 | 5.02 | 5.65 | 4.56 | 5.24 | 2.19 | 0 | 6 | 1 |
| I-08 | 93.5 | 44.8 | 10 | 350.4 | 5.13 | 5.59 | 4.55 | 5.17 | 3.52 | 0 | 4 | 1 |
| I-24 | 93.5 | 44.8 | 10 | 364.4 | 5.58 | 6.14 | 4.83 | 5.58 | 3.74 | 0 | 4 | 1 |
| I-11 | 90.4 | 54.0 | 11 | 380.4 | 5.16 | 5.67 | 4.70 | 5.13 | 2.95 | 0 | 5 | 1 |
| I-09 | 82.8 | 76.0 | 9 | 352.4 | 4.58 | 5.33 | 4.19 | 4.62 | 3.03 | 2 | 5 | 1 |
| I-18 | 83.4 | 74.2 | 11 | 396.4 | 4.47 | 4.94 | 4.41 | 4.40 | 2.18 | 1 | 6 | 0 |
| I-17 | 87.2 | 63.2 | 12 | 410.5 | 4.99 | 5.76 | 4.86 | 5.09 | 2.39 | 0 | 6 | 1 |
| I-20 | 84.0 | 72.5 | 13 | 440.5 | 4.76 | 5.10 | 4.95 | 4.60 | 1.84 | 0 | 7 | 1 |
| I-12 | 93.5 | 44.8 | 11 | 418.4 | 6.02 | 6.55 | 5.10 | 6.12 | 4.05 | 0 | 4 | 1 |
| I-14 | 93.5 | 44.8 | 10 | 384.9 | 5.80 | 6.24 | 5.13 | 5.73 | 3.74 | 0 | 4 | 1 |
| I-23 | 93.5 | 44.8 | 10 | 368.4 | 5.29 | 5.79 | 4.78 | 5.22 | 3.63 | 0 | 4 | 1 |
| I-15 | 93.5 | 44.8 | 10 | 368.4 | 5.27 | 5.79 | 4.76 | 5.22 | 3.63 | 0 | 4 | 1 |
| I-16 | 93.5 | 44.8 | 10 | 429.3 | 5.91 | 6.48 | 5.06 | 5.96 | 3.84 | 0 | 4 | 1 |
| I-13 | 77.9 | 90.6 | 11 | 395.4 | 5.09 | 5.41 | 4.50 | 4.96 | 3.30 | 0 | 7 | 1 |
| I-25 | 87.2 | 63.2 | 16 | 541.4 | 7.19 | 8.34 | 5.74 | 7.14 | 3.35 | 0 | 6 | 2 |
| I-21 | 93.5 | 44.8 | 11 | 376.5 | 5.65 | 6.36 | 5.22 | 5.93 | 3.88 | 0 | 4 | 1 |
| I-26 | 89.1 | 57.7 | 10 | 351.4 | 3.84 | 4.40 | 3.59 | 3.79 | 2.13 | 0 | 5 | 0 |
| I-27 | 89.1 | 57.7 | 10 | 351.4 | 3.78 | 4.40 | 3.86 | 3.79 | 2.13 | 0 | 5 | 0 |
| I-22 | 88.1 | 60.6 | 10 | 339.4 | 4.10 | 4.48 | 3.73 | 4.00 | 1.98 | 1 | 5 | 0 |
| I-28 | 89.0 | 57.9 | 10 | 340.4 | 4.20 | 4.96 | 3.65 | 4.31 | 1.98 | 0 | 5 | 0 |

[a] % ABS, percentage of absorption, calculated by % ABS = 109 − (0.345 × TPSA);
TPSA, topological polar surface area;
n-ROTB, number of rotatable bonds;
LogP, logarithm of compound partition coefficient between n-octanol and water;
n-OHNH, number of hydrogen bond donors;
n-ON, number of hydrogen bond acceptors.

TABLE 14

Physical Chemical Properties of Some Formula (II) Compounds.[a]

| Compound | % ABS | TPSA (Å²) | n-ROTB | Molecular Weight | miLogP | n-OHNH donors | n-ON acceptors | Lipinski's violations |
|---|---|---|---|---|---|---|---|---|
| PC | 87.0 | 63.8 | 1 | 220.3 | 1.84 | 3 | 4 | 0 |
| II-01 | 91.7 | 50.2 | 3 | 308.4 | 3.89 | 1 | 4 | 0 |
| II-02 | 91.7 | 50.2 | 3 | 358.5 | 5.05 | 1 | 4 | 1 |
| II-03 | 91.7 | 50.2 | 3 | 358.5 | 5.07 | 1 | 4 | 1 |
| II-04 | 91.7 | 50.2 | 4 | 334.4 | 4.65 | 1 | 4 | 0 |
| II-05 | 91.7 | 50.2 | 3 | 322.4 | 4.34 | 1 | 4 | 0 |
| II-06 | 91.7 | 50.2 | 4 | 336.4 | 4.80 | 1 | 4 | 0 |
| II-07 | 91.7 | 50.2 | 4 | 350.5 | 5.40 | 1 | 4 | 1 |
| II-08 | 91.7 | 50.2 | 4 | 364.5 | 5.60 | 1 | 4 | 1 |
| II-09 | 84.7 | 70.4 | 3 | 324.4 | 3.41 | 2 | 5 | 0 |
| II-10 | 88.5 | 59.4 | 4 | 338.4 | 3.95 | 1 | 5 | 0 |
| II-11 | 88.5 | 59.4 | 4 | 338.4 | 3.92 | 1 | 5 | 0 |

TABLE 14-continued

Physical Chemical Properties of Some Formula (II) Compounds.[a]

| Compound | % ABS | TPSA (Å$^2$) | n-ROTB | Molecular Weight | miLogP | n-OHNH donors | n-ON acceptors | Lipinski's violations |
|---|---|---|---|---|---|---|---|---|
| II-12 | 85.3 | 68.6 | 3 | 352.4 | 3.78 | 1 | 6 | 0 |
| II-13 | 85.3 | 68.6 | 5 | 368.5 | 3.93 | 1 | 6 | 0 |
| II-14 | 82.1 | 77.9 | 6 | 398.5 | 3.52 | 1 | 7 | 0 |
| II-15 | 81.5 | 79.6 | 4 | 354.4 | 3.23 | 2 | 6 | 0 |
| II-16 | 78.3 | 88.9 | 5 | 384.5 | 3.24 | 2 | 7 | 0 |
| II-17 | 85.3 | 68.6 | 9 | 499.4 | 5.96 | 1 | 6 | 1 |
| II-18 | 87.2 | 63.3 | 3 | 298.4 | 3.15 | 1 | 5 | 0 |
| II-19 | 86.2 | 66.0 | 3 | 297.4 | 3.04 | 2 | 5 | 0 |
| II-20 | 87.2 | 63.1 | 3 | 309.4 | 2.60 | 1 | 5 | 0 |
| II-21 | 87.2 | 63.1 | 3 | 309.4 | 2.72 | 1 | 5 | 0 |
| II-22 | 75.9 | 96.0 | 4 | 353.4 | 3.85 | 1 | 7 | 0 |
| II-23 | 75.9 | 96.0 | 4 | 353.4 | 3.80 | 1 | 7 | 0 |
| II-24 | 91.7 | 50.2 | 4 | 376.4 | 4.78 | 1 | 4 | 0 |
| II-25 | 91.7 | 50.2 | 4 | 376.4 | 4.74 | 1 | 4 | 0 |
| II-26 | 91.7 | 50.2 | 3 | 326.4 | 4.05 | 1 | 4 | 0 |
| II-27 | 91.7 | 50.2 | 3 | 326.4 | 4.00 | 1 | 4 | 0 |
| II-28 | 91.7 | 50.2 | 3 | 342.9 | 4.57 | 1 | 4 | 0 |
| II-29 | 91.7 | 50.2 | 3 | 342.9 | 4.52 | 1 | 4 | 0 |
| II-30 | 91.7 | 50.2 | 3 | 387.3 | 4.70 | 1 | 4 | 0 |
| II-31 | 91.7 | 50.2 | 3 | 387.3 | 4.65 | 1 | 4 | 0 |
| II-32 | 83.5 | 74.0 | 3 | 333.4 | 3.64 | 1 | 5 | 0 |
| II-36 | 91.7 | 50.2 | 3 | 288.4 | 4.00 | 1 | 4 | 0 |
| II-44 | 91.7 | 50.2 | 2 | 260.4 | 3.12 | 1 | 4 | 0 |
| II-47 | 91.7 | 50.2 | 3 | 322.4 | 4.34 | 1 | 4 | 0 |
| II-48 | 91.7 | 50.2 | 4 | 288.4 | 4.12 | 1 | 4 | 0 |
| II-49 | 91.7 | 50.2 | 4 | 384.5 | 5.55 | 1 | 4 | 1 |

[a] % ABS, percentage of absorption, calculated by: % ABS = 109 − (0.345 × TPSA);
TPSA, topological polar surface area;
n-ROTB, number of rotatable bonds;
n-OHNH, number of hydrogen bond donors;
n-ON, number of hydrogen bond acceptors.

Having described the invention in detail and by reference to specific embodiments thereof, it will be apparent that modifications and variations are possible without departing from the scope of the invention defined in the appended claims. More specifically, although some aspects of the present invention are identified herein as preferred or advantageous, it is contemplated that the present invention is not necessarily limited to these preferred or advantageous aspects of the invention.

What is claimed is:

1. A method for synthesizing a compound of formula (I) comprising
subjecting

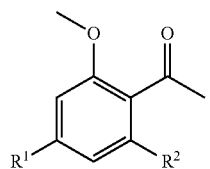

to a condensation reaction, and
recovering a compound of formula (I)

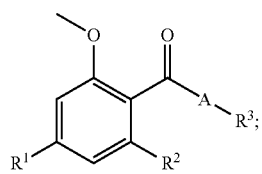

(I)

wherein $R^1$ and $R^2$ are both —OH; $R^1$ and $R^2$ are both —OCH$_2$CH=CH$_2$; $R^1$ and $R^2$ are both —OCH$_2$OCH$_3$; or $R^1$ is —OCH$_2$OCH$_3$ and $R^2$ is —OH;

A is a bivalent, substituted or unsubstituted, branched or unbranched alkane or alkene; and $R^3$ is selected from the group consisting of:

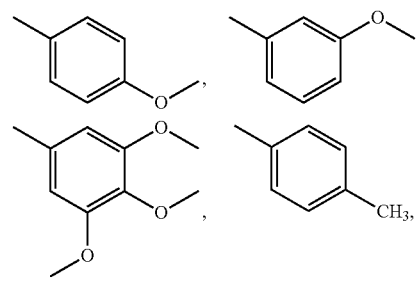

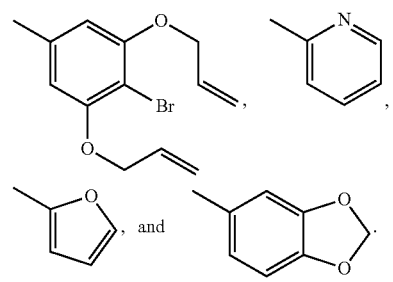

2. A method for synthesizing a compound, comprising: subjecting

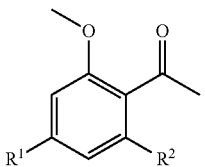

to a condensation reaction, and then a deprotection reaction, and recovering

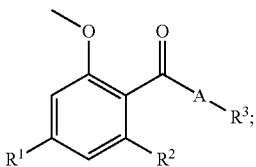

(I)

wherein
R¹ and R² can be the same or different and are selected from the group consisting of: —OH, alkoxy, benzyloxy, —OCH₂—CH=CH₂, and —OCH₂OCH₃;
A is a bivalent, substituted or unsubstituted, branched or unbranched alkane or alkene; and
R³ is a substituted or unsubstituted four-, five-, six-, or seven-member ring that may include one or more heteroatoms in the ring.

3. The method of claim 2, wherein the deprotection reaction is a dealkylation reaction.
4. The method of claim 2, wherein the deprotection reaction comprises combining the product of the condensation reaction with Pd(PPh₃)₄ in K₂CO₃ and MeOH.
5. The compound

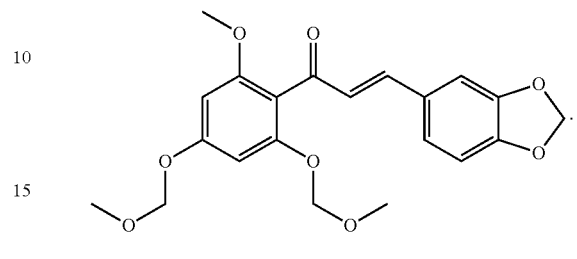

6. A composition comprising the compound of claim 5.
7. The composition of claim 6, wherein the composition is in the form selected from the group consisting of: a solution, an emulsion, a tablet, a capsule, a pill, a gel, an ointment, a cream, a lotion, a food, and a drink.
8. The composition of claim 6, wherein the composition comprises from about 25% to about 75% of the compound.
9. The composition of claim 6, wherein the composition is a pharmaceutical composition.
10. The composition of claim 6, wherein the composition comprises the compound in the form of a pharmacologically acceptable salt.
11. The composition of claim 6, wherein the composition comprises the compound as a component of a molecular complex.

* * * * *